(12) United States Patent
Quinlan et al.

(10) Patent No.: US 11,439,358 B2
(45) Date of Patent: Sep. 13, 2022

(54) METHODS AND SYSTEMS FOR HIGH PERFORMANCE AND VERSATILE MOLECULAR IMAGING

(71) Applicant: Ziteo, Inc., Pleasant Hill, CA (US)

(72) Inventors: Michael Quinlan, San Francisco, CA (US); Lucian Mihailescu, Pleasant Hill, CA (US); Andrei Claudiu Cosma, Emeryville, CA (US)

(73) Assignee: Ziteo, Inc., Pleasant Hill, CA (US)

( * ) Notice: Subject to any disclaimer, the term of this patent is extended or adjusted under 35 U.S.C. 154(b) by 0 days.

(21) Appl. No.: 17/594,192

(22) PCT Filed: Apr. 9, 2020

(86) PCT No.: PCT/US2020/027526
§ 371 (c)(1),
(2) Date: Oct. 6, 2021

(87) PCT Pub. No.: WO2020/210532
PCT Pub. Date: Oct. 15, 2020

(65) Prior Publication Data
US 2022/0087624 A1 Mar. 24, 2022

Related U.S. Application Data

(60) Provisional application No. 62/831,504, filed on Apr. 9, 2019, provisional application No. 62/836,514, filed on Apr. 19, 2019.

(51) Int. Cl.
*A61B 6/03* (2006.01)
*A61B 6/00* (2006.01)

(52) U.S. Cl.
CPC ............ *A61B 6/037* (2013.01); *A61B 6/4258* (2013.01); *A61B 6/4266* (2013.01); *A61B 6/5235* (2013.01)

(58) Field of Classification Search
CPC ..... A61B 6/037; A61B 6/4258; A61B 6/4266; A61B 6/5235
See application file for complete search history.

(56) References Cited

U.S. PATENT DOCUMENTS

| 5,436,958 A | 7/1995 | Taylor |
| 5,453,686 A | 9/1995 | Anderson |

(Continued)

FOREIGN PATENT DOCUMENTS

| CN | 1390335 A | 1/2003 |
| CN | 1792342 A | 6/2006 |

(Continued)

OTHER PUBLICATIONS

International Search Report and Written Opinion dated Aug. 8, 2020; International Application No. PCT/US2020/027526; 15 pages.

(Continued)

*Primary Examiner* — Blake C Riddick
(74) *Attorney, Agent, or Firm* — Fortem IP LLP; Matthew Lincicum

(57) ABSTRACT

Improved imaging devices and methods. A portable SPECT imaging device may co-register with imaging modalities such as ultrasound. Gamma camera panels including gamma camera sensors may be connected to a mechanical arm. A coded aperture mask may be placed in front of a gamma-ray photon sensor and used to construct a high-resolution three-dimensional map of radioisotope distributions inside a patient, which can be generated by scanning the patient from a reduced range of directions around the patient and with radiation sensors placed in close proximity to this patient. Increased imaging sensitivity and resolution is provided. The SPECT imaging device can be used to guide medical interventions, such as biopsies and ablation therapies, and can also be used to guide surgeries.

24 Claims, 36 Drawing Sheets

(56) References Cited

U.S. PATENT DOCUMENTS

| | | | |
|---|---|---|---|
| 5,786,597 A | 7/1998 | Lingren et al. |
| 5,891,034 A | 4/1999 | Bucholz |
| 6,031,941 A | 2/2000 | Yano et al. |
| 6,050,943 A | 4/2000 | Slayton et al. |
| 6,100,531 A | 8/2000 | Hines et al. |
| 6,167,296 A | 12/2000 | Shahidi |
| 6,216,029 B1 | 4/2001 | Paltieli |
| 6,241,670 B1 | 6/2001 | Nambu |
| 6,353,227 B1 | 3/2002 | Boxen |
| 6,381,488 B1 | 4/2002 | Dickey et al. |
| 6,389,108 B1 | 5/2002 | Ein-Gal |
| 6,390,982 B1 | 5/2002 | Bova et al. |
| 6,392,235 B1 | 5/2002 | Barrett et al. |
| 6,405,072 B1 | 6/2002 | Cosman |
| 6,491,632 B1 | 12/2002 | Taylor |
| 6,540,679 B2 | 4/2003 | Slayton et al. |
| 6,628,984 B2 | 9/2003 | Weinberg |
| 6,754,596 B2 | 6/2004 | Ashe |
| 6,891,518 B2 | 5/2005 | Sauer et al. |
| 6,906,330 B2 | 6/2005 | Blevis et al. |
| 7,023,962 B2 | 4/2006 | Xu et al. |
| 7,035,897 B1 | 4/2006 | Devereaux et al. |
| 7,038,205 B2 | 5/2006 | Bushberg et al. |
| 7,102,138 B2 | 9/2006 | Belvis et al. |
| 7,142,905 B2 | 11/2006 | Slayton et al. |
| 7,166,846 B2 | 1/2007 | Engdahl et al. |
| 7,199,371 B2 | 4/2007 | Schramm et al. |
| 7,230,246 B2 | 6/2007 | Hawman |
| 7,250,607 B1 | 7/2007 | Keck et al. |
| 7,292,251 B1 | 11/2007 | Gu et al. |
| 7,345,282 B2 | 3/2008 | Hawman |
| 7,439,514 B1 | 10/2008 | Uribe et al. |
| 7,500,795 B2 | 3/2009 | Sandhu |
| 7,521,681 B2 | 4/2009 | Hawman |
| 7,549,961 B1 | 6/2009 | Hwang |
| 7,579,600 B2 | 8/2009 | Joung |
| 7,596,209 B2 | 9/2009 | Perkins |
| 7,606,861 B2 | 10/2009 | Killcommons et al. |
| 7,612,343 B2 | 11/2009 | Vickers |
| 7,652,259 B2 | 1/2010 | Kimchy et al. |
| 7,671,340 B2 | 3/2010 | Uribe et al. |
| 7,723,690 B2 | 5/2010 | Uribe et al. |
| 7,786,444 B2 | 8/2010 | Wagenaar et al. |
| 7,809,194 B2 | 10/2010 | Zhang et al. |
| 7,831,024 B2 | 11/2010 | Metzler et al. |
| 7,835,785 B2 | 11/2010 | Scully et al. |
| 7,894,078 B2 | 2/2011 | Gharib et al. |
| 7,912,733 B2 | 3/2011 | Clements et al. |
| 7,914,453 B2 | 3/2011 | Slayton et al. |
| 7,989,771 B2 | 8/2011 | Wieczorek et al. |
| 8,000,773 B2 | 8/2011 | Rousso et al. |
| RE42,952 E | 11/2011 | Hu et al. |
| 8,060,185 B2 | 11/2011 | Hunter et al. |
| 8,067,741 B2 | 11/2011 | Beekman |
| 8,090,429 B2 | 1/2012 | Vija et al. |
| 8,109,878 B1 | 2/2012 | Oruanaidh et al. |
| 8,153,986 B2 | 4/2012 | Mihailescu et al. |
| 8,195,417 B2 | 6/2012 | Feiweier et al. |
| 8,235,909 B2 | 8/2012 | Barthe et al. |
| 8,423,125 B2 | 4/2013 | Rousso et al. |
| 8,445,851 B2 | 5/2013 | Rousso et al. |
| 8,476,610 B2 | 7/2013 | Hawman et al. |
| 8,487,265 B2 | 7/2013 | Heukensfeldt et al. |
| 8,552,389 B2 | 10/2013 | Jansen et al. |
| 8,565,860 B2 | 10/2013 | Kimchy et al. |
| 8,594,769 B2 | 11/2013 | Mostafavi |
| 8,748,827 B2 | 6/2014 | Zilberstein et al. |
| 8,831,708 B2 | 9/2014 | Paladini |
| 9,014,340 B2 | 4/2015 | Kurochi |
| 9,040,925 B2 | 5/2015 | Giarmana et al. |
| 9,119,669 B2 | 9/2015 | Keglovich et al. |
| 9,129,422 B2 | 9/2015 | Mountney et al. |
| 9,146,198 B2 | 9/2015 | Wendler et al. |
| 9,263,160 B2 | 2/2016 | Kang et al. |
| 9,286,732 B2 | 3/2016 | Wendler |
| 9,344,700 B2 | 5/2016 | Zalevsky et al. |
| 9,345,441 B2 | 5/2016 | Wendler |
| 9,561,019 B2 | 2/2017 | Mihailescu et al. |
| 9,566,454 B2 | 2/2017 | Barthe et al. |
| 9,711,251 B2 | 7/2017 | Lee et al. |
| 9,743,898 B2 | 8/2017 | Wendler et al. |
| 9,903,962 B2 | 2/2018 | Kovalski et al. |
| 10,033,996 B2 | 7/2018 | Zalevsky et al. |
| 10,219,782 B2 | 3/2019 | Pandey et al. |
| 10,426,350 B2 | 10/2019 | Mihailescu et al. |
| 10,617,366 B2 | 4/2020 | Feng et al. |
| 10,617,401 B2 | 4/2020 | Mihailescu et al. |
| 10,795,036 B2 | 10/2020 | Boardman et al. |
| 10,869,611 B2 | 12/2020 | Ernst et al. |
| 2001/0056234 A1 | 12/2001 | Weinberg |
| 2002/0052709 A1 | 5/2002 | Akatsuka et al. |
| 2002/0087080 A1 | 7/2002 | Slayton et al. |
| 2003/0004413 A1 | 1/2003 | Inoue et al. |
| 2003/0047597 A1 | 3/2003 | Knowles et al. |
| 2003/0112922 A1 | 6/2003 | Burdette et al. |
| 2003/0128801 A1 | 7/2003 | Eisenberg et al. |
| 2003/0194050 A1* | 10/2003 | Eberhard .......... A61B 6/502 378/37 |
| 2003/0208117 A1 | 11/2003 | Shwartz et al. |
| 2004/0054248 A1 | 3/2004 | Kimchy et al. |
| 2004/0152975 A1 | 8/2004 | Blevis |
| 2005/0104881 A1 | 5/2005 | Yoshida et al. |
| 2005/0256406 A1 | 11/2005 | Barthe et al. |
| 2005/0271300 A1 | 12/2005 | Pina |
| 2005/0285844 A1 | 12/2005 | Morita et al. |
| 2005/0289472 A1 | 12/2005 | Morita et al. |
| 2006/0079764 A1 | 4/2006 | Wright et al. |
| 2006/0100509 A1 | 5/2006 | Wright et al. |
| 2006/0122617 A1 | 6/2006 | Lavallee et al. |
| 2006/0237652 A1* | 10/2006 | Kimchy .............. A61B 34/20 600/407 |
| 2007/0015987 A1 | 1/2007 | Benlloch et al. |
| 2007/0078334 A1 | 4/2007 | Scully et al. |
| 2007/0135984 A1 | 6/2007 | Breed et al. |
| 2007/0161884 A1 | 7/2007 | Black et al. |
| 2007/0167712 A1 | 7/2007 | Keglovich et al. |
| 2007/0205373 A1 | 9/2007 | Kornblau et al. |
| 2007/0223651 A1* | 9/2007 | Wagenaar .......... G01T 1/1611 378/37 |
| 2007/0225553 A1 | 9/2007 | Shahidi |
| 2007/0236514 A1 | 10/2007 | Agusanto et al. |
| 2008/0042067 A1* | 2/2008 | Rousso .............. A61B 5/417 250/363.04 |
| 2008/0051651 A1 | 2/2008 | Yamamoto et al. |
| 2008/0073543 A1* | 3/2008 | Vija .................. G01T 1/1611 250/370.08 |
| 2008/0084961 A1* | 4/2008 | Keppel .............. G06T 7/0012 382/128 |
| 2008/0086059 A1* | 4/2008 | Keppel .............. A61B 90/17 600/562 |
| 2008/0128626 A1* | 6/2008 | Rousso .............. A61B 6/4258 250/362 |
| 2009/0018403 A1 | 1/2009 | Black et al. |
| 2009/0078875 A1* | 3/2009 | Rousso .............. A61B 6/583 250/363.04 |
| 2009/0152471 A1* | 6/2009 | Rousso .............. G01T 1/161 250/363.04 |
| 2009/0209852 A1 | 8/2009 | Mate et al. |
| 2009/0259123 A1 | 10/2009 | Navab et al. |
| 2009/0306509 A1 | 12/2009 | Pedersen et al. |
| 2010/0016765 A1* | 1/2010 | Hall ................ A61B 6/037 250/363.04 |
| 2010/0183213 A1* | 7/2010 | Keppel .............. A61B 6/037 378/62 |
| 2010/0187425 A1* | 7/2010 | Majewski .......... G01T 1/1641 250/363.05 |
| 2010/0198068 A1 | 8/2010 | Rivaz et al. |
| 2010/0266171 A1* | 10/2010 | Wendler ............ A61B 6/037 382/128 |
| 2010/0268067 A1 | 10/2010 | Razzaque et al. |
| 2010/0268070 A1* | 10/2010 | Jaffer ................ A61B 5/0086 623/1.46 |
| 2010/0298704 A1 | 11/2010 | Pelissier et al. |

(56) References Cited

U.S. PATENT DOCUMENTS

| | | | |
|---|---|---|---|
| 2011/0007959 A1* | 1/2011 | Schulz | A61B 6/037 382/131 |
| 2011/0046483 A1 | 2/2011 | Fuchs et al. | |
| 2011/0098083 A1 | 4/2011 | Lablans | |
| 2011/0137156 A1 | 6/2011 | Razzaque et al. | |
| 2011/0144451 A1 | 6/2011 | Robertson | |
| 2011/0178373 A1 | 7/2011 | Pacey et al. | |
| 2011/0237945 A1 | 9/2011 | Foroughi et al. | |
| 2011/0306025 A1 | 12/2011 | Sheehan et al. | |
| 2012/0035462 A1* | 2/2012 | Maurer, Jr. | A61B 90/39 600/431 |
| 2012/0069167 A1 | 3/2012 | Liu et al. | |
| 2012/0128223 A1 | 5/2012 | Rivaz et al. | |
| 2012/0172699 A1* | 7/2012 | Nagler | G01T 1/1642 600/407 |
| 2012/0226150 A1 | 9/2012 | Balicki et al. | |
| 2012/0253200 A1 | 10/2012 | Stolka et al. | |
| 2012/0305812 A1 | 12/2012 | Bowen et al. | |
| 2013/0020493 A1 | 1/2013 | Ishii et al. | |
| 2013/0136302 A1 | 5/2013 | Nam et al. | |
| 2013/0158389 A1 | 6/2013 | OConnor | |
| 2013/0168570 A1 | 7/2013 | Wendler et al. | |
| 2013/0172739 A1 | 7/2013 | Paladini | |
| 2013/0229529 A1 | 9/2013 | Lablans | |
| 2013/0237811 A1 | 9/2013 | Mihailescu et al. | |
| 2013/0338490 A1 | 12/2013 | Wendler | |
| 2014/0042326 A1 | 2/2014 | Miyaoka et al. | |
| 2014/0142424 A1* | 5/2014 | Lail | A61B 6/12 600/436 |
| 2014/0151563 A1* | 6/2014 | Rousso | G01T 1/1603 250/362 |
| 2014/0163368 A1* | 6/2014 | Rousso | A61B 6/4258 600/436 |
| 2014/0175291 A1 | 6/2014 | Giarmana et al. | |
| 2014/0218720 A1* | 8/2014 | Kindem | A61B 5/0091 356/73 |
| 2014/0235921 A1 | 8/2014 | Wendler et al. | |
| 2014/0241600 A1 | 8/2014 | Mountney et al. | |
| 2014/0249402 A1 | 9/2014 | Kimchy et al. | |
| 2014/0343344 A1* | 11/2014 | Saunders | A61N 5/1049 600/1 |
| 2014/0350392 A1* | 11/2014 | Lundqvist | A61B 6/037 600/425 |
| 2014/0369560 A1 | 12/2014 | Wendler | |
| 2015/0065875 A1 | 3/2015 | Friebe | |
| 2015/0150525 A1 | 6/2015 | Navab et al. | |
| 2015/0238167 A1* | 8/2015 | Lail | A61N 5/1027 600/424 |
| 2015/0305700 A1 | 10/2015 | Wendler et al. | |
| 2016/0073976 A1 | 3/2016 | Moriyasu | |
| 2016/0135762 A1 | 5/2016 | Mihailescu et al. | |
| 2016/0242744 A1 | 8/2016 | Mihailescu et al. | |
| 2016/0253826 A9* | 9/2016 | Ziv | A61B 5/418 382/131 |
| 2016/0282432 A1* | 9/2016 | Wang | A61B 6/4417 |
| 2016/0287211 A1* | 10/2016 | DaCosta | A61B 8/48 |
| 2017/0112577 A1 | 4/2017 | Bonutti et al. | |
| 2019/0000318 A1* | 1/2019 | Caluser | A61B 5/0073 |
| 2020/0146641 A1 | 5/2020 | Mu | |
| 2020/0237321 A1 | 7/2020 | Feng et al. | |

FOREIGN PATENT DOCUMENTS

| | | |
|---|---|---|
| CN | 1805711 A | 7/2006 |
| CN | 101219061 A | 7/2008 |
| CN | 101561831 A | 10/2009 |
| CN | 101645170 A | 2/2010 |
| CN | 101719221 A | 6/2010 |
| CN | 101952837 A | 1/2011 |
| CN | 102258399 A | 11/2011 |
| CN | 102378594 A | 3/2012 |
| CN | 106659474 A | 5/2017 |
| CN | 104271046 B | 1/2018 |
| CN | 105708484 B | 8/2018 |
| DE | 10210648 A1 | 10/2003 |
| DE | 102008034579 A1 | 2/2010 |
| EP | 1795142 A1 | 6/2007 |
| EP | 1554987 B1 | 3/2009 |
| EP | 1269916 B1 | 3/2011 |
| EP | 1439780 B1 | 3/2011 |
| EP | 2045626 B1 | 6/2013 |
| EP | 2482101 B1 | 1/2014 |
| EP | 2310876 B1 | 3/2014 |
| EP | 2024761 B1 | 5/2014 |
| EP | 2165215 B1 | 5/2014 |
| EP | 2746815 A1 | 6/2014 |
| EP | 2073039 B1 | 8/2015 |
| EP | 2922471 A1 | 9/2015 |
| EP | 1554987 B2 | 12/2015 |
| EP | 2347285 B1 | 1/2019 |
| EP | 2949272 B1 | 3/2019 |
| JP | 2007282792 A | 11/2007 |
| JP | 2010200894 A | 9/2010 |
| NL | 2022634 B1 | 9/2020 |
| WO | 2004019799 A2 | 3/2004 |
| WO | 2006127142 A2 | 11/2006 |
| WO | 2007111570 A2 | 10/2007 |
| WO | 2007131561 A2 | 11/2007 |
| WO | 2011063266 A2 | 5/2011 |
| WO | 2011161197 A1 | 12/2011 |
| WO | 2013038011 A1 | 3/2013 |
| WO | 2013041720 A1 | 3/2013 |
| WO | 2013134559 A1 | 9/2013 |
| WO | 2014080013 A1 | 5/2014 |
| WO | 2017083611 A1 | 5/2017 |
| WO | 2020175985 A1 | 9/2020 |

OTHER PUBLICATIONS

International Search Report and Written Opinion dated Aug. 28, 2020; International Application No. PCT/US2020/027526; 15 pages.
Kaissas, I. et al., 3-D Localization of Gamma Ray Sources with Coded Apertures for Medical Applications, Journal of Physics: Conference Series, 637 (2015), 5 pages.
Laurent, P. et al., Collimators, Coded Masks and all Sky Monitors, Escole Astroparticules, 2016, 34 pages.
Moore, Richard H. et al, A Variable Angle Slant-Hole Collimator, The Journal of Nuclear Medicine, vol. 24, No. 1, 1983, pp. 61-65.
Ansar et al., "Linear Pose Estimation from Points of Lines", IEEE Transactions on Pattern Analysis and Machine Intelligence, May 2003, vol. 25(5), pp. 578-589.
Chiao et al., "Ocular Examination for Trauma; Clinical Ultrasound Aboard The International Space Station", The Journal of Trauma Injury, Infection and Critical Care, 2005, vol. 58(5), pp. 885-889.
De Cunha et al., "The MIDSTEP System for Ultrasound guided Remote Telesurgery", Proceeding of the 20th Annual International Conference of the IEEE Engineering in Medicine and Biology Society, 1998, vol. 20(3), pp. 1266-1269.
Fofi et al., "A comparative survey on invisible structured light", Proc. SPIE5303, Machine Vision Applications in Industrial Inspection XII, 90, May 2004, doi: 10.1117/12.525369; http://dx.doi.org/10.1117/12.52536.
Gat, "Imagining Spectroscopy Using Tunable Filters: A Review", Proc. SPIE, vol. 4056, Wavelet Applications VII, 50, Apr. 5, 2000, pp. 50-64.
Gee et al., "Sensorless freehand 3D ultrasound in real tissue: Speckle decorrelation without fully developed speckle", Medical Image Analysis, 10, 2006, 137-149.
Gibon et al., "Stereotactic Localization in Medical Imaging: A Technical and Methodological Review", Journal of Radiosurgery, 1999, vol. 2(3), pp. 167-180.
Goldsmith, "An Inertial-Optical Tracking System for Quantitative, Freehand, 3D Ultrasound", (thesis) Worcester Polytechnic Institute, Dec. 2008, 289 pages.
Goldsmith et al., "An Inertial-Optical Tracking System for Portable, Quantitative, 3D Ultrasound", IEEE International Ultrasonics Symposium Proceedings, 2008, pp. 45-49, doi:10.1109/ULTSYM.2008.0012.

(56) References Cited

OTHER PUBLICATIONS

Hansard et al., "Time-of-Flight, Principles, Methods and Applications, Springer Briefs in Computer Science", Springer Publications, Nov. 2012, 102 pages.

Kalman, "A New Approach to Linear Filtering and Prediction Problems", Journal of Basic Engineering, 82 (Series D): 35-45, 12 pages.

Lagrone et al., "A review of training opportunities for ultrasonography in low and middle income countries", Tropical Medicine and International Health, Jul. 2012, vol. 17(7), pp. 808-819.

Lepetit et al., "An Accurate O(n) Solution to the PnP Problem", International Journal of Computer Vision, 2009; vol. 81, pp. 155-166.

Lepetit et al., "EPnP: Accurate Non-Iterative O(n) Solution to the PnP Problem", Available Online At: https://upcommons.upc.edu/bitstream/handle/2117/10327/moreno_ijcv2009%20.pdf?sequence=1, Feb. 18, 2009, 22 pages.

Lu et al., "Fast and Globally Convergent Pose Estimation From Video Images", Feb. 18, 1998, 26 pages.

Mercier et al., "A Review of Calibration Techniques for Freehand 3-D Ultrasound Systems", Ultrasound in Med. & Biol., 2005, vol. 31(2), pp. 143-165, doi:10.1016/j.ultrasmedbio.2004.11.001.

Mercier et al., "New prototype neuronavigation system based on preoperative imaging and intraoperative freehand ultrasound: system description and validation", Int. J. Cars, 2011, 6:507-522, doi:10.1007/s11548-010-0535-3.

Mikulik et al., "Telemedicine-Guided Carotid and Transcranial Ultrasound: A Pilot Feasibility Study", Stroke, 2006, pp. 229-230, doi: 10.1161/0.1str.0000196988.45318.97, Downloaded from http://stroke.ahajournals.org/ at Lawrence Berkeley Lab on Jun. 30, 2012.

Mordohai et al., "Real-Time Video-Based Reconstruction of Urban Environments", University of North Carolina, Chapel Hill, NC, USA, 2007, 8 pages.

Nevatia et al., "Computer Aided Medical Diagnosis and Surgery System: Towards Automated Medical Diagnosis for Long Term Space Missions", 7 pages.

Ng et al., "Light Field Photography with a Hand-held Plenoptic Camera", Stanford Tech Report CTSR 2005-02, Apr. 2005, 11 pages.

Odell et al., "Next Generation, High Accuracy Optical Tracker for Target Acquisition and Cueing", 2006, 10 pages.

Prager et al., "Three-dimensional ultrasound imaging", Proc. IMechE, 2009, vol. 224 Part H: J. Engineering in Medicine, pp. 193-223.

Rafii-Tari, "Panorama Ultrasound for Navigation and Guidance of Epidural Anesthesia", A Thesis submitted in partial fulliment of the requirements for the degree of Master of Applied Science, The University of British Columbia, Vancouver, Sep. 2011, 99 pages.

Ren et al., "SAD based Sensor-less Freehand 3D Ultrasound Reconstruction with Adaptive Curve Correction", 2010, 10.1109/ICBBE 2010.5516742.

Sansoni et al., "State-of-the-Art and Application of 3D Imaging Sensors in Industry, Cultural Heritage, Medicine, and Criminal Investigation", Sensors, 2009, vol. 9, pp. 568-601.

Schneider et al., "Development and Testing of a New Magnetic-Tracking Device for Image Guidance", Proc. SPIE 6509, Medical Imaging, 2007: Visualization and Image-Guided Procedures, 65090I, Mar. 21, 2007; doi:10.1117/12.713249.

Sheehan et al., "Expert visual guidance of ultrasound for telemedicine", J Telemed Telecare, 2010, 16(2): 77-82.

Sheehan et al., "Tracking Three Dimensional Ultrasound with Immunity from Ferro-Magnetic Interference", LNCS, 2003, 2879, pp. 192-198.

Stolka et al., "Navigation with Local Sensors in Handheld 3D Ultrasound Initial in-vivo Experience", Proc. of SPIE, vol. 7968 79681J-1, downloaded from http://proceedings.spiedigitallibrary.org on Dec. 12, 2012, 9 pages.

Suenaga et al., "A Tele-instruction system for ultrasound probe operation based on shared AR technology", 2001 Conference Proceedings of the 23rd Annual International Conference of the IEEE Engineering in Medicine and Biology Society, 2001, 5 pages.

Takacs et al., "A Portable Ultrasound Guidance and Training System Using High Fidelity Virtual Human Models", Proceeding of the International Conference on Medical Information Visualization-MediVis'06, 2006, 5 pages.

Takacs et al., "Compact Anatomically Guided Ultrasound for Casualty Care", First International Conference on Advances in Computer-Human Interaction, IEEE, 2008, pp. 120-123.

Wang et al., "The Kinect as an interventional tracking system", Proc, of SPIE, vol. 8316 83160U-1, downloaded from http://spiedigitallibrary.org on Dec. 12, 2012.

Xiao-Shan et al., "Complete solution classification for the perspective-three-point problem", Pattern Analysis and Machine Intelligence, Aug. 2003, vol. 25, No. 8, pp. 930-942, IEEE Transactions on 2003:25:930-43.

Yu et al., "A 3D Freehand Ultrasound System for Multi-view Reconstructions from Sparse 2D Scanning Planes", BioMedical Engineering OnLine, 2011, 10:7, 22 pages.

Zhao et al., "Improved 3D Reconstruction Algorithm for Ultrasound B-scan Image with Freehand Tracker", Proceedings of SPIE, vol. 7629, Mar. 12, 2010, pp. 762914-1-762914-12.

* cited by examiner

3100

METHODS AND SYSTEMS FOR HIGH PERFORMANCE AND VERSATILE MOLECULAR IMAGING

CROSS-REFERENCE TO RELATED APPLICATIONS

The present application is a 371 U.S. national phase application of International Application No. PCT/US2020/027526, filed Apr. 9, 2020, which claims the benefit and priority of U.S. Application No. 62/831,504, filed on Apr. 9, 2019, entitled "Methods And Systems For High Performance Spect Imaging," and U.S. Application No. 62/836,514, filed on Apr. 19, 2019, entitled "Methods And Systems For Portable Spect And Ultrasound Imaging," the contents of which are herein incorporated by reference in their entirety for all purposes

FIELD OF THE INVENTION

This invention relates to the architecture of gamma cameras and their use along other co-registered medical imaging modalities, such as ultrasound systems, to enable new, high performance and versatile imaging systems for diagnostic imaging, guidance of medical intervention, such as percutaneous biopsies and ablation therapies, and for surgical guidance.

BACKGROUND

Single Photon Emission Computer Tomography (SPECT) by itself, or in combination with Computer Tomography (CT) (SPECT/CT), is a primary molecular imaging modality used for medical diagnostic imaging. Most commonly, SPECT imaging devices comprise an array of gamma-ray sensors that either surround the body of the patient, or orbit around the patient. During the imaging scan the patient most commonly lays on a table, and for some cardiac imaging systems, may sit on a custom built chair. Parallel hole collimators are commonly used in front of the detector array to constrain the direction gamma-ray photons can take before interacting with the position sensitive sensors. This creates parallel projections of the distribution of the gamma-ray emitting isotopes inside the patient. A computer program is used to reconstruct this distribution in 3D by using analytical or iterative image reconstruction algorithms.

Embodiments provide improved methods and systems for SPECT imaging.

BRIEF SUMMARY

Embodiments relate to systems and methods for Single Photon Emission Computer Tomography (SPECT) imaging.

Some embodiments provide a portable Single Photon Emission Computer Tomography (SPECT) imaging system to scan a patient. The system comprises a SPECT controller unit, where the controller unit includes a computer. The system further comprises a mechanical jointed arm connected to the controller unit. The jointed arm can be positioned to a desired location by a user through applying direct force. The system further comprises at least one gamma camera panel connected to the jointed arm. The gamma camera panel comprises gamma camera sensors with position and energy sensing resolution. The gamma camera panel may provide an imaging field of view that is larger than 15 degrees. The system further comprises a camera mounted in such a way as to observe an overall area of a patient. The system further comprises at least one processor and a memory operatively coupled with the at least one processor, the camera, and the gamma camera sensors. The memory has instructions for execution by the at least one processor that cause the at least one processor to read a first gamma-ray photon sensing event received from the gamma camera sensors. The processor further provides a first position and orientation of the gamma camera panel with respect to a body of the patient. The processor further co-registers the first gamma-ray photon sensing event to the body of the patient using the first position and orientation. The processor further reads a second gamma-ray photon sensing event received from the gamma sensors. The processor further provides a second position and orientation of the gamma camera panel with respect to the body of the patient. The processor further co-registers the second gamma-ray photon sensing event to the body of the patient using the second position and orientation. And the processor reconstructs a 3D distribution of gamma-ray emitting radioisotopes inside the patient by using first and second co-registered sensing events.

Some embodiments provide a real-time multi-modality portable Single Photon Emission Computer Tomography (SPECT) imaging system to scan a patient. The system comprises a SPECT controller unit, where the unit comprises a computer. The system further comprises a mechanical jointed arm connected to the controller unit, where the jointed arm can be positioned to a desired location by a user through applying direct force. The system further comprises at least one gamma camera panel connected to the jointed arm. The gamma camera panel comprises gamma camera sensors with position and energy sensing resolution. The system further comprises an ultrasound probe positionable in such a way as to have a field of view that at least partially overlaps with the gamma camera field of view. The system further comprises a tracking system able to provide information about the relative position of the ultrasound probe with respect to the gamma camera. The system further comprises a visualization device. The system further comprises at least one processor and a memory operatively coupled with the gamma camera sensors, ultrasound probe, tracking system and visualization device. The memory has instructions for execution by the at least one processor that cause the at least one processor to read a first gamma-ray photon sensing event received from the gamma sensors. The processor further executes the instructions to read a second gamma-ray photon sensing event received from the gamma sensors. The processor further executes the instructions to reconstruct a 3D distribution of gamma-ray emitting radio-isotopes inside the patient by using first and second sensing events. The processor further executes the instructions to determine a co-registration between the ultrasound probe and the gamma sensors using the tracking information. The processor further executes the instructions to determine a co-registration between the 3D distribution of gamma-ray emitting radioisotopes and an ultrasound scan using the co-registration between the ultrasound probe and the gamma sensors. The processor further executes the instructions to deliver to the visualization device an image that comprises an augmentation of the 3D distribution of gamma-ray emitting radioisotopes onto the ultrasound scan by using the co-registration between the 3D distribution of gamma-ray emitting radioisotopes and an ultrasound scan.

Some embodiments provide a portable Single Photon Emission Computer Tomography (SPECT) imaging system to scan a body part of a patient. The system comprises a SPECT controller unit, where the unit comprises a computer.

The system further comprises a mechanical jointed arm connected to the controller unit. In some embodiments the jointed arm can be mounted on other objects, such as on the floor, ceiling, walls, rails, and other fixed objects, instead of being mounted on the controller unit. The system further comprises at least a gamma camera panel connected to the jointed arm, where the gamma camera panel comprises gamma camera sensors with position and energy sensing resolution. The gamma camera panel provides an imaging field of view that is larger than 15 degrees. The imaging field of view can be defined as the range of angles off the direction at which the gamma camera has maximum imaging sensitivity, and from which gamma photons can be detected and imaged by gamma sensors comprised by the gamma camera panel with a sensitivity larger than a hundredth the maximum imaging sensitivity. The system further comprises a tactile pressure sensor mounted on the panel. The tactile pressure sensor is operationally coupled to at least one processor and memory. The movement of the panels with respect to the patient is modified depending on the tactile pressure sensor data.

In some embodiments, the portable SPECT system uses data from an external computer tomograph (CT), or another medical imaging scanner (such as Magnetic Resonance Imaging) to improve the delivered molecular image quality by applying attenuation corrections. In some embodiments, the CT images can be co-registered with the molecular images and a rendering of their combination may be sent to a visualization device for user interpretation. In some embodiments, the co-registration between the CT images and SPECT images may be done by matching the 3D outline of the patient. A co-registered ultrasound image may be used to help the co-registration. In some other embodiments a tag may be used for co-registration.

In some embodiments, the portable SPECT system may be co-registered with medical optical imaging devices, such as endoscopes, laparoscopes, or with x-ray devices, such as fluoroscopes, to guide medical interventions, such as biopsies, ablations, or surgeries.

In an exemplary embodiment, a system comprises a gamma-ray photon sensor with energy and position resolution sensing capability. The gamma-ray photon sensor can provide positions of photon interactions. The system further comprises a coded aperture mask placed in front of the photon sensor. The mask can comprise photon attenuating mask pixel elements shaped as bifrustums where a physical space between bifrustum mask pixel elements that have a common edge is partially or completely occupied by a material. The mask can create an imaging field of view in front of the sensor. The system further comprises at least one processor and a memory operatively coupled with the sensor and the processor. The memory can store instructions for execution by the at least one processor that cause the processor to project a position of a first photon interaction onto a plane of reference to create a first projected interaction point. The processor can also retrieve photon attenuation coefficients stored in the memory for the first projected interaction point for directions towards the imaging field of view. The processor can also project the position of a second photon interaction onto a plane of reference to create a second projected interaction point. The processor can also retrieve photon attenuation coefficients stored in the memory for the second projected interaction point for directions towards the imaging field of view. The processor can also reconstruct an image of a gamma-ray source using the retrieved attenuation coefficients for the first and second photon interactions.

In some embodiments, the sensor provides the position of the photon interaction with resolution better than 4 millimeters (mm) in all three dimensions. In some embodiments the coded aperture mask is made out a material of density higher than 10 grams per cubic centimeter (g/cc). In some embodiments, mask pixel elements are shaped as bifrustums that have at least a side face making an angle larger than 3 degrees with respect to the normal on the bifrustum base. In some embodiments, mask pixel elements are shaped as bifrustums that have at least a side face making an angle larger than 5 degrees with respect to the normal on the bifrustum base In some embodiments, the material between bifrustum mask pixel elements is of density higher than 10 g/cc. In some embodiments, the bifrustum mask pixel elements have a base selected from a group containing: a rectangular base, a triangular base, a hexagonal base. In some embodiments, the shape of bifrustum mask pixel elements is approximated by mask pixel elements with curved side faces. In some embodiments, the coded aperture mask expands across multiple planes. In some embodiments, the system further comprises photon attenuating shields at directions around the sensor not covered by the coded aperture mask. In some embodiments, the coded aperture mask has an opening fraction, defined as fraction of the area of the of non-attenuating mask area to the total area of the mask, to span from 0.1% to 70%. In some embodiments, the coded aperture mask is self-supporting. In some embodiments, the coded aperture mask is built of multiple layers stacked together to approximate the bifrustum shaping of the mask pixels.

In another exemplary embodiment, a method includes projecting a position of a first photon interaction detected by a gamma-ray photon sensor onto a first plane of reference to create a first projected interaction point. In this embodiment, the gamma-ray photon sensor has energy and position resolution sensing capability. The gamma-ray photon sensor provides the position of photon interactions. In this embodiment, a coded aperture mask is placed in front of the photon sensor. The mask comprises photon attenuating mask pixel elements shaped as bifrustums. In the mask, a physical space between bifrustum mask pixel elements that have a common edge is partially or completely occupied by a material. The mask creates an imaging field of view in front of the sensor. The method further includes retrieving photon attenuation coefficients stored in the memory for the first projected interaction point for directions towards the imaging field of view. The method further includes projecting a position of a second photon interaction detected by the gamma-ray photon sensor onto a second plane of reference to create a second projected interaction point. The method further includes retrieving photon attenuation coefficients stored in the memory for the second projected interaction point for directions towards the imaging field of view. The method further includes reconstructing an image of a gamma-ray source using the retrieved attenuation coefficients for the first and second photon interactions.

In some embodiments, the mask used in front of the sensors to code incident gamma-ray photons has an adjustable geometry. The adjustments can be induced by a computer sending instructions to actuators. The adjustments allow the mask to provide both large and narrow field of views. This allows large field of view scanning, and narrow focused on structures of interest, when needed. Moreover, the adjustments may change the distance between the mask to the detectors. Moreover, the adjustments may change the opening fraction of the mask. In some embodiments the mask can be made of overlapping parallel plates with openings that partially or totally overlap. In an embodiment, the mask is made of 3 overlapping layers, but any number of layers can be envisioned. In an embodiment, the layers move away from each other to increase the focusing power, or the collimation. In some implementations the computer controls the arrangement of the mask elements depending on an imaging task, or depending on a user input.

In some embodiments, the portable SPECT system may be used both in scanning mode, to create a more extended SPECT image dataset, and in real-time imaging mode, to create actionable images. An adjustable mask may be used to optimize these imaging modes, by allowing both large field of view imaging, especially useful for scanning, and narrow field of view, particularly useful for real-time imaging of specific structures.

A better understanding of the nature and advantages of embodiments may be gained with reference to the following detailed description and the accompanying drawings.

DETAILED DESCRIPTION

Figure 1:
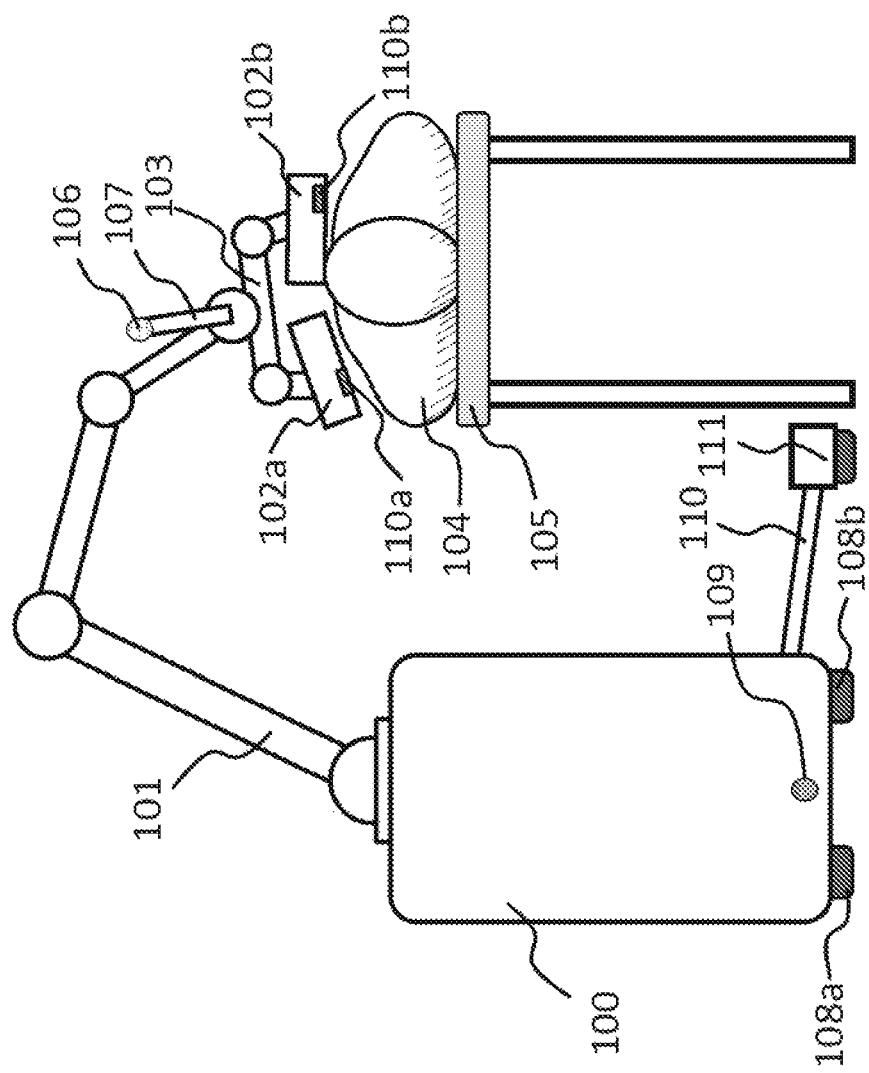
FIG. 1 shows a view of a portable SPECT imaging system actuated by a jointed arm.

Single Photon Emission Computer Tomography (SPECT) by itself, or in combination with Computer Tomography (CT) (SPECT/CT), is a primary molecular imaging modality used for medical diagnostic imaging. Most commonly, SPECT imaging devices comprise an array of gamma-ray sensors that either surround the body of the patient, or orbit around the patient. During the imaging scan the patient most commonly lays on a table, and for some cardiac imaging systems, may sit on a custom built chair. Parallel hole collimators are commonly used in front of the detector array to constrain the direction gamma-ray photons can take before interacting with the position sensitive sensors. This creates parallel projections of the distribution of the gamma-ray emitting isotopes inside the patient. A computer program is used to reconstruct this distribution in 3D by using analytical or iterative image reconstruction algorithms.

The sensors and associated collimators may be placed at relatively long distances from the patient so that patients of various sizes can be accommodated. Since the SPECT imaging sensors are characterized by a finite angular resolution, this larger standoff distance between said sensors and the radioisotope-tagged molecules may translate into lower imaging resolution and sensitivity. A reduced standoff distance would lead towards an increased sensitivity and resolution. Certain SPECT imaging systems comprise sensors that can be actuated to reduce the standoff distance to the body. Such systems may use parallel hole collimators that change direction to capture projections at various angles. As such, the standoff distance between the body of the patient and the sensor may be reduced, which can improve performance.

Computer Tomography (CT) may be used in conjunction with SPECT imaging to provide 3D morphological context to the molecular image provided by SPECT. By the co-registration of the two 3D maps, radiologists can identify the organs where increased radio-agents have increased uptake. Moreover, the CT map can achieve a more accurate reconstruction of the SPECT map by providing a photon attenuation map that allows the SPECT image reconstruction algorithm to account for photon attenuation between the image voxels to the SPECT imaging sensors.

Embodiments comprise an improved SPECT imaging device that is portable and allows co-registration with ultrasound. The SPECT imaging device described herein can be used to guide medical interventions, such as biopsies and ablation therapies, and can also be used to guide surgeries. This improved SPECT imaging device also provides co-registration with other medical imaging modalities, such as x-ray, CT, and various optical imaging modalities.

Among other aspects, the SPECT imaging device described herein provide portable high imaging performance molecular imaging using molecular agents labeled with SPECT radioisotopes. The SPECT imaging device described herein provides new multimodality imaging systems and corresponding methods that combine SPECT imaging with ultrasound imaging and other medical imaging modalities to enable multiple medical uses, such as diagnostic imaging, biopsy guidance, ablation therapy guidance, surgical guidance.

These and other advantages of one or more aspects will become apparent from a consideration of the ensuing description and accompanying drawings.

Portable SPECT imaging systems and associated methods can provide imaging of radiotracer distributions inside a body of a patient with high resolution and sensitivity by employing at least a specifically designed gamma camera panel mounted on a jointed mechanical arm. In some embodiments, the gamma camera panel utilizes a gamma photon imaging modality that provides a distance from the gamma camera to a gamma radiotracer location even when the gamma camera scans the patient from an essentially static location. In some embodiments, the jointed mechanical arm is a 6 axis robotic arm. In some embodiments, the jointed mechanical arm is be actuated by a user by either applying direct force or through the use of a computer. In some embodiments, the robotic arm can be actuated by a computer to perform an automated specific examination of a patient, such as a whole body scan, a head scan, a neck scan, a cardiac scan, a torso scan, and so forth. For navigation purposes, a computer vision system can be used to provide information with respect to the location and position of a patient, create a 3D model of the patient body, and to identify specific body parts. A tracking system may be used to determine the position of SPECT system components with respect to each other and with respect to the patient. The 3D model of the patient can be combined with the tracking information to guide the SPECT scan. In some embodiments, the SPECT system may be placed on motorized wheels, and these wheels may be actuated during the scan to extend the reach of the gamma camera panels around the patient.

Embodiments further include multimodality imaging systems and methods that co-register portable SPECT imaging systems with other imaging modalities. In embodiments, ultrasound probes and corresponding ultrasound images are co-registered with the portable SPECT imaging system using tracking systems to enable molecular image combined with ultrasound image guidance of medical interventions, molecular imaging with correction for tissue deformation, and molecular image guided ultrasound examinations. In embodiments, the portable SPECT imaging system comprises two physically separated gamma camera panels that can be actuated to leave a space between them and to be orientated at various angles with respect to each other. In yet another embodiment, another imaging probe, such as an ultrasound probe, is placed essentially between the two gamma camera panels, and the imaging field of view of at least a gamma camera panel and the other medical imager overlap. This embodiment allows a user to visualize SPECT images co-registered to ultrasound images in real time. Other medical instruments may be placed in the space between the two panels. Examples of such medical instruments are percutaneous biopsy devices and ablation therapy devices. The use of these instruments may be guided by the SPECT and/or ultrasound image.

The presented portable multimodality imaging SPECT and ultrasound systems and methods can provide several advantages over prior multimodality SPECT/CT and PET/CT systems, among which: elimination of radiation dose associated with CT by providing ultrasound delivered co-registered anatomical information, portability conferred by the much smaller robotic SPECT and ultrasound systems, increased molecular imaging resolution and sensitivity by performing imaging scans with the gamma camera panel placed much closer to the body of the patient, precise and straightforward guidance of medical interventions, employment in the operating room to guide surgeries, improvement of the molecular image quality by using real-time ultrasound to guide molecular image corrections that account for tissue deformations and organ movements captured by the ultrasound transducers.

Among other aspects, embodiments of said portable SPECT imaging system and associated methods also allow for scanning of the patient from a limited range of angles around the patient without loss in imaging performance. This advantage over prior systems is provided by an embodiment in which the gamma camera panel provides imaging resolution in the direction normal onto the face of the gamma camera panel from an essentially static location. This advantage is also provided by an embodiment in which the gamma camera panel provides an imaging field of view larger than 15 degrees, preferably close to 45 degrees. An imaging field of view is defined as the range of angles at least in one direction off the normal of the gamma camera panel from which gamma photons can be detected by gamma sensors comprised by the gamma camera panel and imaged. A scanning of the patient from a limited range of angles, whereas normally not preferable, may be imposed by various operational and specific imaging task constraints, such as a requirement for a reduced scanning time, limited physical access of imaging sensor panels around the patient, or increased attenuation or attenuation inhomogeneity of radiation at some directions around the patient that may contribute to increased imaging artifacts.

Image co-registration between said portable SPECT system, other medical imaging modalities and medical instruments can be achieved by using position tracking systems that capture the relative position of the gamma sensor, other medical imaging sensors, such as ultrasound transducers, and medical instruments with respect to each other and with respect to the body of the patient. A range of position tracking systems can be used by themselves or in combination. Such position tracking systems can use inertial measurement units (IMU), optical systems, such as RGB cameras, depth imaging sensors, infrared cameras, stereoscopic optical systems, electromechanical jointed arms, electromagnetic field trackers, ultrasound trackers, servo motors, or any other device suitable to provide position and orientation of components of interest with suitable precision.

In some embodiments, the gamma camera panel comprises a gamma photon attenuating imaging component placed in front of a position sensitive gamma-ray sensor. The photon attenuating imaging component can be selected from a group containing a coded aperture mask, a straight and/or slant parallel hole collimator, a pinhole collimator or a multipinhole collimator. In a preferred implementation, the gamma ray sensor provides the location of the gamma photon interaction with a resolution better than 2 millimeters (mm) in all three dimensions. In some embodiments, the photon attenuating imaging component is a coded aperture mask with a field of view larger than 20 degrees. Preferably, the pattern of the coded aperture mask minimizes the side lobes in the instrument autocorrelation function. (See, e.g., Fenimore, Edward E., and Thomas M. Cannon. "Coded aperture imaging with uniformly redundant arrays." *Applied optics* 17.3 (1978): 337-347). Patterns that repeat at different translations, without rotations or reflections, are advised against, as they may create peaks in the side lobes of the autocorrelation function for a magnification of interest, leading to reconstruction artifacts. Likewise, openings that create straight long slits, especially multiple straight long slits parallel to each other, that may be as long as the essentially the mask width, or as long as a significant part of the mask width may create image artifacts for this application. The coded aperture pattern can have an opening fraction, defined as the ratio of empty mask pixels to the total number of pixels, that ranges from close to 0% to close to 100%. In some embodiments, the opening fractions may range from 0.1% to around 80%. In some embodiments, the opening fraction may range from 5% to 30%. Such opening fraction may maximize the image signal-to-noise ratio for certain distributions of molecular SPECT agents in humans. In some embodiments, an adjustable mask may deliver a range of opening fractions, such as from 5% to 70%, by adjusting mask elements. For example a mask comprising overlapping layers with overlapping or partially overlapping openings (holes) can deliver such adjustability by having the layers move laterally with respect to each other. Other assembly of mask elements can create the same effect.

In some SPECT imaging systems, the sensors and associated collimators may be placed at relatively long distances from the patient so that patients of various sizes can be accommodated. Since the SPECT imaging sensors are characterized by a finite angular resolution, this larger standoff distance between said sensors and the radioisotope-tagged molecules may translate into lower imaging resolution and sensitivity. A reduced standoff distance may lead towards an increased sensitivity and resolution. Certain SPECT imaging systems comprise sensors that can be actuated to reduce the standoff distance to the body. Such systems may also comprise parallel hole collimators that change direction to capture projections at various angles. As such, the standoff distance between the body of the patient is reduced and the sensor performance is improved.

Embodiments include an alternative imaging and sensing modality that allows the imaging sensor assembly to be in even closer proximity to the body of the patient while properly sampling the image space in order to provide even higher image sensitivity and resolution in 3D. These techniques eliminate the need for taking sensor data uniformly around the patient by allowing efficient sampling of multiple projection angles from a reduced (tomographic) range of angles around the patient.

Among other aspects, embodiments allow for the construction of a high resolution 3-dimensional map of radioisotope distributions inside a patient by scanning the patient from a reduced range of directions around said patient and with radiation sensors placed in close proximity to this patient. This leads to increased imaging sensitivity and resolution. Thus, several advantages of one or more aspects are to enable SPECT imaging with high resolution and high efficiency through the employment of compact SPECT imaging sensors and systems that can be made portable, or even handheld.

Among other aspects, embodiments include imaging systems and associated methods that enable imaging of radiotracer distributions inside a body of a patient with high resolution and sensitivity in 3 dimensions (3D) by using a sensor assembly that scans the patient from locations in close proximity to the patient and from directions that may only cover a limited range of angles around the patient. Sensor proximity to the patient may be used because it may allow for better imaging resolution, and in some instances, such as in the current approach, better imaging sensitivity. A scanning of the patient from a limited range of angles, whereas normally not preferable, may be imposed by various operational constraints, such as a limited scanning time, limited physical access of imaging sensors around the patient, or increased attenuation or attenuation inhomogeneity of radiation at some directions around the patient that may contribute to increased imaging artifacts.

A key prerequisite of such a sensing imaging system is a large imaging field of view in order to overcome scanning of the patient from a limited range of directions. At the same time, it is important for this imaging system to provide high imaging resolution and high sensitivity, which previously required a narrow field of view.

Embodiments enable SPECT imaging with an imaging sensor that provides both large imaging field of view and high imaging resolution and sensitivity. This imaging sensor comprises a custom designed, large field-of-view radiation attenuating mask placed in front of a radiation position sensitive sensor, and a processing unit that allows image reconstruction techniques that are efficient and effective resulting in reconstructed images of superior image resolution, signal-to-noise ratio (SNR) and sensitivity. For imaging gamma-ray photons, the attenuating mask may be made of a high density, high atomic number Z material, such as tungsten, tungsten alloy, etc.

In some embodiments, the mask can be a coded aperture mask with the coding elements shaped in such a way to allow large field of view imaging. The coded aperture pattern contains a combination of radiation attenuating pixels and empty, non-attenuating pixels. In this description the attenuating pixels will be referred as mask pixels and the non-attenuating pixels as empty mask pixels. Examples of coded aperture patterns that can be used in the mask are: a uniformly redundant array, a modified uniformly redundant array, a pseudo-random array, a random array or any other pattern. In some embodiments, the coded aperture pattern minimizes the side lobes in the instrument response function. The coded aperture pattern can have an opening fraction, defined as the ratio of empty mask pixels to the total number of pixels, that ranges from close to 0% to close to 100%. However, most useful opening fractions may range from a fraction of 1% to around 50%.

In order to properly attenuate gamma-ray photons of 120 keV-170 keV, which correspond to the specific gamma-ray energies of many SPECT isotopes, the attenuating mask may need to have a thickness that is in the same range as the size of the mask elements, if not larger. For example, manufacturing the mask from a tungsten alloy, a mask thickness of around 2 mm may be used to attenuate 140 keV photons, which may be in the same range as the size of the mask pixel elements.

Using mask pixel elements shaped as rectangular parallelepipeds—that is with straight side edges and single planar side faces for each Cartesian direction in the mask plane provides poor performance; proper coding contrast can only be achieved for photons of low incident angles of up to 10-20 degrees from the normal on the mask plane, when assuming single plane mask and square shaped mask pixels. Because of this limitation of rectangular parallelepiped mask pixels, embodiments provide a customized shaping of the mask pixel elements.

In some embodiments, the sides of the pixel elements are designed using customized geometries. These customized geometries include non-straight side edges and multiple planar side faces for each of the two Cartesian directions orthogonal to the mask plane in a traditional mask. Curved side faces can also be used instead of multiple planar side faces.

The sides described above can be combined with varying geometries of mask pixel elements such as: square, triangle and hexagon pixels, in which each of the side faces of the triangular or hexagonal prisms can contain multiple planar faces or curved side faces. These geometries may provide image coding with high contrast for radiation photons in a large range of incident angles with respect to the normal of the mask plane. For example, such incident angles can reach 50 degrees from the normal to the mask plane, if not more. Thus, the customized shaping of the mask elements within a single mask may combine edges, ridges and curvatures of various geometries and orientations.

In some particular embodiments, the square or rectangular mask pixel elements in a mask array can be built of a bifrustum (or bipyramid) with a square or rectangular base, for example. The bifrustum may be symmetric with respect to the center of the rectangular base, may be symmetric with respect to the rectangular base plane, or may not have such symmetries. The shape of the bifrustum mask elements may change across the mask. When two mask pixels have a common edge, the space between the two adjacent bifrustums may be filled with attenuating material. Instead of planar side faces, curved side faces can be used to approximate the shape of the bifrustum. Likewise, multiple thin layers of mask can be stacked together to approximate the shape of the bifrustum mask elements and the fill material between adjacent bifrustums.

Bifrustums with a triangular or hexagonal base can be used for mask pixel elements that are triangular or hexagonal, respectively. The bifrustum may be symmetric with respect to the center of the triangular or hexagonal base, may be symmetric with respect to the triangular or hexagonal base plane, or may not have such symmetries. The shape of the bifrustum mask elements may change across the mask. Fill attenuating material can be used in this case as well between mask elements that share a common edge.

The mask can be arranged within a plane or within multiple planes that may or may not be parallel to each other. A shield may be used to cover parts of the space around the sensors that are not covered by the coded aperture mask to limit the detection of photons from other angles that are not covered by the coded aperture.

In order to deliver better imaging resolution, the position sensitive sensor may capture all three coordinates of a radiation interaction inside the sensor with high resolution, such as with a resolution better than 1 or 2 mm in all 3 dimensions. Moreover, the sensors may provide radiation detection with high energy resolution, since this may allow for a superior selection of events that have not scattered before reaching the mask and sensor. Such sensors can be scintillators, semiconductors, or other types of radiation detectors that are able to provide the position of radiation interactions.

In order to reconstruct the 3D distribution of radioactive molecules, an image reconstruction analysis package is used to process the sensor data. In a particular implementation, an attenuation map is pre-calculated to associate sensor location with a distribution of incident gamma-ray photon angles. This distribution is weighted by the probability of these photons to have traversed the coded mask. The described detail of the sides of each mask pixel adds to the information bandwidth of the mask coding. As such, the attenuation map may be complex and can be pre-computed by using high resolution ray-tracing and/or Monte Carlo simulations. In a particular implementation, an attenuation map is pre-calculated across at least a plane referred to as a plane of reference. For each point within the plane of reference, the attenuation map comprises attenuation coefficients, or other information that can be used to extract the attenuation coefficients, such as path lengths through the mask material, for a pre-defined type of radiation, and for various angles across the imaging field of view. The calculation of the attenuation map may use ray tracing methods, simulation methods, such as Monte Carlo simulation methods, or a combination of these, to determine the radiation path through the shielding and mask assembly from various origin-angles across the field of view. For a specific type of radiation, the attenuation factors can then be calculated from the path values.

For each radiation detected by the radiation sensor, the 3D position of the interaction is first projected onto the reference plane using various sampling techniques. The sampling is focused on directions towards the coded mask field of view, and that projected position onto the reference plane is used to determine the attenuation coefficient through the mask along those directions. If the path of the photon along a certain direction can include a segment through the sensor or other material not captured by the pre-calculated attenuation coefficients, additional attenuation computations can be added in to properly scale the intensity of the backprojection along that direction. The backprojection process can determine the probability density function (pdf) for a detected event or for a detected intensity in a bin. The pdf for at least two detected radiation events can be used in any suitable iterative or analytic image reconstruction algorithm known in the field. The image reconstruction analysis can be performed in a list mode or in a binned mode. If the analysis is performed in a binned mode, the binning may be performed across multiple planes, and each detected photon can be added onto the plane that is closest in space.

In some implementations, the attenuation coefficients could also be calculated during the image reconstruction analysis on-the-fly, by using fast path estimators, such as ray tracing methods. However, a precomputation of these coefficients may provide the best image reconstruction processing speed performance.

FIG. 1 shows a depiction of a portable SPECT imaging system comprising a mechanical jointed arm, such as a robotic arm. An instrument controller (100) is connected through a mechanical jointed arm (101) to at least a gamma camera panel. In the depicted embodiment two gamma camera panels (102a) and (102b) are used. The panels (102a) and (102b) may be attached to each other and to the jointed arm through a jointed lever (103). This jointed lever may allow for the two panels to move with respect to each other and with respect to the jointed arm, as well as may allow the panels to change their relative orientation, particularly their roll, but also their pitch and yaw. Accordingly, the relative angle between the panels can be modified. A computer vision camera (106) could be attached to the jointed arm (101), to the lever (103), or to another component connected to the portable SPECT system through a connector (107). This computer vision camera (106) may be used to monitor the overall area where the gamma camera panels are scanning the patient. This computer vision camera may comprise a RGB camera, an optical camera, an infrared camera, a depth imaging optical camera, a structured light camera, a stereoscopic optical camera, a time-of-flight optical camera, a terahertz emitter-sensor assembly, a lidar scanner, an ultrasound emitted-sensor assembly, another tracking and/or mapping sensor, or a combination thereof. The purpose of this camera is to determine the extent of the body of the patient so that the movement of the gamma camera panels will not collide with the body of the patient. In some embodiments an ultrasonic scanner or an electromagnetic scanner, such as a terahertz imaging scanner, could be used in addition, or instead of an optical camera to scan the outline of the patient's body.

Using such a portable SPECT imaging system, a scanning of the patient can be performed by having instructions in a memory of a computer operationally coupled to actuated components, such as the robotic arm (101), the lever (103), as well as gamma sensors comprised by the gamma cameras (102a) and (102b), and computer vision camera (106) to: read and analyze computer vision camera data to determine the outline of the patient's body and to determine the relative position and orientation of the computer vision camera (106) with respect to the body of the patient, articulate arm (101) and lever (103) so that the gamma camera panels (102a) and (102b) are moved at relevant locations around the patient, acquire data from the sensors comprised by the gamma cameras (102a) and (102b), spatially register the gamma sensor data with respect to the body of the patient, and use the spatially registered sensor data to create a 3D image of the radiotracer distribution inside the body of the patient. Gamma sensors provide the position within the sensor and energy of gamma photon interactions with high resolution. Preferably, the gamma sensor provides the position of the gamma event interactions in 3D with resolution better than 2 mm, ideally with resolution better than 0.5 mm.

In some embodiments, the controller may comprise wheels (108a) and (108b). In such embodiments the memory may be operationally coupled to at least a motor that actuates wheels (108a) and (108b), to move the controller (100). This can allow the system to scan larger areas over longer distances than otherwise would be allowed by the jointed arm (101). For navigation purposes and to avoid obstacles, other sensors (109) can be placed at one or either end of the controller to insure there are no obstacles in the path of the system. In such embodiments, the memory will be also operationally coupled to the sensor (109) to guide the actuation of the wheels (108a) and (108b). The sensor (109) can be an optical sensor, a lidar scanner, a depth imaging sensor, an ultrasonic sensor, or any other sensor that can detect obstacles.

In some embodiments, the panels (102a) and (102b) may comprise proximity sensors (110a) and (110b) placed preferably on the panel surface facing the patient to get information about proximity between the panels and the body of the patient or between the panels and other objects. The sensors (110a) and (110b) may be part of the computer vision system, and may be able to provide a 3D model of the patient's body just below the sensor panel in real time. This map may be used by the computer to adjust the movement of the scanners across the body of the patient and to provide estimates of the attenuation map used in the image reconstruction process. These proximity sensors may be operationally coupled to a computer that is also connected to actuators that move the panels with respect to the patient. The computer may use a program to change the scanning process or to stop the scanning process in order to keep the distance between the panels and the patient or other objects within a desired range of distances. Proximity sensors can be capacitive, inductive, magnetic, ultrasonic, optical, terahertz, X-ray backscatter, or any other sensor able to provide distance to objects.

In some embodiments the mechanical jointed arm (101) may be actuated by a user. In such cases, the purpose of the jointed arm is to support the weight of the gamma camera panels (102a) and (102b), and potentially to determine the position and orientation of the panels with respect to the body of the controller (100). Moreover, in some embodiments the articulations comprised by the lever (103) may be actuated by a user in order to manually position the gamma camera panels at locations and orientations desired by the user. In some embodiments, the user may actuate arm (101) and lever (103) through the application of direct force. In some embodiments, the user may actuate arm (101) and lever (103) through a computer operationally coupled to motorized actuators mechanically connected to the arm (101) and lever (103).

A computer comprising at least one processor and a memory operatively coupled with the computer vision camera (106) and gamma camera sensors comprised by gamma camera panels (102a) and (102b) can be used to read gamma sensor data and computer vision camera data to respectively: read a first gamma-ray photon sensing event received from the gamma sensors, provide a first position and orientation of the gamma camera panel (102a) or (102b) sensing first photon with respect to the body of the patient (104), co-register the first gamma-ray photon sensing event to the body of the patient (104) using the first position and orientation, read a second gamma-ray photon sensing event received from the gamma sensors, provide a second position and orientation of the gamma camera panel with respect to the body of the patient (104), co-register the second gamma-ray photon sensing event to the body of the patient (104) using the second position and orientation, and reconstruct a 3D distribution of gamma-ray emitting radioisotopes inside the patient by using first and second co-registered sensing events.

The co-registration of a sensing event to the body of the patient can be done by analyzing an computer vision camera frame with computer vision methods known in the field to determine a pose estimate of the computer vision camera (106) pose with respect to the body of the patient. Moreover, the relative position and orientation between the camera and the gamma camera panels (102a) or (102b) can be achieved by either direct observation of the panels by the camera (106), or by getting joint status information for the joints in lever (103), and/or potentially jointed arm (101). A combination of the two relative poses (computer vision camera-patient and computer vision camera-sensing gamma camera panels) can be combined to obtain the co-registration of the sensing event to the body of the patient. Other tracking and co-registration systems and methods may be used, some of which are described elsewhere in this description.

The computer vision camera frame data may be regularly analyzed during a SPECT scan by the computer vision program to create an updated 3D model of the body of the patient. By monitoring changes from one frame to another, it will be possible to detect changes in the body poses and body deformations. These detections may be used to improve the quality of the reconstructed SPECT images by accounting for such body changes, may be used to stop the scanning process to avoid collisions between any components of the SPECT imaging system with the patient or other users, or may inform the user of a significant body change that may require a reset of the SPECT scan.

As such, a computer connected to the camera (106) may employ computer vision methods to create at regular intervals 3D models of the body of the patient and to detect body changes and deformations taking place from one 3D model of the body to another. By analyzing the amplitude and type of body changes, the computer may inform the user of a significant body change that may require a reset of the SPECT scan, since the co-registration between detected events taking place before and after the body modifications may not be reliable.

Moreover, the computer may also be operationally coupled to the gamma camera sensors, and may determine and assign a first 3D patient body model to a first sensor detection event, determine and assign a second 3D patient body model to a second sensor detection event, create a tissue deformation model from first to second 3D patient body models, and perform a reconstruction of a 3D distribution of gamma-ray emitting radioisotopes inside the patient by using first and second sensing events and the tissue deformation model.

In one example of such reconstruction, the computer uses an image space remapping method to create a correspondence between image elements, or image nodes, before and after the body deformation, and use for the two detected gamma events backprojection operators that account for the remapped image elements or nodes. Several remapping algorithms known in the field could be used. The computer connected operationally to the computer vision camera could also be operationally connected to actuators powering the mechanical arm (101), the lever (103) and the wheels (108a) and (108b). When the computer vision algorithm detect significant changes in the body of the patient that could even indicate collision, the computer can be programmed to stop the movement of the jointed arm and gamma camera panels to avoid collisions between any components of the SPECT imaging system with the body of the patient. Moreover, the computer vision subsystem could monitor the space in the projected path of the gamma camera panels during a scan to detect other objects or people. When such detections take place, the computer could stop the movement of the jointed arm and gamma camera panels to avoid collisions between any components of the SPECT imaging system with the other objects or people.

In some embodiments, the jointed arm (101) may be affixed to another physical object instead of being affixed directly to the body of the controller (100). Examples of such objects are: floor, ceiling, walls, other portable controllers, rails.

In some embodiments in which a user actuates one or more of the jointed arm, lever arm, and gamma camera panels assembly to perform a static scan (e.g., the gamma camera panels don't move with respect to the patient) or a dynamic scan (e.g., the gamma camera panels move with respect to the patient), the camera (106) and/or other tracking modality external to the jointed arms may not be used. In such embodiments, the co-registration of a sensing event to the body of the patient can be done by reading and analyzing the position data of any joint or actuator involved in the movement of the gamma camera panels within the room, such as the jointed lever (103), jointed arm (101), and wheels (108a) and (108b). This co-registration modality assumes that the body of the patient stays still with respect to the room in which the gamma camera panels are moved to perform a scan. In some embodiments, the bed (105) or a chair on which the patient lays or sits may move with respect to the controller, in order to augment the effective reach of the panels during a scan.

In some embodiments, the gamma camera panels (102a) and (102b) comprise gamma sensors that provide sensor data containing information for use by an image reconstruction program running on a computer to provide imaging of radiotracer distributions with finite resolution along the direction at which either gamma camera is most sensitive, even when the gamma camera panels are essentially in static location with respect to the patient. In some embodiments, said finite resolution is less than 20 mm for a range of distances that cover at least 50 mm.

In some embodiments, each of the gamma camera panels (102a) and (102b) provides an imaging field of view larger than 15 degrees, preferably close to 45 degrees. In some embodiments the field of view may be larger than 20, 25, 30, 35, 40, or 45 degrees. The imaging field of view is defined as the range of angles, with respect to the direction at which the gamma camera has maximum imaging sensitivity, from which gamma photons can be detected and imaged by gamma sensors comprised by the gamma camera panel with a sensitivity larger than a hundredth the maximum imaging sensitivity. Such imaging field of views allow the gamma camera sensors to capture imaging information from a multitude of directions, which enables a better coverage of imaging projection angles, even from a static location, or from a reduced range of locations around the patient.

In some embodiments, each of the gamma camera panels (102*a*) and (102*b*) comprises a gamma photon attenuating imaging component placed in front of a position sensitive gamma ray sensor. The photon attenuating imaging component can be selected from a group containing a coded aperture mask, a straight and/or slant parallel hole collimator, a pinhole collimator or a multipinhole collimator. In a preferred implementation, the gamma ray sensor provides the location of the gamma photon interaction with a resolution better than 2 mm in all three dimensions. In a preferred embodiment, the photon attenuating imaging component is a coded aperture mask with a field of view larger than 30 degrees. Preferably, the pattern of the coded aperture mask minimizes the side lobes in the instrument response function. The coded aperture pattern can have an opening fraction, defined as the ratio of empty mask pixels to the total number of pixels, that ranges from close to 0% to close to 100%. In some embodiments, the opening fractions may range from a fraction of 1% to around 50%.

In some embodiments, the gamma sensors comprised by the gamma camera panels (102*a*) and (102*b*) are selected to detect with higher sensitivities gamma photons of higher energies, such as energies above 200 kilo-electron volts (keV) or above 500 keV. In this case, no gamma photon attenuating imaging components may be used, and instead, the gamma-ray Compton scattering mechanism may be used to provide imaging information. The gamma sensors may be selected to provide position resolution in 3D with a resolution better than 2 millimeters (mm), and an energy resolution better than 4%. In this case, a computer operationally coupled to the gamma sensors will determine a scattering angle around a scattering direction of a gamma ray interacting at least two times in the sensor system by resolving the kinematics of the gamma ray interactions within the sensor system. These scattering angles around scattering directions will then be used to create spatially registered cones. A 3-D map of gamma ray sources can then be built by resolving statistically the intersection of at least two spatially registered cones. This imaging modality may be used to image positron emitting radioisotopes.

In some embodiments, the jointed mechanical arm (101) is a 6 axis robotic arm. A computer operationally coupled to actuators inside the robotic arm can actuate the joints to perform a SPECT scan by moving the panels around the patient's body. A computer vision process may run on the computer to analyze the image frames from the computer vision camera (106) or from another patient 3D scanner to build a 3D model of the patient and to identify individual body parts. Instructions may be stored on the computer to use the output of the computer vision process in order to actuate the robotic arm to position the panels in such a way as to perform specific types of imaging scans, such as a head scan, a neck scan, a whole body scan, a cardiac scan, a torso scan, and so forth.

In other embodiments, a portable SPECT imager may comprise a single gamma camera panel connected to a jointed mechanical arm. In other embodiments, a portable SPECT imager may comprise three, four, or more gamma camera panels connected to a jointed mechanical arm directly or through a similar lever as in FIG. 1.

In some embodiments, a computer vision camera can be mounted on the gamma camera panels (102*a*) and (102*b*), lever (103), or other objects. As with computer vision camera (106), this camera can provide data to be analyzed by a computer to determine the outline of the patient's body and to determine the relative position and orientation of various SPECT system components with respect to each other or to respect the body of the patient, Following a SPECT scan that delivered a 3D distribution of gamma-ray emitting radioisotopes, a computer operationally connected to an ultrasound probe or ultrasound transducer, a tracking system employed to track the ultrasound probe with respect to the body of the patient or with respect to a fixed point of reference, a memory storing a 3D distribution of gamma-ray emitting radioisotopes co-registered to the patient, and a visualization device, may be used to track the ultrasound system with respect to the patient or with respect to a fixed point of reference. The computer may further determine a co-registration between the 3D distribution of gamma-ray emitting radioisotopes and an ultrasound scan using the ultrasound tracking information, and deliver to the visualization device an image that comprises an augmentation of features of the 3D distribution of gamma-ray emitting radioisotopes onto the ultrasound scan. Moreover, the computer can analyze the live ultrasound images to create a tissue deformation model by tracking specific features in the ultrasound image from a first ultrasound frame to a second ultrasound frame. This deformation model can be used to remap an original SPECT image stored in a memory to create a modified SPECT image that integrates the modeled tissue deformation. This modified SPECT image can then be augmented onto the second ultrasound frame.

Other tissue deformation corrections could be used, such as frame-based registration approaches and gamma sensor data-driven approaches, such as centroid of distribution (e.g., detecting body motion based on changes in a centroid of distribution trace over a time interval).

In some embodiments the platform (105) may also comprise a lever arm (110) that may extend out of the body of the platform when the jointed arm stretches out in order to address the potential for instrument tip-over. Such arm can comprise a wheel (111) at the distal end.

Although it is understood that an ultrasound probe is a structure that comprises an ultrasound transducer, the terms "an ultrasound probe" and "an ultrasound transducer" may be used interchangeably in the description.

In some embodiments, instead of using gamma-ray panels mounted on a robotic arm, other types of sensors could be used. For example, one or both panels (102*a*) and (102*b*) can comprise a magnetic sensor or a magnetic sensor array. Such magnetic sensor system may be able to measure magnetic signals or changes in magnetic signals that reflect magnetic properties of tissue. In some implementations, the magnetic properties of tissue are defined by molecular agents injected in the body of the patient. In some implementations, these molecular agents may be labeled with magnetic nanoparticles. The panels may move across the body of the patient to take magnetic signals from different locations. A three-dimensional (3D) map of the distribution of the agents may be reconstructed by an operationally connected computer by using spatially registered magnetic signal data from the magnetic sensor assembly. The magnetic signal data may be spatially registered by the computer by using tracking data from the computer vision system or from the robotic arm kinematics. Although examples include using gamma sensors for molecular imaging and molecular imaging guidance of interventions, it is understood that the methods and systems described herein can be envisioned by using sensor panels comprising magnetic sensor assemblies for molecular imaging. These magnetic sensor systems may be used in combination with injecting molecular agents with specific magnetic properties inside the body of the patient.

FIGS. 2A-2D show multiple views of a SPECT camera head comprising gamma camera panels (200a) and (200b) connected to a mechanical lever (201) through mechanical arms (202a) and (202b), respectively. A computer vision camera (203) is seen connected through a connector (204) to the end of the distal end of the mechanical jointed arm (205).

Figure 2A:
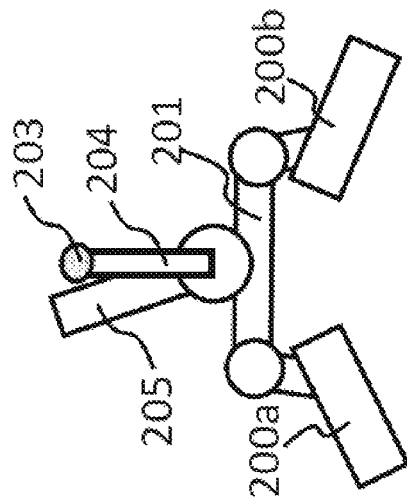
FIGS. 2A-2D show views of a two gamma camera panel system in two configurations.

FIG. 2A shows the two panels (200a) and (200b) in close configuration.

Figure 2B:
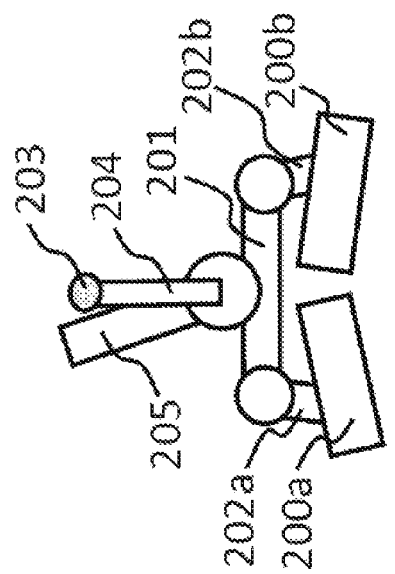

FIG. 2B shows the two panels (200a) and (200b) in a separated configuration in which the relative distance between panels is increased and the roll of the panels has changed. This separated configuration will provide space between the two panels for other imaging probes or medical instruments to be introduced.

Figure 2C:
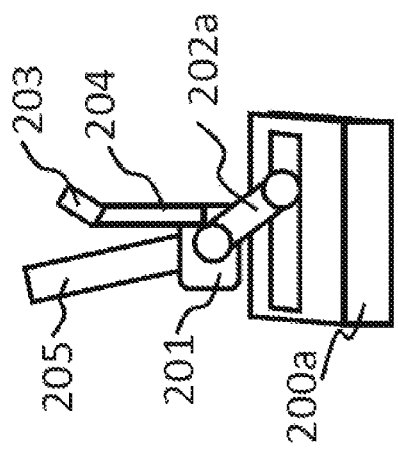
Figure 2D:
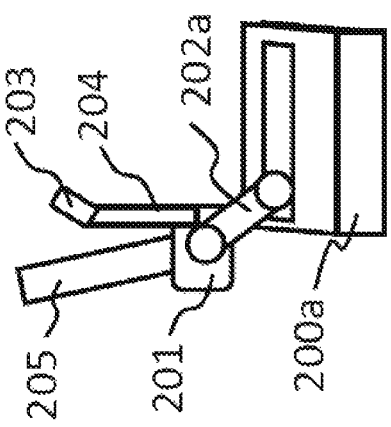

FIGS. 2C and 2D show a side view of the SPECT camera head in two configurations. The assembly made out of the lever (201) and arms (202a) and (202b) may allow the gamma camera panels (200a) and (200b) to move sideways (away from each other), as well as front to back.

FIG. 2C depicts the gamma camera panels in a forward configuration.

FIG. 2D depicts the gamma camera panels in a backward configuration, in which the panels' center of gravity is placed closer to the connector between the lever (201) and jointed arm (205). Whereas the configuration of FIG. 2C may enable for other imaging probes to be placed between the two gamma camera panels by providing empty space above and between the gamma camera panels, the configuration of FIG. 2D may allow other imaging probes to be placed on the side of the two panels.

Various configurations and relative placements of the gamma camera panels may be used not only to accommodate for other medical instruments or imaging probes to be introduced in the gamma camera's field of view, but also to allow for various levels of overlap of imaging fields of view between the two panels, as well as to allow for a patient scanning by closely following the patient anatomy.

Figure 3:
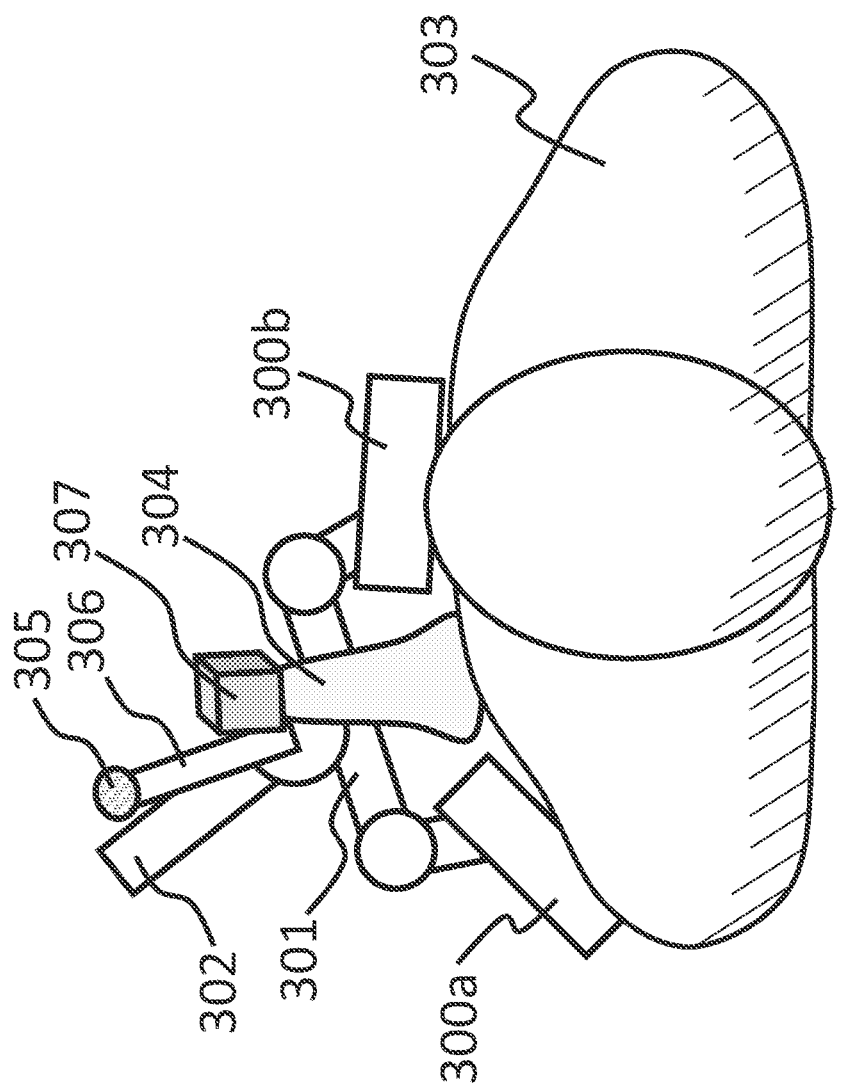
FIG. 3 shows a depiction of a portable SPECT camera system co-registered with an ultrasound probe placed between the panels by using a visual camera.

FIG. 3 shows a depiction of the SPECT camera head used in combination with another medical imaging probe. Two gamma camera panels (300a) and (300b) are shown mechanically connected by lever (301) to the distal end of a mechanical jointed arm (302). The system is shown scanning a patient (303). In this embodiment, an ultrasound imaging probe (304) is introduced in the space between the two panels (300a) and (300b). The imaging field of view of the ultrasound imaging probe (304) may partially or totally overlap onto the imaging field of view of either or both panels (300a) and (300b).

A computer vision camera (305) is connected to the lever (301) and jointed arm assembly (302) through a connector (306). The computer vision camera may have an observational field of view that covers the general area where the ultrasound probe is used to scan the patient. The computer vision camera provides data required by a tracking program stored in the memory of a computer operationally coupled to the computer vision camera to provide the location and orientation of the ultrasound probe with respect to the camera. A fiducial marker (307) may be attached to the ultrasound probe to aid in determining the location and orientation of the ultrasound probe with respect to the camera (305). Likewise, the computer vision camera may provide data required by a tracking program stored in the memory of the said computer to provide the location and orientation of each of the gamma camera panels (300a) and (300b) with respect to the computer vision camera (305). A fiducial marker (not shown) may be attached to each of the two gamma camera panels to aid in determining the location and orientation of the each of the panels with respect to the camera. The relative location of the panels and ultrasound probe with respect to the computer vision camera can be then combined to determine the relative position of the gamma camera panels and ultrasound probe with respect to each other. This can enable to coregistration of images produced by the gamma cameras and ultrasound probe. Moreover, the memory may have instructions for execution by a processor to use the computer vision camera data to determine an outline of the body of the patient. This can be used to further determine the relative position of the gamma camera panels and ultrasound probe with respect to the body of the patient.

Alternatively or additionally, a computer (e.g., the controller (100) shown in FIG. 1) may be operationally coupled to sensors connected to the lever (301) to receive position information with regard to the articulation of the mechanical components of lever (301) to infer the position and location of the gamma camera panels (300a) and (300b) with respect to computer vision camera (305).

Figure 4:
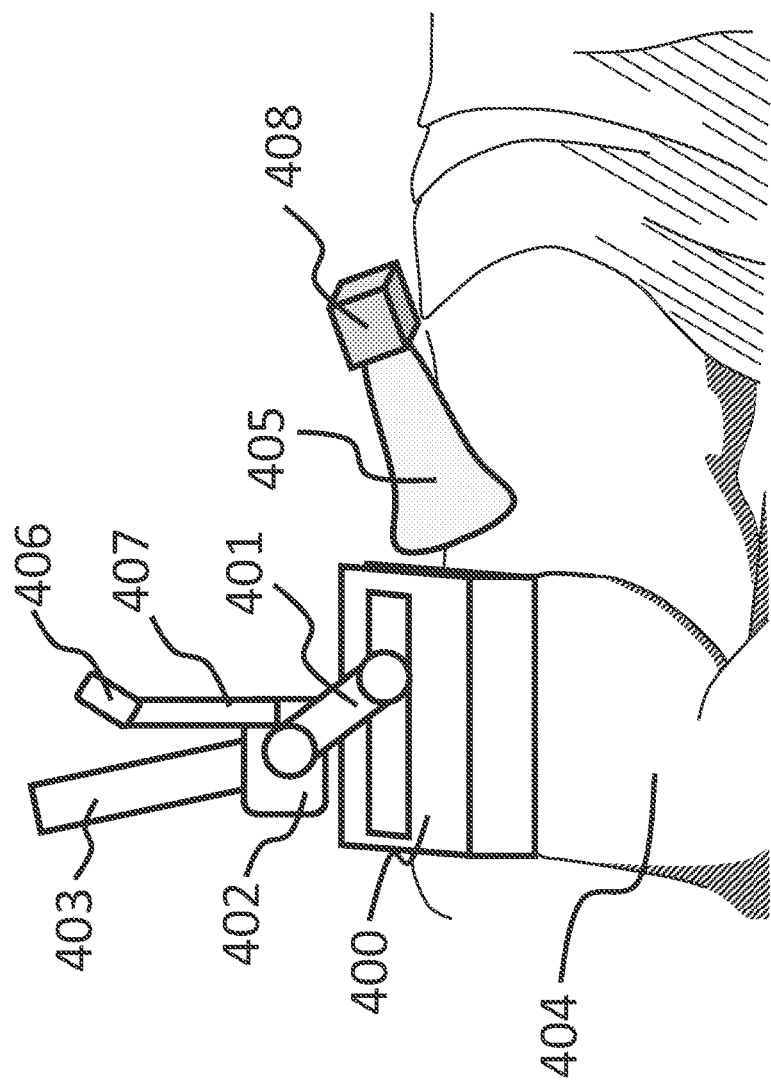
FIG. 4 shows a depiction of a portable SPECT camera system co-registered with an ultrasound probe placed on the side of the panels by using a visual camera.

FIG. 4 shows an illustration of the system shown in FIG. 3, but in which the ultrasound probe is placed outside of the space between the two panels. This modality may be useful for scanning organs inside the rib cage, such as heart and liver. One of the gamma camera panels (400) is shown mechanically connected by lever (401) to the distal end (402) of a mechanical jointed arm (403). The system is shown scanning a patient (404). In this embodiment, an ultrasound imaging probe (405) is used to scan the patient from a location adjacent but exterior to the gamma camera panels. The imaging field of view of the ultrasound imaging probe (405) may or may not partially or totally overlap onto the imaging field of view of either or both panels. An computer vision camera (406) is connected to the distal end (402) through a connector (407). The computer vision camera and the processing of data for tracking and co-registration can take place in a similar way as described in FIG. 3. A fiducial object (408) is shown attached to the ultrasound probe to aid ultrasound probe tracking.

Figure 5:
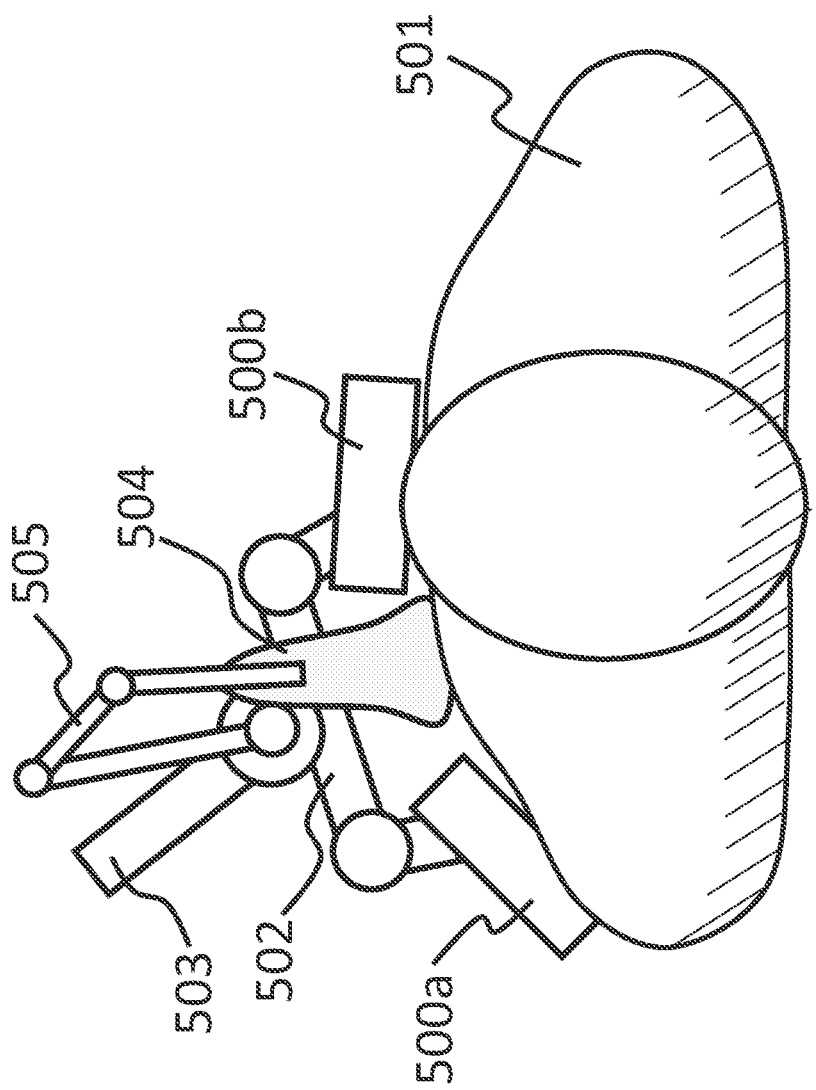
FIG. 5 shows a depiction of a portable SPECT camera system co-registered with an ultrasound probe placed between the panels by using an jointed mechanical arm.

In another embodiment, jointed mechanical arms can be used to track the position and orientation of the ultrasound sensor with respect to the gamma camera panels. FIG. 5 depicts an ultrasound probe co-registered to the gamma camera panels through the use of a jointed arm with coordinate measurement capabilities. Two gamma camera panels (500a) and (500b) are shown scanning a patient (501). These panels are mechanically connected by lever (502) to the distal end of a mechanical jointed arm (503). In this embodiment, an ultrasound imaging probe (504) is introduced in the space between the two panels (500a) and (500b). The imaging field of view of the ultrasound imaging probe (504) may partially or totally overlap onto the imaging field of view of either or both panels (500a) and (500b). A jointed arm (505) with coordinate measurement capabilities may be mounted on the jointed arm assembly (502)-(503). This arm (505) may have its distal end affixed rigidly to the ultrasound probe.

A tracking program stored in the memory of a computer operationally coupled to sensors connected to the ancillary arm (505) may be configured to receive position information with regard to the articulation of the mechanical components of arm (505) to infer the position and location of the ultrasound probe with respect to the lever (502). Additionally, the computer may be coupled to sensors connected to the lever (502) to receive position information with regard to the articulation of the mechanical components of lever (502) to infer the position and location of the gamma camera panels with respect to the lever (502). The tracking program may combine the tracking information for the ultrasound and gamma camera panels to determine their relative position.

The use of the jointed ancillary arm (505) could be used in addition to the camera (106) in FIG. 1. As such, the tracking algorithm on the computer may combine various tracking modalities to determine the location of gamma camera panels, the ultrasound probe, and the patient body with respect to each other.

Figure 6:
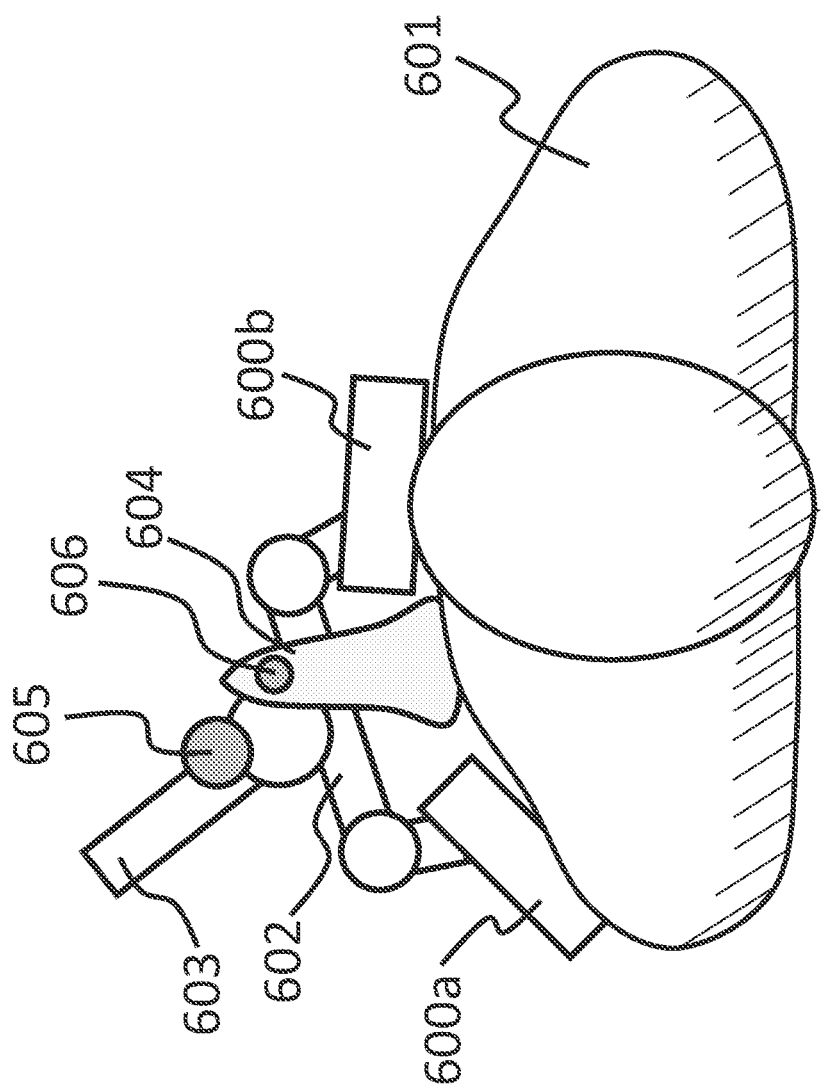
FIG. 6 shows a depiction of a portable SPECT camera system co-registered with an ultrasound probe placed between the panels by using electromagnetic field trackers.

In yet another embodiment, other tracking sensors can be used to track the position and orientation of the ultrasound sensor with respect to the gamma camera panels. An example can be electromagnetic field trackers. FIG. 6 depicts an ultrasound probe co-registered to the gamma camera panels through the use of magnetic tracking system. Two gamma camera panels (600a) and (600b) are shown scanning a patient (601). These panels are mechanically connected by lever (602) to the distal end of a mechanical jointed arm (603). In this embodiment, an ultrasound imaging probe (604) is introduced in the space between the two panels (600a) and (600b). The imaging field of view of the ultrasound imaging probe (604) may partially or totally overlap onto the imaging field of view of either or both panels (600a) and (600b). An electromagnetic transmitter (605) may be mounted in close proximity to the ultrasound probe, in this case it is mounted on the jointed arm assembly (602)-(603). An electromagnetic receiver (606) may be rigidly affixed onto the ultrasound probe. A tracking program stored in the memory of a computer operationally coupled to the transmitter (605) and the receiver (606) may be used to infer the position and location of the ultrasound probe with respect to the transmitter (605). Additionally, other electromagnetic receivers (not shown) may be rigidly affixed onto the gamma camera panels (600a) and (600b), and may be operationally coupled to the computer. The tracking program may use the data from receivers and transmitters to determine the location of gamma camera panels and ultrasound probe with respect to each other.

In some embodiments, the transmitters and receivers may be interchanged. In other embodiments the transmitter may be affixed to another object and the component (605) may be a receiver. In yet other embodiments, the electromagnetic units affixed to instruments may act as both transmitters and receivers.

Alternatively to affixing receivers on the gamma camera panels or additionally to that, the computer may be operationally coupled to sensors connected to the lever (602) to receive position information with regard to the articulation of the mechanical components of lever (602) to infer the position and location of the gamma camera panels (600a) and (600b) with respect to the transmitter (605). The tracking program may combine the tracking information for the ultrasound and gamma camera panels to determine their relative position.

Tracking systems based on electromagnetic transmitters and receivers could be used in addition to the camera (106) in FIG. 1. As such, the tracking algorithm on the computer may combine various tracking modalities to determine the location of gamma camera panels, ultrasound and patient body with respect to each other. An example of a tracking system is one that uses external infrared stereoscopic trackers combined with infrared reflective spheres attached in unique patterns on various components that require tracking. Any combination of the tracking and co-registration techniques presented here, as well as other tracking systems could be used. For example, the tracking system may be an optical tracking system, an electro-mechanical tracking system, an electromagnetic tracking system, an ultrasound tracking system, a depth imaging tracking system, a combination thereof.

Figure 7:
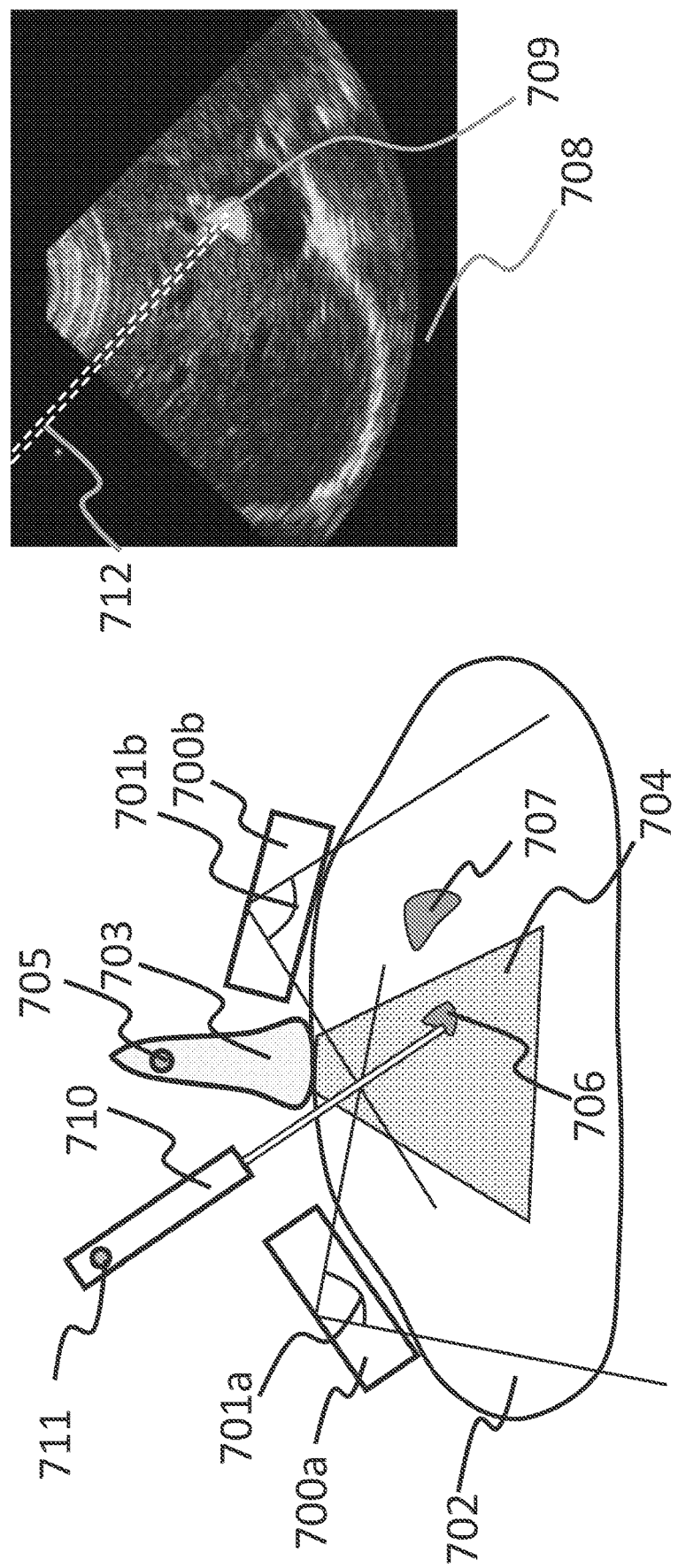
FIG. 7 shows a depiction of a portable SPECT camera system co-registered with an ultrasound probe guiding a percutaneous medical intervention.

FIG. 7 shows a depiction of an embodiment of the portable SPECT gamma camera panels (700a) and (700b), each of which with a field of view (701a) and (701b) used to observe a patient (702). An ultrasound probe (703) with a field of view (704) is co-registered to the panels (700a) and (700b) through the use of any combination of tracking systems. In this depiction, a tracking sensor (705), such as a magnetic field receiver is shown attached to the ultrasound probe (703). As a result of using an image reconstruction algorithm on the data received from the gamma cameras, 2 SPECT image features (706) and (707) with radioactive uptake may be reconstructed inside the patient in 3D. The SPECT image features (706) and (707) may be constructed in "real-time," that is with a finite frame rate, ideally of better than 1 frame for 2-3 seconds, or they can be constructed by acquiring data over a longer period of time, with the gamma camera panels scanning the patient from either from a static position or dynamically by having them move around the body of the patient. In the latest case, the features (706) and (707) may not correspond to their actual locations inside the body of the patient if there have been tissue deformations, patient movements of organ movements.

Guided by the SPECT image, the co-registered ultrasound probe (703) may be brought in close proximity to the gamma camera panels in order for its field of view to intersect part of a SPECT feature (706). In a first stage, a computer operationally connected to the ultrasound probe and a visualization device may create an ultrasound image (708) delivered by the ultrasound probe (703) and may have it augmented with SPECT image features (709) representing a section through the SPECT 3D map in the ultrasound field of view (704). In a second stage, the same computer may identify and correct possible rigid transformations between SPECT image and ultrasound image due to patient, furniture, or other sources of motion. The rigid transform is computed by snapping the SPECT image features on top of the ultrasound image features. The snapping process consists of: (1) automatically identify visual features in both images, (2) matching SPECT image features to ultrasound features, and (3) compute a rigid transform (projection) based on the matched features. In other words, the system may create a model of movements of features in the ultrasound image from a first ultrasound frame to a second ultrasound frame, and create a changed SPECT image based on the model of movements of features in the ultrasound image. The resulted augmented image allows the user to identify the patient's anatomy surrounding the SPECT feature (706), similarly to what a CT scan would provide in a SPECT/CT imaging system.

Moreover, the ultrasound image (708) could be used to guide interventional medical instruments, such as a percutaneous biopsy needle (710) or an ablation therapy device, towards a target of interest highlighted by the SPECT image. In some embodiments the medical instrument may also be tracked to allow for a co-registration between the medical instrument, the ultrasound and the SPECT image. In FIG. 7, a tracking sensor (711), such as a magnetic field receiver, is shown to be used for co-registration purposes. Alternatively, or additionally, a mechanical instrument guide can be used to define the movement of the medical instrument. Using either method, a projected trajectory of the instrument, in this depiction, the projected trajectory of the needle (712) can be augmented onto the ultrasound image (708).

In some embodiments, a head mounted display can be used to visualize ultrasound image (708) and/or SPECT image features (706) and (707) augmented onto the natural view of a user by using a head mounted display system worn by the user and with capability of coregistration between the eyes of the user to the co-registered coordinate system associated with the ultrasound and SPECT image.

In some embodiments the whole medical intervention process may be automated, in which case, the ultrasound (703) and intervention device (710) are controlled by a computer through the use of mechanical jointed arms.

Figure 8:
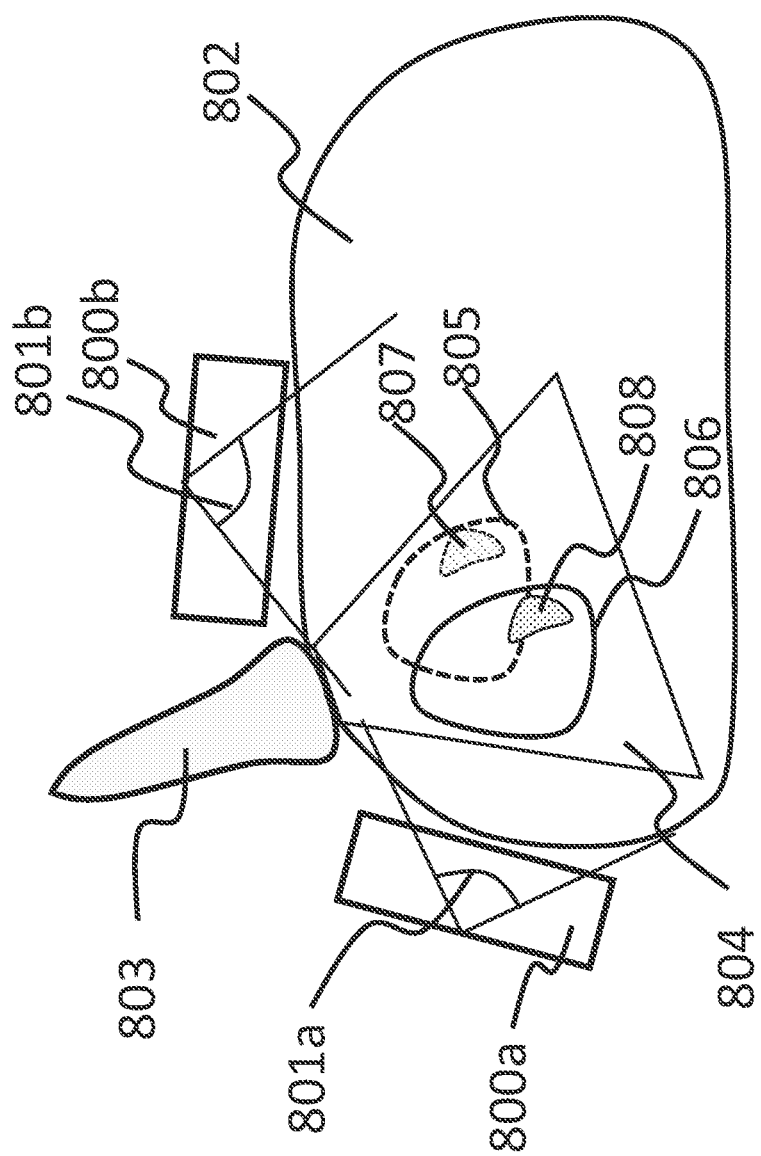
FIG. 8 shows a depiction of a portable SPECT camera system co-registered with an ultrasound probe used to correct for tissue deformations in the SPECT image formation.

In some clinical applications it may be relevant to create a molecular SPECT image of organs that move and deform easily. In such cases, the ultrasound image could be used to guide corrections in the SPECT image based on the tissue deformations and movements observed in the ultrasound image. FIG. 8 shows a depiction of the method by which such corrections can be implemented. In the depicted embodiment of the portable SPECT, gamma camera panels (800a) and (800b), each of which with a field of view (801a) and (801b) observe a patient (802). An ultrasound probe (803) with a field of view (804) is co-registered to the panels (800a) and (800b) through the use of any combination of tracking systems. An ultrasound image feature (805) that may appear in one ultrasound scan may be deformed and displaced in a subsequent ultrasound scan and may appear as ultrasound image feature (806). If there is an area of increased radioactive tracer uptake, or SPECT image feature (807) at the time of the first ultrasound scan, that SPECT image feature may be located in a different location at the time of the second ultrasound scan. Without tissue deformation correction, if the acquisition time will extend over a time comprising the times of the two ultrasound scans, the SPECT image reconstruction algorithm will not be able to create a SPECT feature with the correct extent. In such cases, the ultrasound can be used during the SPECT scan to monitor the movement of features visible in the ultrasound image.

The sequence of ultrasound images can be analyzed automatically by an imaging analysis algorithm to determine the field of organ movement and deformations taking place from one ultrasound image scan to another. This may be achieved by automatically identifying ultrasound image structures (such as organs), create a parameterization of those structures, and track their motion and deformation in time. The ultrasound image structures may be defined by geometric primitives as follow (from most simple to most complex structure): point, line, rectangular shape, and round shape. These geometric primitives can be parametrized using a patch (a point with a radius) for point-like structures, and a contour for all other primitives. The contour parametrization depends on the underling ultrasound image structure: a line is represented as a curve, a round shape as an oval, and a rectangular shape as polygon. The image structures identified in consecutive ultrasound frames are matched. Each matched pair is used to quantify the motion and deformation suffered by the organ (or the structure). The resulted motion fields and deformations are used to remap the imaging space elements from one frame to the next, and the reconstruction of the SPECT image will use the remapped imaging space elements to build a SPECT image corrected for tissue deformation. When the movement of the organs is cyclical, such as in the case of heart movements, multiple SPECT images can be created for each sequence within a period of the cyclical movement. In some embodiments, the ultrasound probe is able to provide 3D ultrasound images. This will create a "wedge-like" 3D imaging volume that will capture better more complex organ movements, leading to potentially better organ deformation corrections.

If a more complete SPECT image is available, like for example, from an anterior SPECT scan, such SPECT image could be used as a prior into the reconstruction of a current, real-time SPECT image. For example, algorithms can run on the operationally connected computer to update a SPECT image to create a real-time SPECT image by comparing latest gamma-ray detection events with an estimation of events. The estimation of events can be computed by the computer by computationally projecting forward into the sensor a previous SPECT 3D map. The computational projection can account for the latest configuration of the gamma-ray camera, including sensor and mask. The computer can calculate deviations between detected events and estimated events to determine deformations in the previous SPECT 3D map that are consistent with the latest detected events. An example of an algorithm that can be used to update in real-time molecular images is described in Lu, Y., et al. (2019). Data-driven voluntary body motion detection and non-rigid event-by-event correction for static and dynamic PET. *Physics in Medicine & Biology*, 64(6), 065002.

In some embodiments, the computation of the real-time SPECT images may use tracked deformable ultrasound features from images taken with the ultrasound probe co-registered with the SPECT sensor panels. Parametrization of ultrasound features are described above. Examples of feature extraction methods are described in Revell, J., et al. (2002) "Applied review of ultrasound image feature extraction methods" In The 6th Medical Image Understanding and Analysis Conference (pp. 173-176). BMVA Press; Alemán-Flores, M., et al. (2005, February) "Semiautomatic snake-based segmentation of solid breast nodules on ultrasonography" In International Conference on Computer Aided Systems Theory (pp. 467-472) Springer, Berlin, Heidelberg; Zhou, S., Shi, J., Zhu, J., Cai, Y., & Wang, R. (2013) "Shearlet-based texture feature extraction for classification of breast tumor in ultrasound image" Biomedical Signal Processing and Control, 8(6), 688-696. These parametrized ultrasound features can by tracked by the computer to obtain tracked deformable ultrasound features by using methods, such as described in Yeung, F., et al. (1998). Feature-adaptive motion tracking of ultrasound image sequences using a deformable mesh. *IEEE transactions on medical imaging*, 17(6), 945-956. The tracked deformable ultrasound features can be used by the computer in the calculation of the updated real-time SPECT image. This can be done, for example, by using the tracked parametrized ultrasound features to constrain the solution for SPECT image deformation model. In some embodiments, the computer can create this SPECT image deformation model to obtain an updated SPECT image by using a previously collected SPECT 3D map. In this case, the SPECT image elements are basically pinned onto the tracked deformable ultrasound features and are moved along with the ultrasound features. In some other embodiments the computer can create a SPECT image deformation model to obtain an updated SPECT image by using real-time gamma data in combination with a previously collected SPECT 3D map. In this case, the tracked deformable ultrasound features are used to constrain the deformation model calculated by comparing the latest gamma-ray detection events with an estimation of events calculated by the computer from the previously collected SPECT 3D map, as described in the previous paragraph. The computer may use a deformable model data fusion filter to combine the ultrasound deformable model and the deformable model that compares the real-time gamma ray data with a previous SPECT map. This deformable model data fusion filter may use a Kalman filter (Welch, G., & Bishop, G. (1995) "An introduction to the Kalman filter"). The parameters of the filter that determine how the filter is applied for a certain application may be changed by the computer or by an user, and may take into consideration the quality of the ultrasound image, the quality of the ultrasound features extracted, the quality of the ultrasound deformation tracking model, the gamma-ray count rate, the estimation a the gamma-ray count rate extracted from the forward projection of a previously reconstructed SPECT 3D map, the SPECT image signal-to-noise ratio, and others. For example, the filter running on the computer may emphasize more in the construction of the updated SPECT image the tracked ultrasound deformable structures if the reliability of the ultrasound tracked structures is high and the detected gamma-ray count rate is too low, and the other way around.

These systems and methods can be also employed to extended volumetric areas inside the patient that may not be viewed directly in the ultrasound scan by propagating the deformations tracked in the ultrasound scan away from the ultrasound imaged volumes by using specific mechanical and elastical properties of tissue deformation. These deformation propagation methods can also use the 3D model of the patient, as tracked by the computer vision system. For example, this 3D model of the patient can provide boundary conditions for the deformations away from the scanned ultrasound volumes.

Figure 9:
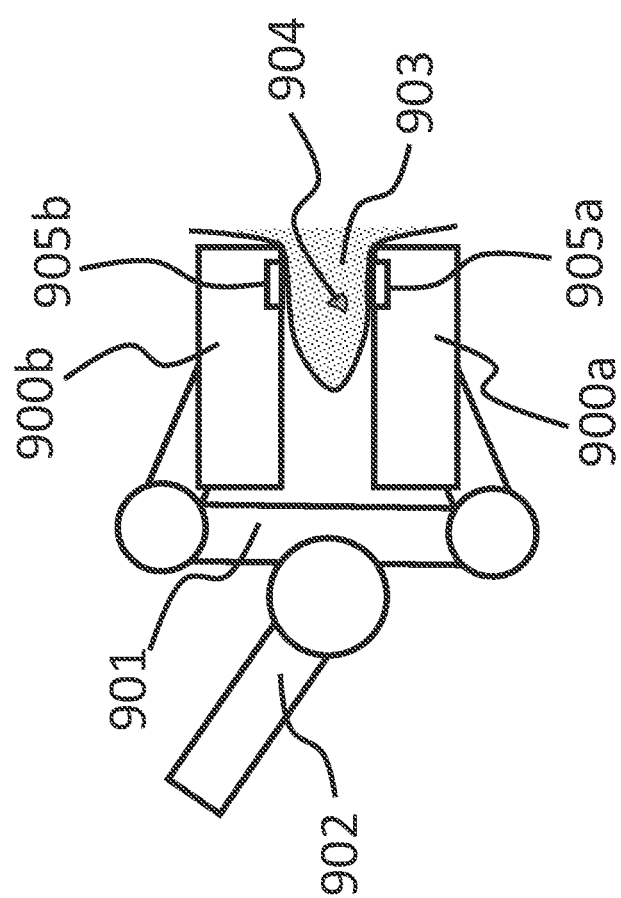
FIG. 9 shows a depiction of a portable SPECT camera system placed in a configuration to scan a specific body part of a patient.

FIG. 9 shows a depiction of an embodiment of the portable SPECT gamma camera panels (900a) and (900b), mounted through a jointed lever (901) to a jointed arm (902). In this depiction, the panels are positioned to scan a specific body part of interest, such as a human breast (903). In this case the panels are essentially parallel to each other and the field of view of the gamma cameras overlap to a very large extent. In other embodiments the gamma cameras may be placed at other angles with respect to each other, such as 90 degrees from each other.

In some embodiments, the gamma camera panels (900a) and (900b) comprise gamma sensors that provides sensor data containing information used by an image reconstruction program running on a computer to provide imaging of radiotracer distributions with finite resolution along the direction at which either gamma camera is most sensitive, when the gamma camera panels are essentially in static location with respect to the body part (903) of the patient. In some embodiments, said finite resolution is less than 20 mm for a range of distances that cover at least 50 mm. In such an embodiment a lesion (904) inside the body of the patient of increased radiotracer uptake may be imaged in 3D. As compared to a planar imaging setup, a 3D image of the radiotracer distribution will provide better lesion detectability and localization.

In some embodiments, the panels (900a) and (900b) may comprise tactile pressure sensors (905a) and (905b) placed preferably on the panel surface facing the patient's body part (903) to get information about pressure applied by the panels onto the body of the patient or by the panels onto other objects. These tactile pressure sensors may be operationally coupled to a computer that is also connected to actuators that move the panels with respect to the patient. The computer may use a program to change the position of the panels in order to keep the pressure applied by the panels onto the patient or other objects within a desired range of values. Tactile pressure sensors could be capacitive, resistive, piezoelectric, or any other sensor able to provide tactile pressure between objects.

While in this configuration, co-registered ultrasound probes and percutaneous medical devices could be used on the examined patient body part, similarly to the embodiment described in FIG. 7.

Figure 10:
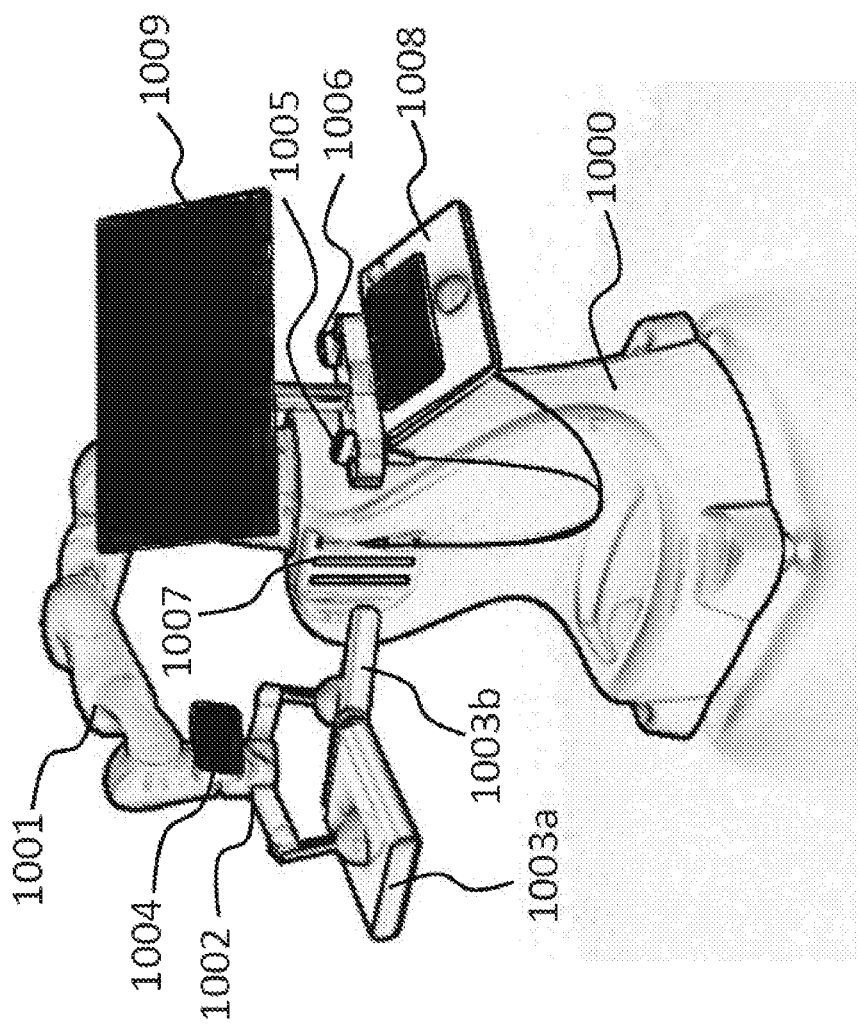
FIG. 10 shows a depiction of embodiments in which a portable cart integrates a SPECT gamma camera mounted on an articulated arm and a medical ultrasound system.

FIG. 10 shows a depiction of an embodiment in which a portable cart (1000) integrates a SPECT gamma and a medical ultrasound system. A 6 axis robotic arm (1001) is affixed onto the portable platform (1000). A jointed gamma camera sensor mounting assembly (1002) is affixed onto the distal end of the robotic arm (1001). Gamma camera panels (1003a) and (1003b), as described above, are mounted onto the mounting assembly (1002). A computer vision camera (1004), as described above, is mounted onto the mounting assembly (1002). Ultrasound probes (1005) and (1006) are operationally connected to the ultrasound electronics and controller through connector panel (1007). In a preferred embodiment, a console (1008) is used by a user to control the ultrasound system, the SPECT camera system, and the mechanical system, including the robotic arm. A monitor (1009) is depicted here as a visualization device. Other visualization devices could be used, such as a head mounted display co-registered to the patient. The cart can enclose any of the following components: a master controller (computer), including graphical processing units (GPUs), a controller for the mechanical subsystem, including the 6-axis robotic arm, electronics for ultrasound pulse-forming and readout, and electronics for gamma camera read-out. SPECT and ultrasound co-registered images can be delivered by the master computer to the visualization device. Other medical sensors or other medical imaging devices could be used instead, or in addition to ultrasound probes. Examples are: fluorescence imaging probes, optical coherence tomography probes, computer vision cameras, infrared cameras, impedance sensors, etc.

Figure 11:
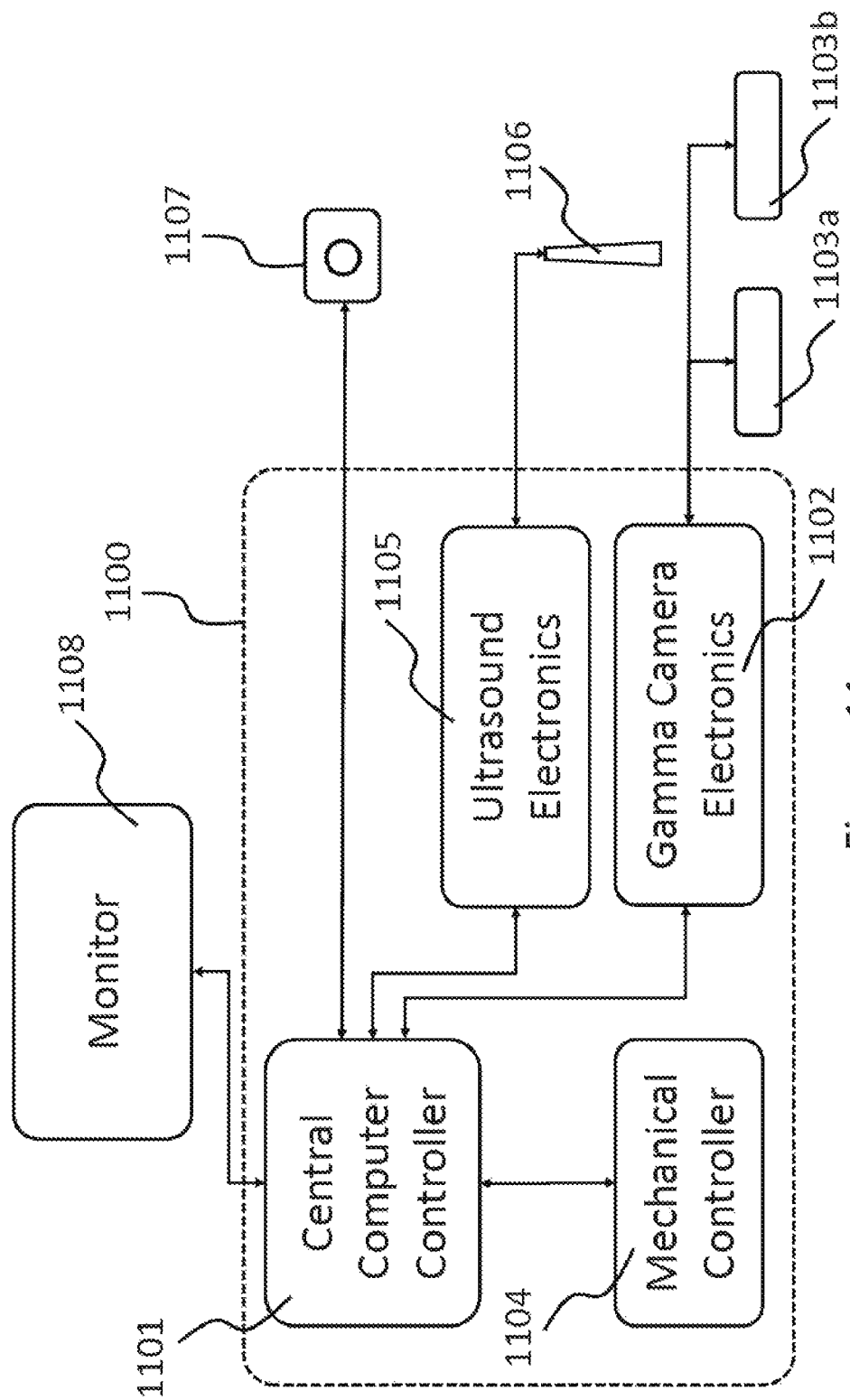
FIG. 11 shows a depiction of the operational connections between the components of a portable imaging system comprising a SPECT gamma camera and a medical ultrasound system.

FIG. 11 shows a depiction of the operational connections between the components mentioned in the description of FIG. 10. The enclosure of the portable platform (1000) is represented by (1100). The enclosure comprises at least a central computer controller (1101) that is used to read data from sensors and other subsystem. This computer integrates the data to determine tracking information for objects of interest, to reconstruct SPECT images and potentially other medical images from other sensors, to create co-registered images, to augment images onto each other, to send visualization data to a visualization device, to control other controllers, subsystems and electronics. The enclosure can also comprise electronics (1102) to read out and control the gamma cameras (1103a) and (1103b). The enclosure can also comprise mechanical controllers (1104) that receive sensing mechanical information and control the jointed arm (1001) and potentially other actuators attached to the wheels of the platform (1100), to the patient bed or seat, the gamma camera mounting assembly (1002), or to other objects, medical devices or sensor assemblies that may be used during scanning or interventions. The enclosure can also comprise electronics (1105) that provide pulse shaping for, and read out signals from ultrasound transducers (1106). When other imaging and sensing modalities may be used, their control and readout electronics can be housed inside the platform enclosure, as well. Various ports will be provided for all such imaging probes and sensors, for example on the connector panel (1007). The central computer controller may also control and read out tracking devices, computer vision system, and so forth. As an example, in the illustration, a computer vision camera (1107) is shown to be read out and controlled by the central computer controller (1101). The visualization output created by the central computer can be sent to a visualization device, such as a monitor (1108) or to other computers over a network, or to a head mounted display.

Figure 12:
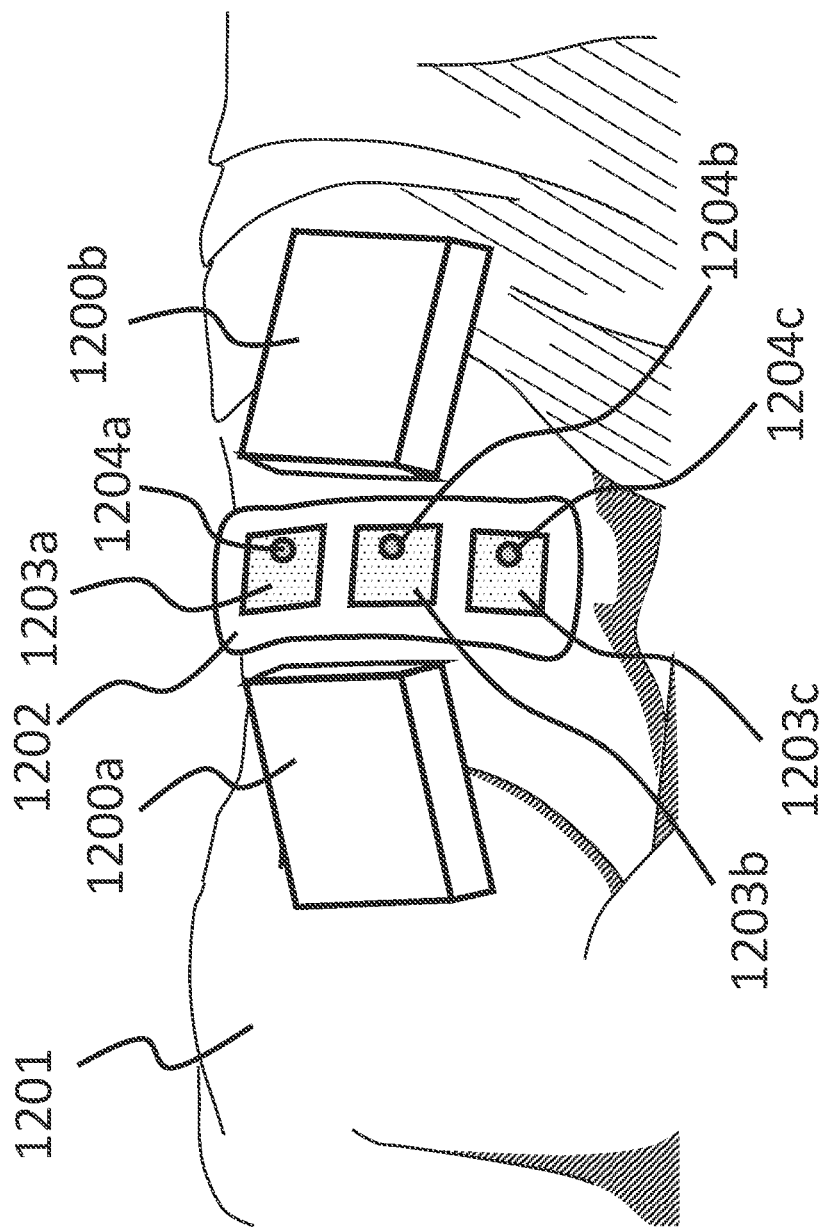
FIG. 12 shows an embodiment in which an array of ultrasound transducers are registered to each other and to gamma camera panels used to scan or treat a patient in combination.

In some embodiments, an array of ultrasound transducers registered to each other and to other sensors, such as to gamma camera panels, could be used instead of a single ultrasound transducer probe. Such array could extend the volumetric area that can be imaged by a co-registered ultrasound imaging system. FIG. 12 shows a depiction of such a system. Gamma camera panels (1200a) and (1200b) are shown scanning a patient (1201). A flexible band (1202) that conforms the outline of the patient's body comprises at least an ultrasound transducer, 3 of them in this depiction (1203a-c). These ultrasonic transducers image the patient (1201) by having ultrasonic contact to the body of the patient. Their position and orientation with respect to each other and with respect to the gamma camera panels (1200a) and (1200b) are tracked by using tracking sensors (1204a-c). Such tracking sensors can be: electromagnetic sensors, optical fiducial markers identifiable by an optical system, ultrasound fiducial markers or sensors, infrared reflective markers, active optical emitting markers, or any other component that can be used to track the position and orientation of the ultrasound transducers with respect to each other. These ultrasound transducers can be used, separately or in combination, to insonificate the body of the patient and to sense the reflected ultrasound waves in order to obtain a significant ultrasonic 3D field of view. Such large 3D field of view can overlap significantly with the gamma camera field of view, which will allow for much more precise tissue deformation corrections, as described in FIG. 8.

Moreover, during the reconstruction of the SPECT image, the computer can analyze the ultrasound image associated with each gamma camera detection to compute the attenuation probability through the tissue of the detected gamma-ray. This calculation requires a knowledge of a detailed map of tissue attenuation coefficients. Because ultrasound images do not directly provide information about tissue type, an automated ultrasound tissue characterization modelling, such as using a machine learning modelling method, can be applied onto the ultrasound image dataset to extract a map of gamma attenuation factors. Tissue types, such as water, fat, muscle, bone, or air-filled areas could be extracted. Standard gamma-ray attenuation coefficients associated with each of these components can be used to build a gamma-ray attenuation map inside the patient's body. By using regularly updated ultrasound images, this attenuation map can be regularly remapped as tissue and organ deformations may occur. Since the ultrasound signal does not propagate well in bone and air, the map of these components inside the patient can be extracted by tracing adjacent tissue that is well visible in the ultrasound image. Other anatomical priors could be used to aid the tissue characterization process and the mapping of the gamma attenuation coefficients. An example of prior maps are CT images, which robustly characterize gamma ray attenuation features that are both well visible and less visible to ultrasound.

The embodiment described in FIG. 12 can also be used for precise intervention guidance. The large 3D ultrasound field of views combined with SPECT images corrected for tissue deformations and for gamma attenuation coefficient variations inside the body of the patient can create a very accurate guidance system for percutaneous biopsies or other interventions, such as ablation treatments.

In some embodiments, the ultrasound transducers (1203a-c) could be used to deliver a high intensity focused ultrasound beam to a region of interest, as highlighted by the SPECT and/or ultrasound image. Such beam could be used for various purposes, such as to ablate tumors, to allow better pharmaceutical drug penetration in a tissue of interest, and to create other physico-chemical changes in a tissue of interest.

In some embodiments, the ultrasound transducers may not reside within the same flexible band (1202), and they may be affixed to the patient independently of each other. However, they may still be tracked with respect to each other and with respect to other points of reference, and may be used in combination to create a large 3D ultrasound image in an area of interest.

In some embodiments, the structure comprising the ultrasound transducers, such as the flexible band (1202) may have an affixing mechanism that keeps the transducer (1203a-c) well connected to the body of the patient without the intervention of a user. For example, such affixing mechanism can be a mechanical arm or an adhesive tape.

Figure 13:
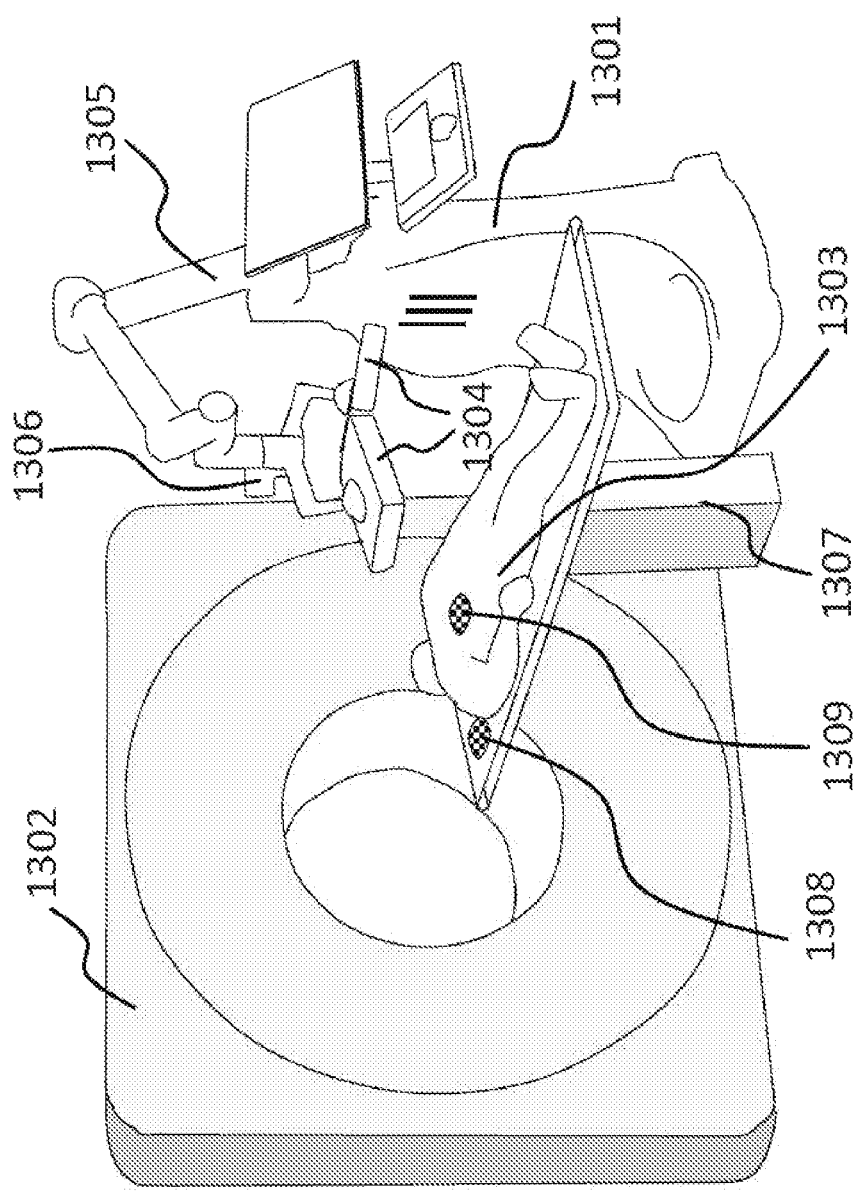
FIG. 13 shows a depiction of a portable SPECT system used in combination with a separate medical imaging system, such as a CT scanner.

For some uses, it may be beneficial to have the SPECT image co-registered to other imaging modalities, such as MRI or CT. FIG. 13 shows a depiction of a portable SPECT system used in combination with a separate medical imaging system. In some implementations, the portable SPECT system (1301) may be moved in close proximity to another medical imaging instrument (1302), such as a CT, Mill, or a magnetic imaging system. This will allow the portable SPECT system (1301) to scan the patient (1303) at the same time or shortly before or after an imaging done with system (1302). The portable imaging system (1301) that can be SPECT or another imaging modality, may comprise imaging sensor panels (1304) attached at the distal end of an articulated arm (1305). In a preferred embodiment, the articulated arm is a 6 or 7 degree of freedom (DOF) robotic arm. The scanning assembly comprises a computer vision camera system (1306). The computer vision camera system is co-registered to the sensor panels by using the computer vision system itself, by mechanical co-registration, or by using other trackers. The computer vision camera can be located within a single housing or its components and sensors can be distributed among several housings and parts of the scanning system (1301). In some embodiments, components of the computer vision system can be placed inside the sensor panels (1304). In a preferred implementation, a part of the computer vision camera system (1306) is attached at the distal end of the articulated arm, having a field of view that covers a part of the patient. In other implementations, a part of the computer vision camera system may be placed elsewhere, and may just have a field of view that covers part of the patient. The computer vision system (1306) is understood as any system that can create images, streams of images, ranging data, and streams of ranging data that are analyzed by a operationally connected computer, and may comprise a RGB camera, an infrared camera, a depth imaging optical camera, a stereoscopic optical camera, a time-of-flight optical camera, a terahertz emitter-sensor assembly, an ultrasound emitted-sensor assembly, another tracking and/or mapping sensor, or a combination thereof.

As one part of the process, the patient (1303) is being scanned by scanner (1302) by being laid down on a scanning table (1306). The table may insert the patient into the scanner and a scan will take place. The image reconstructed by scanner (1302) will be read by a computer that is operationally coupled to the scanner (1301). As another part of the process, the scanner assembly (1301) scans the patient (1303) to create another imaging dataset. This scan can take place concurrently with, before, or after the scan taken by scanner (1302). The computer operationally coupled to the scanner (1301) can analyze the reconstructed image from scanner (1302) to identify structures used for co-registration between the two image datasets created by scanners (1301) and (1302).

Figure 14:
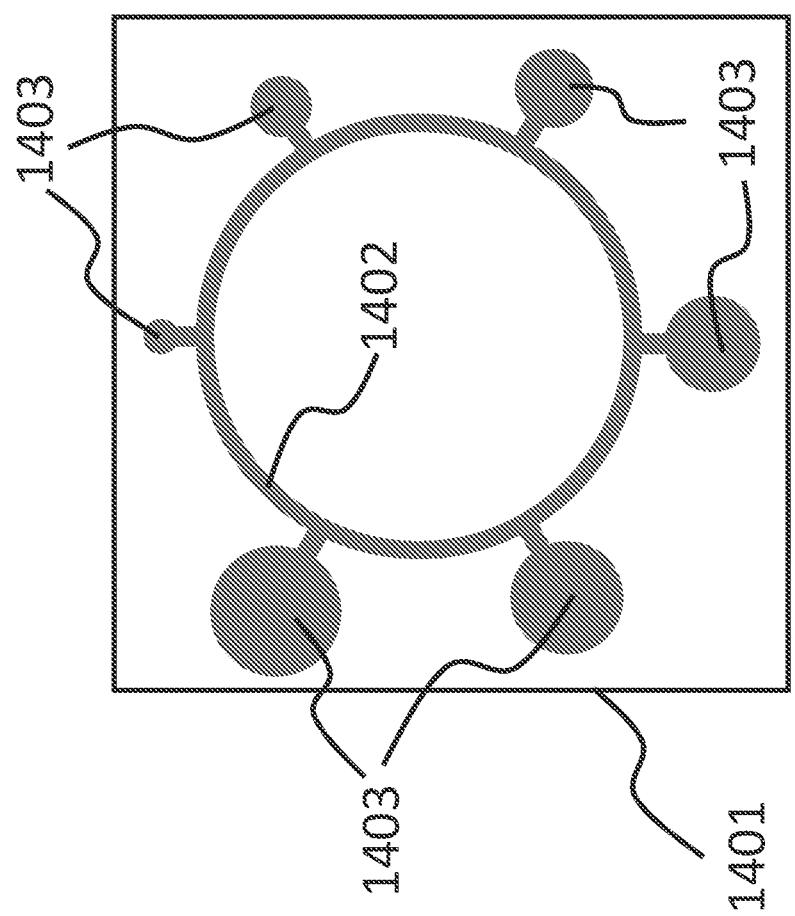
FIG. 14 shows a depiction of a fiducial used to provide co-registration between a portable SPECT system and another medical imaging scanner.

In some implementations, tags (1308) and (1309) may be placed adjacent to the patient before scanning the patient, either by placing the tag (1308) on the table, or by placing the tag (1309) on the body of the patient. These tags may contain features identifiable by both scanner (1302) and system (1301). An embodiment for these tags are depicted in FIG. 14. Structures that are part of the tags (1308) and (1309) and that are imaged by the scanner (1302) will be matched to structures in the computer memory to determine a coordinate system associated with the image dataset delivered by system (1302). Structures that are part of tags (1308) and (1309) and that can be imaged by the computer vision camera (1306) are analyzed by the computer operationally connected to system (1301) and matched to structures in the computer memory to determine a transform between the tag coordinate system and the camera. Furthermore, using the known transform between the camera and the sensor panels (1304), the operationally coupled computer can determine a transform between the coordinate system associated with the image dataset delivered by system (1302) and the coordinate system associated with the image dataset delivered by system (1301). Once the transform is known, data delivered by system (1302) can be used by system (1301) to compute the attenuation map and better reconstruct the location of targets within the body using techniques known in the field (e.g., SPECT-CT).

A distinctly novel use of the transform communicated herein arises through computation of the features common to the data delivered by system (1302) and the system (1301) when operationally coupled to an ultrasound transducer (802). In this embodiment, the system (1301) computes a deformed attenuation model to account for various tissue deformations as described above.

Figure 15:
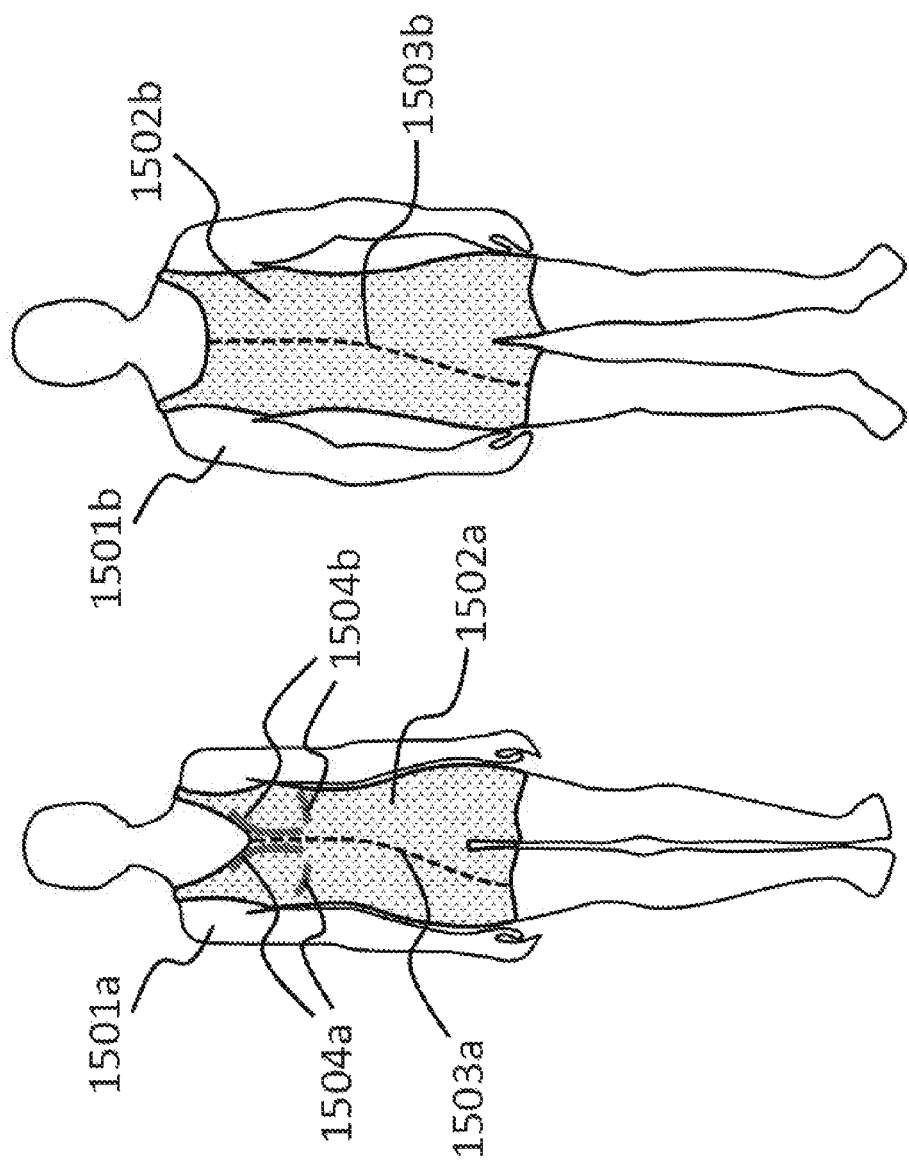
FIG. 15 shows a depiction of body fitted garments that can be used by patients to aid with optical based computer vision tracking and mapping processes.

In some implementations, the patient may have the skin exposed on a part of the body being predominantly scanned by scanner (1302). Additionally, in some implementations, the patient may wear garments that are fitted tightly to the body, as depicted in FIG. 15. This will allow computer vision systems based on optical sensors, or based on sensors that detect signals that do not penetrate cloth, to create an accurate 3D model of the outline of the body of the patient. In some other implementations, the patient may wear regular loose fit hospital gowns. In such implementations, the computer vision system may comprise a cloth penetrating scanning system, such as an ultrasound scanning system, a terahertz scanning system, or a low dose soft x-ray backscatter system to create a 3D model of the outline of the body of the patient.

When the data from computer vision system (1306) can be used by the operationally coupled computer to create a 3D model of the body of the patient, the scanner (1302) preferably is able to deliver maps of anatomical structures, including differentiating between patient's body and air. In this case, the computer operationally connected with scanner (1301) can then analyze the structures in the image dataset provided by scanner (1302) and that are associated with the outline of the body of the patient, and match them to the 3D model of the patient created by the computer vision camera (1306). This will allow the computer to create a co-registration transform between the two imaging datasets and to map the imaging data created by scanner (1302), including anatomical imaging data, into the reference system associated with the imaging data created by scanner (1301) to create a co-registered anatomical map. The co-registration transform can be the result of an iterative algorithm that searches for the best transform that applied to one of the models minimizes the distance error between the two models. When the distance between the two 3D models is minimal, it is assumed that the overlap is maximum and the models are aligned. An example of such an algorithm is the Iterative Closest Point (ICP) or the Generalized-ICP. ICP is described in Chen, Y., & Medioni, G. G. (1992). Object modeling by registration of multiple range images. Image Vision Comput., 10(3), 145-155. Generalized-ICP is described in Segal, A., Haehnel, D., & Thrun, S. (2009, June). Generalized-icp. In Robotics: science and systems (Vol. 2, No. 4, p. 435).

In some cases, there may be systematic deviations between the two 3D models of the patient's body. Some of these deviations may take place because of some patient body movements or body deformations that can take place between the moment the 3D scan is performed with the computer vision system (1306) and the moment the imaging scan is performed with the scanner (1302). In such cases, non-rigid 3D matching algorithms can be used to re-map the image dataset created by scanner (1302), including the anatomical image dataset, to the 3D model delivered by the computer vision system (1306) to create a coregistered deformable anatomical map. Those algorithms may compute a co-registration transform between the two 3D models, as well as they may map the 3D model deformations. This is achieved by allowing different parts of the 3D model to move non-rigidly, while trying to minimize the distance error. The algorithm ensures smooth motion between model parts and as rigid as possible deformations. An example of such an algorithm is the Dynamic Fusion, as described in Newcombe, R. A., Fox, D., & Seitz, S. M. (2015). Dynamic Fusion: Reconstruction and tracking of non-rigid scenes in real-time. In Proceedings of the IEEE conference on computer vision and pattern recognition (pp. 343-352).

The co-registered rigid or deformable anatomical maps can be used by the operationally coupled computer in the process of reconstructing the image created by the scanner (1301). For example, the co-registered anatomical map, such as delivered by a CT scanner (1302), can be used to create a gamma-ray photon attenuation map that can be further used by the operationally coupled computer to improve the quality of the reconstructed image created by a SPECT or PET scanner (1301). For example, the attenuation maps are used to quantify the propagation, or the probability of absorption, or transmission, of photons from specific imaging elements, such as voxels or grid points, to the sensors in the panels (1304). Such attenuation correction processes are currently performed in integrated SPECT/CT systems. For co-registered deformable anatomical maps, it is particularly important to model the deformation of bones and low density volumes, such as lungs, for an accurate photon attenuation correction in the SPECT or PET image reconstruction.

In some implementations, the anatomical map may be done in a separate scanning session. In such cases, the patient may have moved significantly between the anatomical scanning session, such as performed by a CT or magnetic resonance imaging (MRI) scanner (1302), and a molecular imaging scanning session, such as performed with the portable system (1301). In this case, the deviation between the 3D body model extracted from the anatomical data and the 3D body model delivered by the computer vision system (1306) may too large to create an accurate coregistered deformable anatomical map. In this case, an ultrasound probe co-registered to the computer vision system, as described above, can be used to scan the patient at one or more locations to send ultrasound images of the patient to the operationally coupled computer. Structures extracted by the computer from these ultrasound scans can then be matched to structures extracted by the computer from the anatomical maps delivered by scanner (1302) to create co-registration pinning points. These co-registration pinning points will constrain the solution for the deformable co-registration of the anatomical map onto the molecular map. The coregistered deformable anatomical maps can be used for attenuation corrections in the molecular map reconstruction process, as described above.

The coregistered deformable anatomical maps can also be used by the operationally coupled computer to send to a visualization device a rendering of the molecular map provided by scanner (1301) combined with a rendering of the co-registered anatomical map provided by scanner (1302). The computer may also send to the visualization device a rendering of the ultrasound image delivered by the co-registered ultrasound probe combined with a rendering of the anatomical map delivered by the scanner (1302). This process can be done when the scanning sessions performed by scanners (1301) and (1302) are done jointly or separately.

In some implementations, it may be useful to navigate the co-registered anatomical, ultrasound, molecular imaging models, or a combination thereof, augmented onto a live red-green-blue (RGB) image of the patient taken by a camera or onto a user's view by using a head mounted display. In that case, a handheld stylus or probe tracked by the computer vision system can be used by a user to select imaging planes of interest to show a rendering of those imaging datasets in the planes selected with the stylus or probe.

In some other implementations, the computer vision system (1306) may determine its position with respect to scanner (1302) by analyzing geometrical features on the scanner (1302) or by analyzing tags attached to the scanner (1302). This will allow a computer operationally connected to the computer vision camera (1306) to determine the location and orientation of the panels (1304) with respect to the scanner (1302). This, in its return, will allow the computer to perform the co-registration between the image datasets provided by scanner (1301) and scanner (1302).

In some implementations, the scanner (1301) may scan the patient as the table moves the patient through the scanner (1302). In this case, the computer adjusts the scanning protocol in real time to account for the movement of the patient and scanning table as provided by the computer vision system.

FIG. 14 shows a depiction of a fiducial used to provide co-registration between a portable imaging system, as illustrated by (1301) in FIG. 13, and another medical imaging scanner, as illustrated by (1302) in FIG. 13. In an embodiment, the fiducial, whose outline is represented by (1401), may comprise a structure (1402) that is identifiable in the image map delivered by scanner (1302). For example, if the scanner is a CT scanner, the structure (1402) may be made of a material that attenuates X-rays, such as steel, tungsten, or another high density material. The fiducial (1401) may also comprise features (not depicted) that can be identified by the computer vision system (1306), such as binary black and white tags. In the illustration, a ring of known diameter may support a number of protruding geometric shapes (sub-structures) (1403) of various dimensions. These substructures will break the symmetry of the fiducial allowing for an unambiguous identification of the fiducial position and orientation, and it will enable its use with instruments of various imaging performance, such as resolution and contrast. As such, larger structures will be visible in maps delivered by most scanners, whereas smaller structures will add extra benefit for better co-registration for maps delivered by scanners that provide better imaging performance, such as resolution and contrast. The shapes are of a known size and position relative to the center of the ring. In the illustration the shapes are spheres, but may be changed to pyramids, for example, in other embodiments. Analysis of the data from the targeted modality, a computer can calculate the position of the center of the ring by observing the location of the material as well as the orientation of the structure (1402). The fiducial (1401) is constructed with a known transformation between the aspects specifying the position inferred by computer vision techniques and the modality targeted through use of the asymmetric structure (1402)

The position and orientation of endoscopes and cameras guided within them can be inferred using fluoroscopy and techniques established in the field. Using the fiducial (1401) to co-register the SPECT system with the coordinate frame of a Fluoroscopy system, the same computational unit can provide an operator with an augmented view of the internal area of the body viewed by a camera inserted by the endoscope. The augmentation can guide the operator to objects within the body identified by the SPECT imaging system (1301). To achieve this, we can insure that a computational unit is informed of the position and orientation of the camera within (or attached to) the endoscope. The tracked position of the endoscope can be interpreted by the same computational unit using techniques known in the art. Should the endoscope tracking system also be articulated to view a co-registration fiducial (1401), then the computational unit can also compute the position and orientation of the camera attached to or within the endoscope with respect to the coordinate frame chosen by the SPECT system (1301). This is achieved by computing the relative transform between the endoscope fiducial structure(s) and the co-registration fiducial (1401). This sequence of transformations allows the computational unit to overlay the reconstructed SPECT image onto that acquired by the endoscope camera. This information is particularly useful in guiding interventions such as lung biopsies where ultrasound cannot offer real-time guidance.

The endoscope described above may contain instruments and tools capable of ablation, drilling, cutting, piercing, debriding, or accessing targets identified by the SPECT imaging system. These tools can be articulated by the operator and monitored by the visualizations provided by the endoscope camera augmented by the computational unit informed of SPECT targets as described above.

Data from the camera or other computer vision system inserted within the endoscope can also be used to observe and measure tissue deformations through computational processes. Because of the co-registration described joining the computer vision system within the endoscope with the position of the SPECT system, these tissue deformations can also inform the SPECT reconstruction by applying the inferred deformation transformations to the attenuation map. Updating the attenuation map is important when computing real- or near-real-time SPECT images. Similarly, the tissue deformations inferred by sensors within the tracked endoscope can be used to compute accurate updates to visualizations of SPECT targets previously reconstructed within the body as described above. These updates can be presented as overlays or augmentations to images captured by the sensors on or within the endoscope. These updates can also be presented by the SPECT visualization monitor (1009) to guide interventions visualized through other co-registered sensors.

FIG. 15 shows a depiction of body fitted garments that can be used by patients to aid with optical based computer vision tracking and mapping processes. Patients that can be either females (1501a) or males (1501b) may wear garments (1502a) and (1502b) that closely follow the contour of the body. For example, the garments may be made of a stretchable cloth material. The garments may be made of a material that allows for the ultrasound waves to pass essentially undisturbed through the garments, especially in combination with ultrasound conducting gel. The garment material can be chosen so that, when combined with ultrasound conductive gel, the garment will provide reduced acoustic impedance and reflections for typical medical ultrasound frequencies. The garment material may comprise through-holes that allow the ultrasound gel to go through them and reach the skin of the patient after having it applied on the garment. This may enable a superior transmission of ultrasound waves.

In some implementations, the garments may only cover the upper body, such as torso. In other embodiments they may only cover part of the legs, hips and waist, similarly to swimming shorts. In some other implementations, the garment may cover both hips, waist and torso (as illustrated). The garments may or may not cover a significant part of the legs and arms. The garments may be taken on and off similarly to swimsuits. In some implementations, the garments may be closed by binders (1503a) and (1503b). These binders may be selected from a group containing zippers, buttons, adhesive bands, hook-and-loop fasteners, or a combination thereof. Adhesive tapes (1504a) and (1504b) may be used to ensure that the garment follows the skin of the patient in locations that may be elevated from the skin. Such adhesive tapes can be part of the garment, or can be applied separately. In some implementations, the adhesive tape has both sides adhesive. This double sided adhesive tape may be mounted on the skin at specific places before taking the garment on, and pressing the garment onto the tape to secure its proximity to the skin.

In some embodiments, these garments may comprise prints or patterns. Such geometrical features that may be recognized and tracked by a computer vision analysis program in a computer operationally coupled to the computer vision system to create a 3D model of the patient by tracking the prints or pattern features. For that purpose, structure from motion algorithms (as described in Fuhrmann, S., Langguth, F., & Goesele, M, Mve-a multi-view reconstruction environment, in GCH pp. 11-18 (2014, October); Ummenhofer, B., Zhou, H., Uhrig, J., Mayer, N., Ilg, E., Dosovitskiy, A., & Brox, T., Demon: Depth and motion network for learning monocular stereo, in *Proceedings of the IEEE Conference on Computer Vision and Pattern Recognition*, pp. 5038-5047 (2017).) may be used with a monocular camera. Structure matching algorithms may be used with stereoscopic cameras. Structure matching algorithms are described in Hirschmuller, H, Stereo processing by semi-global matching and mutual information, *IEEE Transactions on pattern analysis and machine intelligence*, _30_(2), 328-341 (2007); Sun, J., Zheng, N. N., & Shum, H. Y., Stereo matching using belief propagation, *IEEE Transactions on pattern analysis and machine intelligence*, _25_(7), 787-800 (2003); Geiger, A., Roser, M., & Urtasun, R., Efficient large-scale stereo matching, in *Asian conference on computer vision* (pp. 25-38). Springer, Berlin, Heidelberg (2010, November).

These garments can be used to allow a computer vision system create an accurate 3D map of the outline of the patient without requiring the patient to expose skin over large areas of the body, allowing the patient to stay warm and comfortable. Another benefit of these garments is to keep compressed areas of the patient's body that otherwise may be loose. Another benefit of these garments is to allow convenient ultrasound examinations with co-registered ultrasound probes.

Figure 16:
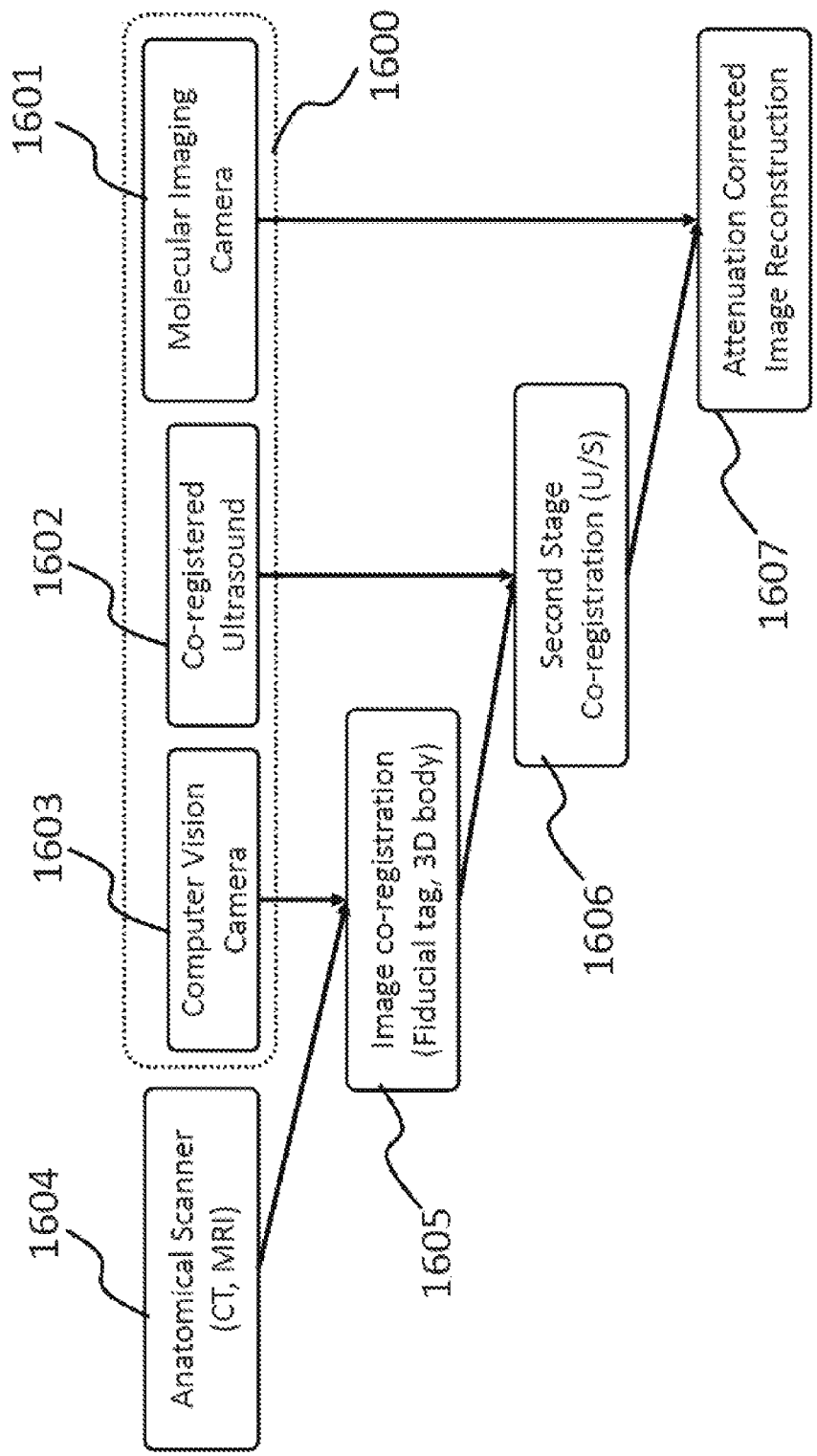
FIG. 16 shows a processing workflow of importing other imaging datasets to deliver multi-modality image fusion and to improve SPECT reconstructions.

FIG. 16 shows a processing workflow of importing other imaging datasets to deliver multi-modality image fusion and to improve SPECT reconstructions. The portable imaging instrument (1600) may comprise a molecular imaging camera system (1601), a co-registered ultrasound system (1602), and a co-registered computer vision camera (1603). Anatomical image data is delivered by another medical imaging scanner (1604). The scanner (1604) can be CT, MM, or another imaging system able to provide anatomical data in 3D. In a preferred implementation, scanner (1604) is a CT scanner. A computer operationally connected to the computer vision camera analyzes data from the computer vision camera to create a computer vision generated 3D model of the body of the patient. The computer also analyzes data from the scanner (1604) to extract an anatomical image generated 3D model of the body of the patient. In process (1605) the computer vision generated 3D model is compared to the anatomical imager generated 3D model to create a co-registration mapping between the two image datasets. This coregistration mapping can perform a rigid co-registration or a deformable co-registration. This creates a pre-coregistered anatomical image dataset. In some cases, a second stage coregistration (1606) can take place, in which a co-registered ultrasound probe connected to the ultrasound system (1602) performs a scan at one or more locations on the body of the patient. The computer analyzes the ultrasound scan to identify ultrasound generated anatomical features and to match these features with internal anatomical features in the pre-coregistered anatomical image dataset. This creates anchor points where specific internal anatomical features in the pre-coregistered anatomical image dataset are assigned 3D locations that equates their positions in the ultrasound image. The computer will use these anchor points to constrain the deformable co-registration solution and to iterate on the pre-coregistered anatomical image dataset. This will create a coregistered anatomical image dataset. In the process (1607) the computer loads the molecular imaging data from (1601) and the pre-coregistered anatomical image dataset or the coregistered anatomical image dataset to reconstruct a molecular image using attenuation maps extracted from the anatomical datasets. The computer can send to a visualization device a rendering or a combination of renderings of the ensuing molecular image, coregistered anatomical images and ultrasound scans.

In some embodiments the computer vision system (or parts of it) may not be attached to the assembly (1301). In this case, the computer vision system may monitor not only the tag and/or patient, but also components of the scanner (1301), or fiducials that may be mounted on parts connected to the cart (1301), panels (1306), robotic arm (1305), or other components. This will enable the co-registration of the sensor panels with respect to the computer vision camera, and with respect to the patient or to the fiducial tag (1308) and (1309). Alternatively, the computer vision camera may be tracked by another tracking system that allows the co-registration between the computer vision camera and the molecular imaging system.

Figure 17:
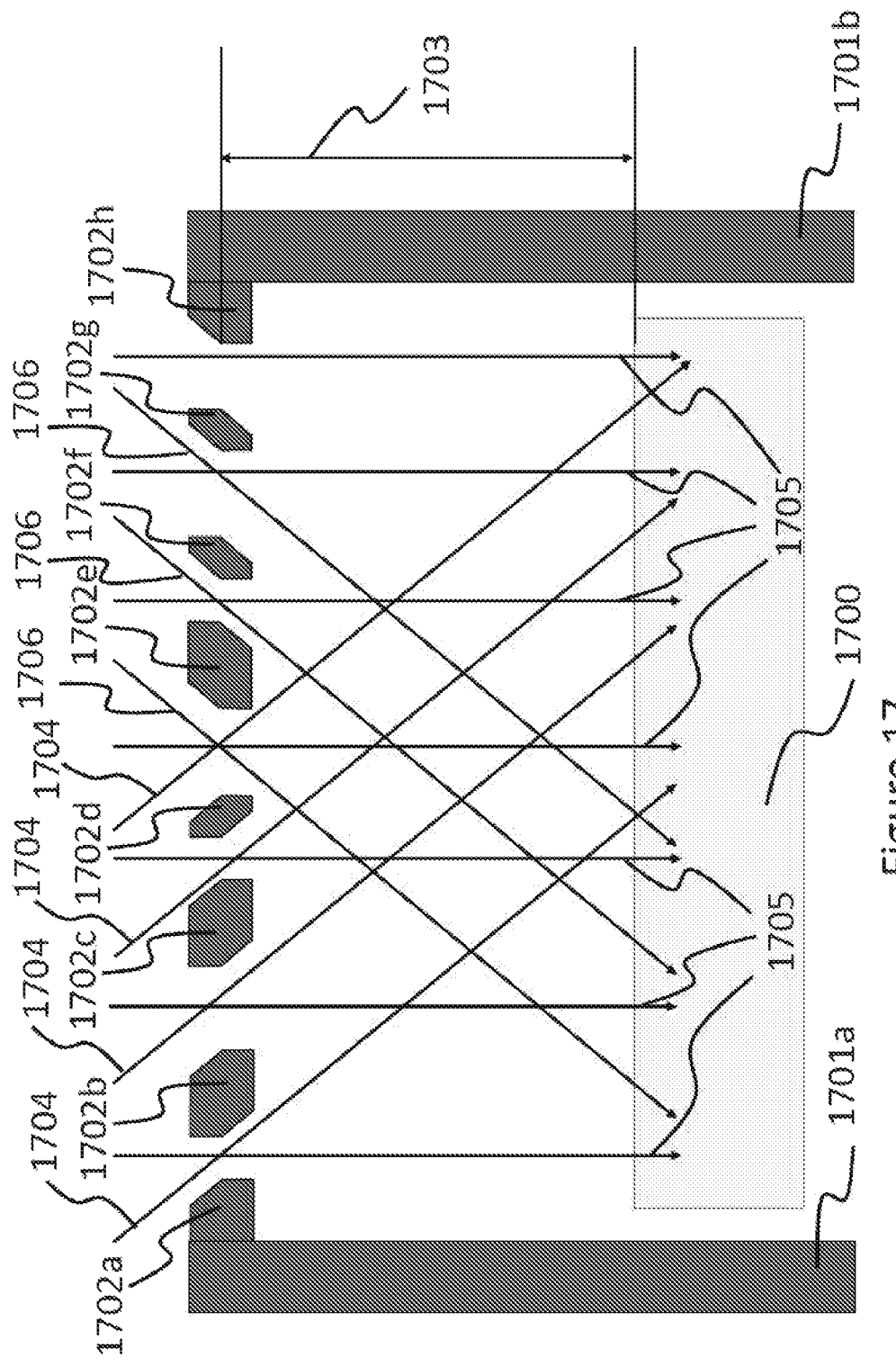
FIG. 17 shows a sectional side view of the large field of view coded aperture imaging system.

FIG. 17 shows a sectional side view of an embodiment of a large field of view coded aperture imaging system. This image shows techniques to enable large field of view imaging using mask elements with multiplane side faces. The position sensitive sensor (1700) is shielded on some sides not covered by the coded aperture by shields (1701*a*) and (1701*b*). The large-field-of-view, coded-aperture mask comprises elements (1702*a*)-(1702*h*). The plane of the mask is placed at a distance (1703) away from the face of the position sensitive sensor (1700). Each individual mask element pixel has multi-planar side faces that allows coding of photons from a range of directions. For example, in this embodiment, mask elements on the left side (1702*a*)-(1702*d*) allow photon fluxes from directions (7104) at around −45° from the mask normal to be coded based on their angle and sensed by the sensor (1700). These elements also allow for photons fluxes from directions (1705) close to the normal of the mask to be coded based on their angle and sensed by the sensor (1700). Likewise, mask elements on the right side (1702*e*)-(1702*h*) allow photon fluxes from directions (1706) at around 45° from the mask normal to be coded based on their angle and sensed by the sensor (1700). These elements also allow for photons fluxes from directions (1705) close to the normal of the mask to be coded based on their angle and sensed by the sensor (1700). With this type of mask configuration, imaging with high sensitivity can take place for angles from around −45° to around 45° with respect to the normal onto the mask plane. Similar mask element shaping and coding can take place in the other perpendicular direction (normal onto the plane of this illustration section). For example, the mask elements can be made of a rigid high density, high atomic mass material, such as tungsten or tungsten alloy.

Figure 18:
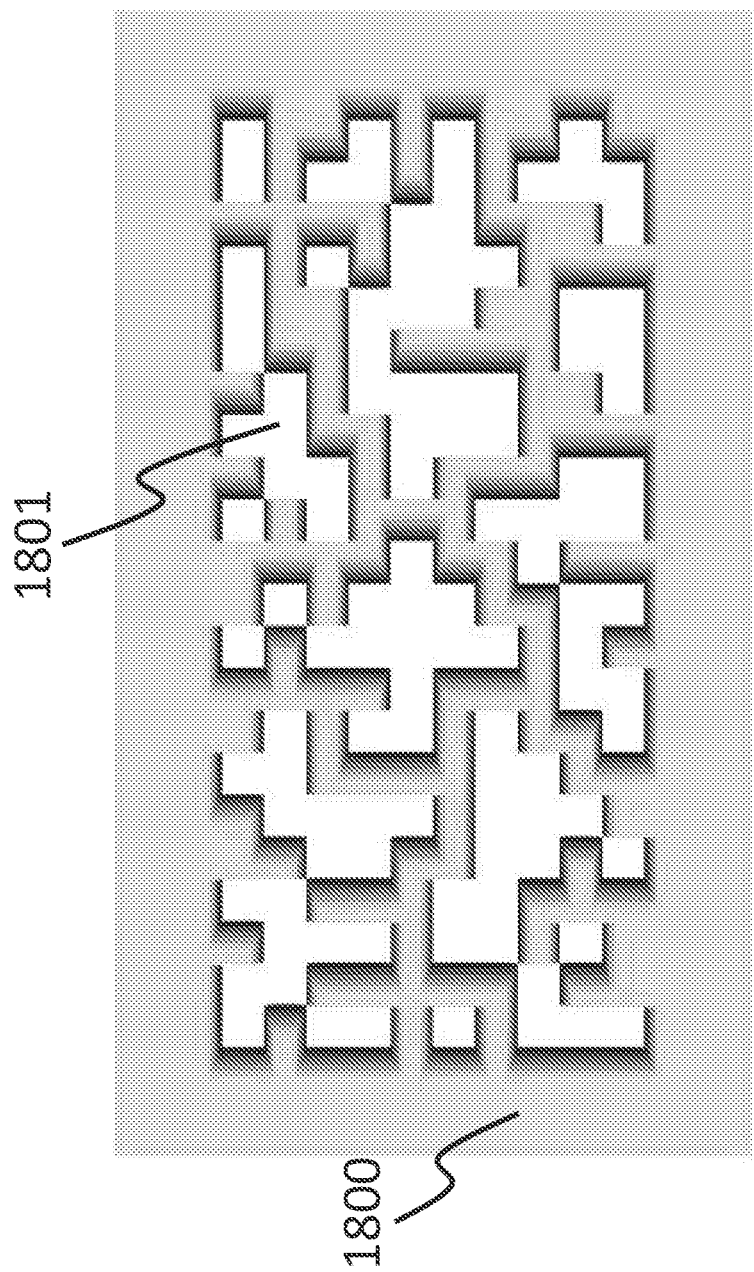
FIG. 18 shows a front view of the large field of view coded aperture mask.

FIG. 18 presents a top view of a large field of view coded mask (1800). Various shades of gray show different depths along the direction normal onto the mask plane. Holes, or openings, into the mask are represented by white areas, such as (1801). Identical holes arranged in a regular repeating pattern are advised against, as may create reconstruction artifacts.

Figure 19:
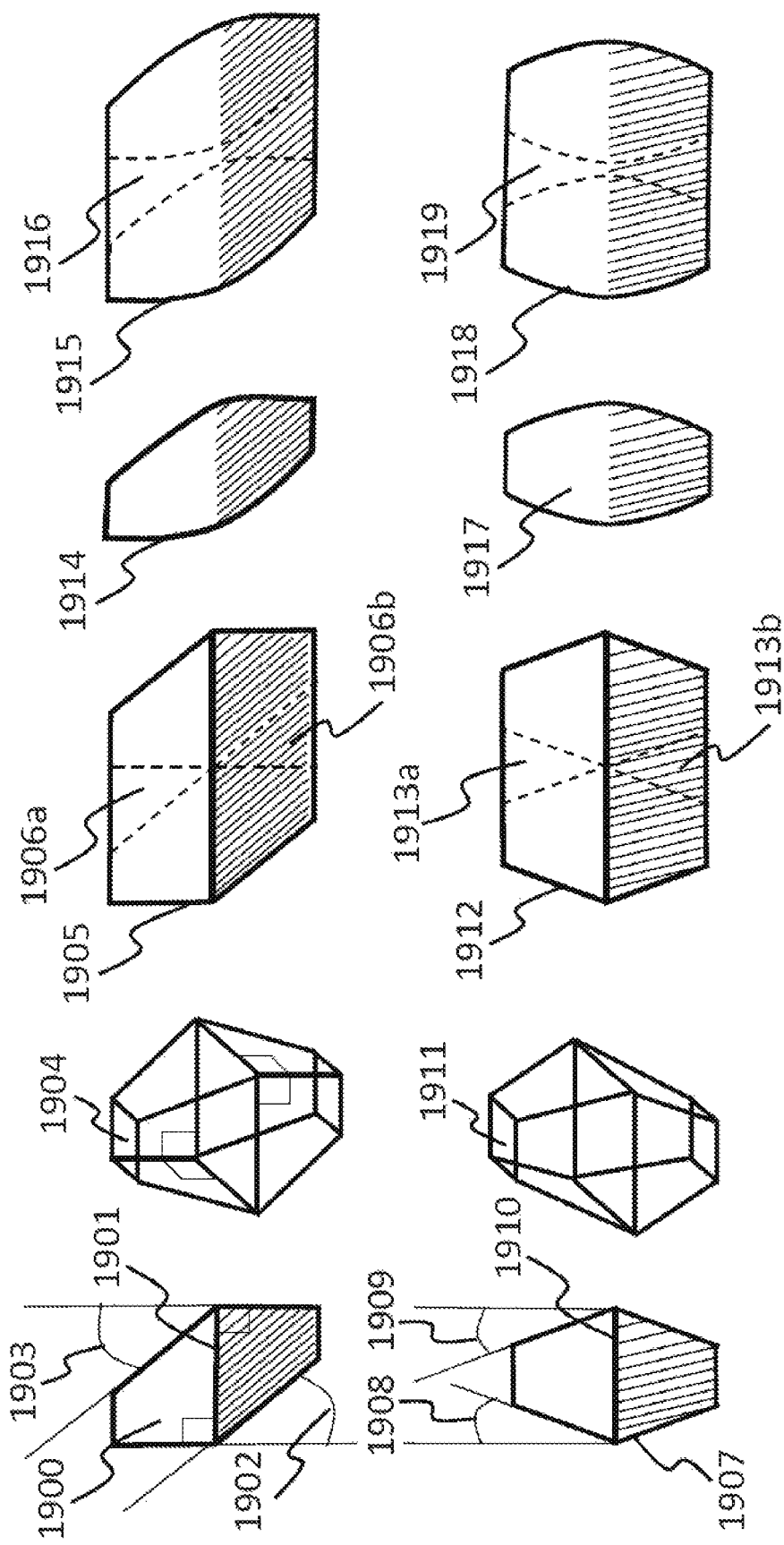
FIG. 19 shows a profile view of the mask elements.

FIG. 19 shows various views and geometries of the pixel elements in a mask with square or rectangular pixels. A bifrustum mask pixel element is shown in a side view (1900). The square or rectangular base (1901) effectively defines the extent of the mask pixel within the mask plane. In this particular embodiment, the plane of the bifrustum base is parallel to the mask plane. The side faces of the bifrustum can be perpendicular to the base of the bifrustum, or can form various angles (1902) and (1903) with respect to the normal to the base plane. In some embodiments, the angles (1902) and (1903) have values larger than 10 degrees. As such, the bifrustum shaped mask pixel elements have at least a side face making an angle larger than 10 degrees with respect to the normal on the bifrustum base. In some embodiments, the angles (1902) and (1903) have values smaller than 60 degrees.

The pixel element can have a similar profile when seen from the side in the perpendicular direction, or can have side faces that make other angles with the normal to the base plane. (1904) represents a 3D view of a rectangular bifrustum symmetric with respect to the center of the rectangular base, and with a straight edge. This is just a representative example, and other bifrustum geometries can be used. In some embodiments, when two mask pixels have a common edge, the immediate space between the two bifrustums may be filled in with attenuation material. Two adjacent bifrustums (1905) can be seen forming gaps (1906*a*) and (1906*b*) defined by the area between the dashed lines, as shown in FIG. 19. In some embodiments, these gaps are filled with attenuation material. Certain mask pixel element bifrustums may also have a profile (1907) in which the side faces make the same angle (1908) and (1909) with respect to the normal on the base plane (1910).

In some embodiments, certain mask pixel bifrustums can have a side view similar to (1900), the other as (1900), or a side view as (1900), the other as (1907), or a side view as (1907), the other as (1907). This last case is represented by the (1911) 3D view, which is basically a symmetric bifrustum of a right rectangular pyramid. Two adjacent bifrustums (1911) can be seen forming gaps (1913*a*) and (1913*b*) defined in the figure by the area between the dashed lines. In some embodiments, these gaps are filled partially or completely with attenuation material.

In some embodiments, instead of using pixel mask elements shaped as bifrustums with planar side faces, the pixel elements can comprise rounded faces that substantially capture the attenuation profile of a bifrustum with planar faces. A pixel element with rounded faces with a profile (1914), as shown in FIG. 19, may provide a similar attenuation characteristics as the bifrustum with the profile (1900). In some embodiments, when two such pixel elements have an adjacent of common edge as seen in (1915), the gap (1916) between the two pixel elements is filled with attenuation material. Similarly, a pixel element with rounded faces with a profile as shown in (1917) provides substantially a similar attenuation characteristics as the bifrustum with the profile (1911). In some embodiments, when two such pixel elements have an adjacent of common edge as seen in (1918), the gap (1919) between the two pixel elements is filled with attenuation material.

In other embodiments, the side faces of the mask pixel elements and filling between the mask elements can have a staircase-like appearance, or can have other micro-structures that substantially follow macroscopic profiles similar to profiles (1900), (1905), (1907), (1912), (1914), (1916), (1917), and (1918).

In an embodiment, the mask pixel elements and the filling attenuating material between the mask pixel elements are made of materials of densities above 10 g/cc.

In some embodiments, the mask pixel elements and the filling attenuating material between the mask pixel elements is made of the same material that is high density, high atomic number Z, such as tungsten or tungsten alloy.

Whereas mask pixel elements shaped as bifrustums with a rectangular base have been depicted, bifrustums with triangular or hexagonal bases can be used as mask pixel elements in mask arrays that comprise triangular or hexagonal pixels, respectively. A single coded aperture mask can combine mask pixels that have different geometrical shapes, such as rectangles, square, triangles or hexagons, and may have various dimensions. Similarly to the rectangular pixels, the triangular or hexagonal bifrustum mask pixel elements may be symmetric with respect to the center of the triangular or hexagonal base, may be symmetric with respect to the triangular or hexagonal base plane, or may not have any symmetries. The shape of the rectangular, triangular or hexagonal bifrustum mask elements may change across the mask. Attenuating material may be used in any of these geometries to fill partially or completely the space between bifrustum shaped mask pixel elements that share a common edge.

Figure 20:
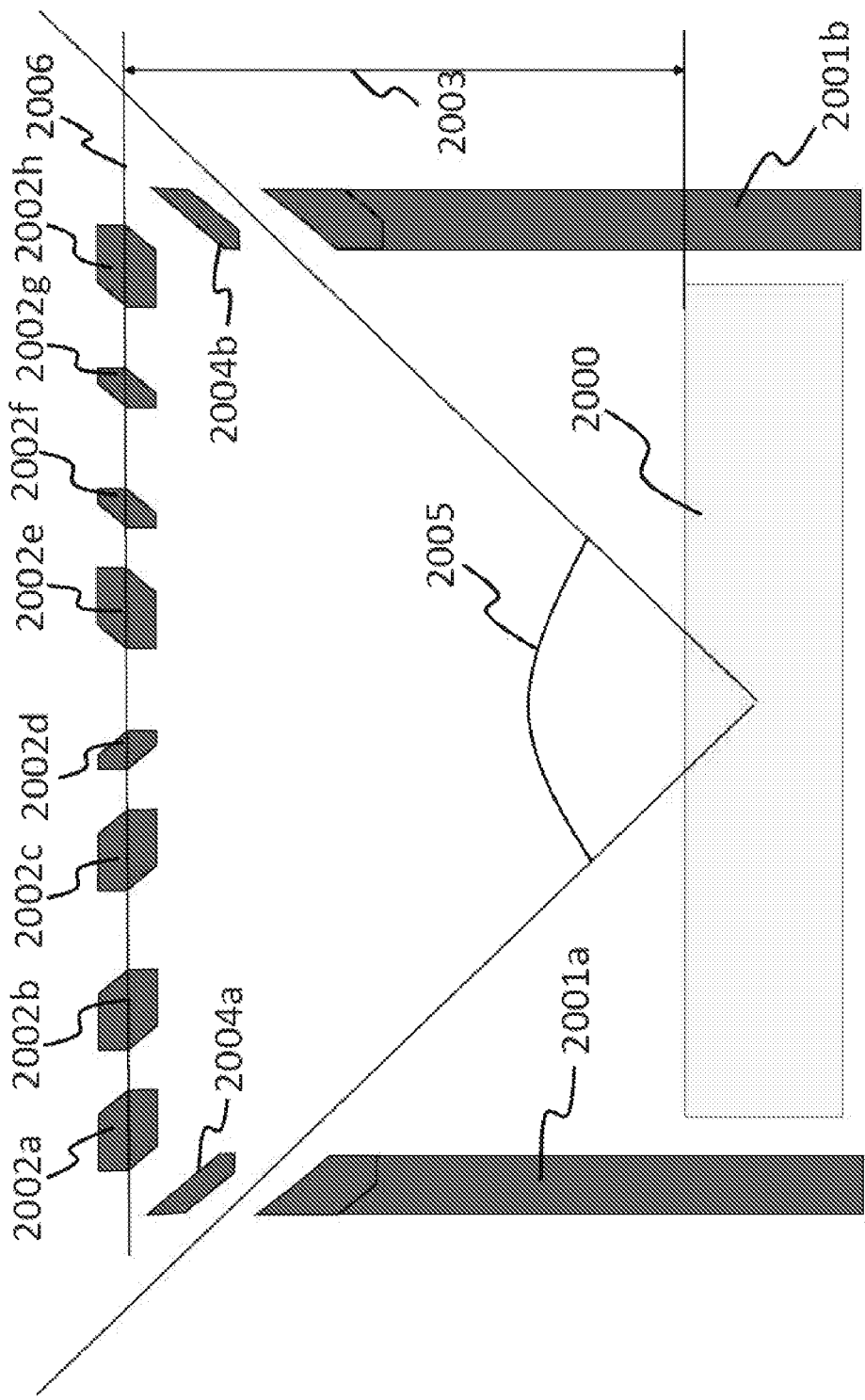
FIG. 20 shows a sectional side view of the large field of view coded aperture imaging system showing the coded aperture mask extend over multiple planes.

FIG. 20 shows an embodiment of a large field of view coded aperture similar to the one shown in FIG. 17, but with the coded aperture extending onto other planes. In this embodiment, the coded aperture extends onto planes perpendicular to the first mask plane. The position sensitive sensor (2000) is shielded on some sides not covered by the coded aperture by shields (2001*a*) and (2001*b*). The coded aperture mask within a first plane comprises elements (2002*a*)-(2002*h*). The first plane of the mask is placed at a distance (2003) away from the face of the position sensitive sensor (2000). In some embodiments, the distance (2003) may be increased to enable increased angular resolution, which may translate into an increased imaging resolution. Mask elements (2004*a*) and (2004*b*) can be positioned in other planes other the first mask plane in order to maintain a large imaging field of view (2005). In some embodiments, a large imaging field of view can be maintained at larger mask-sensor distances (2003) by extending the physical profile of the mask in the mask plane beyond the physical profile of the sensor in the same plane.

The position sensitive senor (2000) can be made of multiple sensor units that are substantially parallel to each other and have faces that are substantially the same plane and parallel to the first mask plane (2006), or they can have sensor units that have their front faces in planes that make angles between 0 degrees to 90 degrees to the first mask plane (2006).

Figure 21:
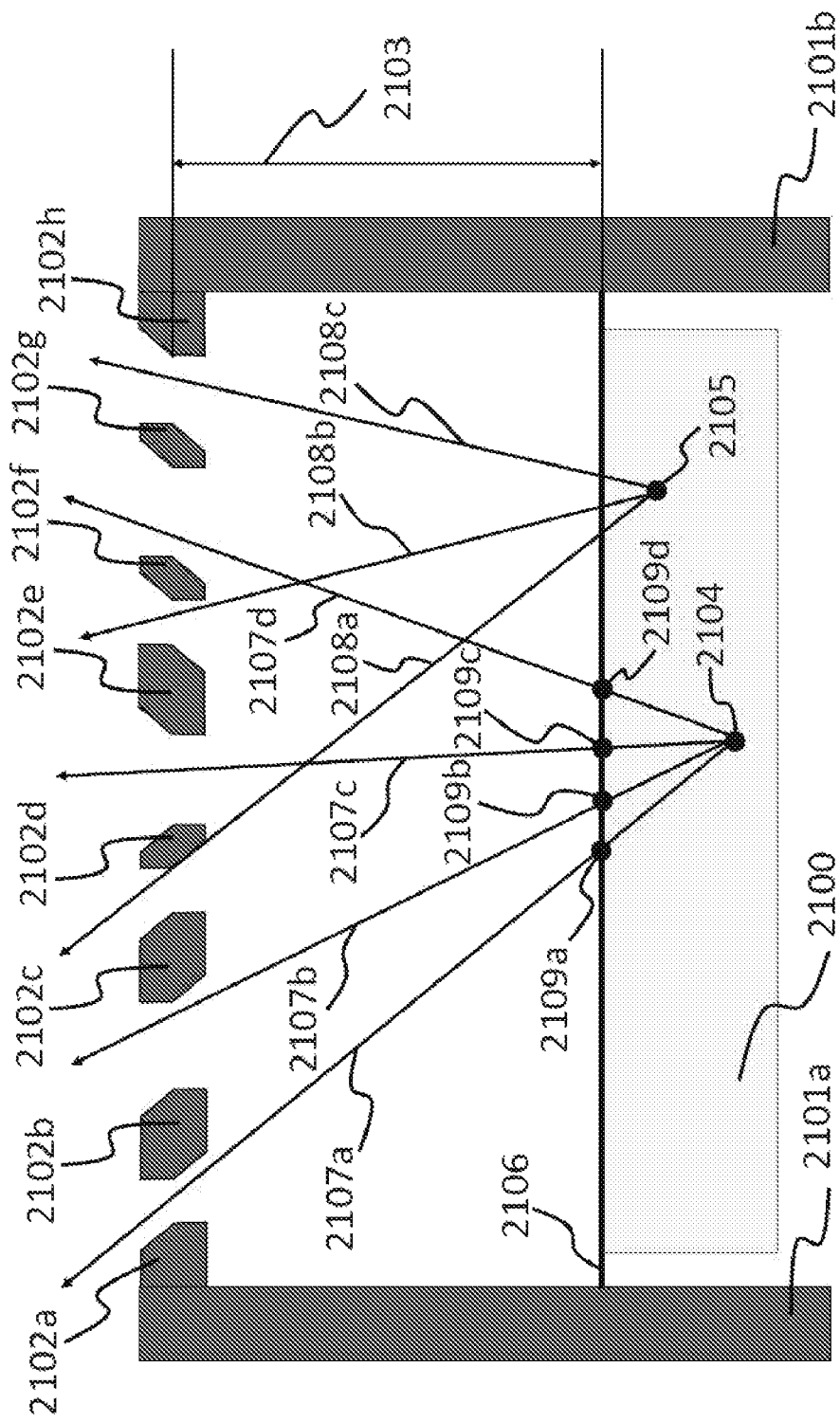
FIG. 21 shows a sectional side view of the large field of view coded aperture imaging system showing how detected events get back-projected into the image space for image reconstruction using a reference plane.

FIG. 21 shows an embodiment of a large field of view coded aperture similar to the one shown in FIG. 17, but in which other components are depicted to support the description of the process by which detection events can be used in the image reconstruction analysis that involves large field of view coded apertures. The position sensitive sensor (2100) is shielded on some sides not covered by the coded aperture by shields (2101*a*) and (2101*b*). The coded aperture mask within a first plane comprises elements (2102*a*)-(2102*h*). The first plane of the mask is placed at a (2103) distance away from the face of the position sensitive sensor (2100). A first radiation interaction (2104) and a second radiation interaction (2105) is detected with position resolution in all three dimensions by the sensor (2100). The sensor (2100) can be a semiconductor detector, such as CdZnTe CdTe, a scintillator detector, such as Na(I), LSO, or any other scintillator material able to provide the position of interaction in 3 dimensions. Position of interaction can be achieved in 2 dimensions by segmenting the readout electrode, by employing position sensitive light detection arrays, by employing signal analysis methods, by creating individual sensor rods with individual signal readout, or a combination of the above. The position of interaction in the third dimension can be achieved by using sensors with depth of interaction capabilities. Certain systems can provide position of interaction in depth for both semiconductor and scintillator sensors.

Once a radiation is detected in 3D, processes may be put in place to use that information to reconstruct the image of the radiotracer distribution with high imaging resolution and sensitivity.

One step towards reconstructing the image is to determine the backprojection operator. The backprojector operator uses the probability density function (pdf) for a detected radiation event to have originated anywhere from the volume external to the coded aperture and shield. In order to calculate the pdf for a detected event, a radiation transmission map, or attenuation coefficients map, through the coded aperture and shielding is determined at the location at which the radiation was detected.

In an embodiment, an attenuation map is pre-calculated across at least a plane (2106) referred to as the instrument response plane of reference, or just the plane of reference. The plane of reference can be parallel to the first mask plane or it can make any angle with the first mask plane. Also, the plane can be attached to any physical component, such as the face of the sensor, the first mask plane, or it can be positioned at any other location in space. For illustrative purposes, in the present drawing the plane of reference is parallel to the first mask plane and it coincides with the face of the sensor. For each point or pixel within the plane of reference, the attenuation map comprises radiation attenuation coefficients, or other information that can be used to extract the attenuation coefficients, such as path lengths through the mask material, for a pre-defined type of radiation for various angles across the coded aperture imaging field of view.

For each radiation detected, the 3D position of the interaction, such as (2104) and (2105) is projected onto the reference plane along the directions towards the coded mask field of view, such as directions (2107*a*)-(2107*d*) for interaction (2104) and directions (2108*a*)-(2108*c*) for interaction (2105). The resulting intersections with the plane of reference (2106) creates points (2109*a*)-(2109*d*) for projecting interaction (2104) along directions (2107*a*)-(2107*d*), respectively. The locations (2109*a*)-(2109*d*) are used to retrieve the attenuation coefficient through the mask along directions (2107*a*)-(2107*d*), respectively. In this example, the path of the radiation along all these directions includes a segment through the sensor from (2104) to (2109*a*)-(2109*d*). This path may not have been captured by the pre-calculated attenuation coefficients at the plane of reference (2106). In some implementations, these paths can be added into the pdf calculation to scale the intensity of the back-projection along each of those directions (2107*a*)-(2107*d*). This process to calculate the backprojection operator is particularly useful when a list-mode image reconstruction algorithm is employed. The pdf calculated from attenuation coefficients for interactions at positions (2104) and (2105) can be employed in the reconstruction of the gamma-ray source image by employing methods commonly used for image reconstruction, such as statistical iterative methods, algebraic iterative methods, analytical methods or compressive sensing methods.

Although this embodiment only depicts a single plane of reference, in other embodiments multiple instrument response planes of reference could be used to increase imaging performance.

Figure 22:
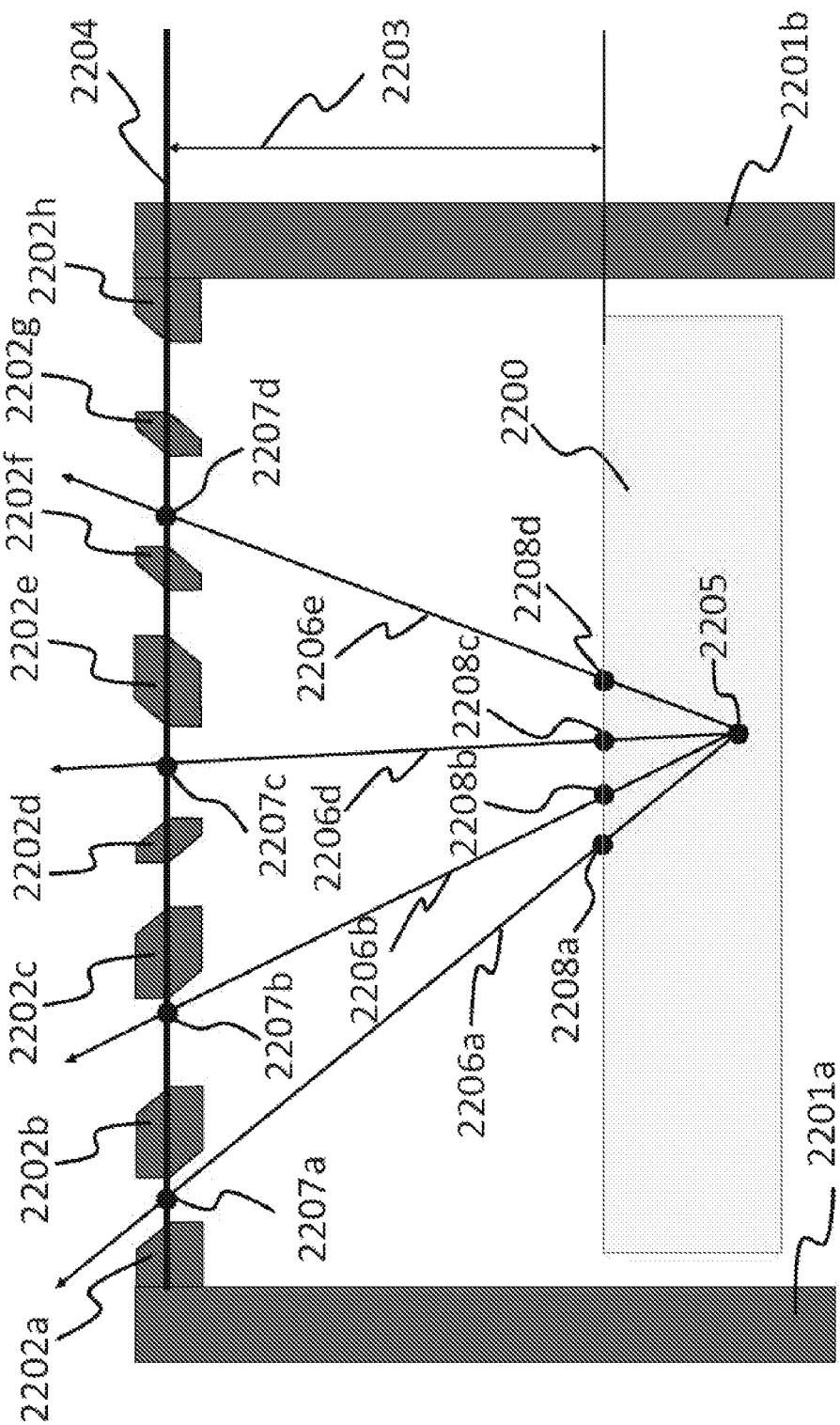
FIG. 22 shows a sectional side view of the large field of view coded aperture imaging system showing how detected events get back-projected into the image space for image reconstruction using a reference plane that coincides with the mask plane.

In other embodiments the plane of reference can be located at other positions. FIG. 22 exemplifies such a case. The position sensitive sensor (2200) is shielded on some sides not covered by the coded aperture by shields (2201*a*) and (2201*b*). The coded aperture mask within a first plane comprises elements (2202*a*)-(2202*h*). The first plane of the mask is placed at a (2203) distance away from the face of the position sensitive sensor (2200). In this case, the instrument response plane of reference (2204) is chosen to be the same as the first mask plane. The 3D position of a radiation interaction (2205) is projected onto the reference plane along relevant directions towards the coded mask field of view, such as directions (2206a)-(2206d). The resulting intersections with the plane of reference (2204) creates points (2207a)-(2207d), respectively. The locations (2207a)-(2207d) are used to retrieve the attenuation coefficient through the mask along directions (2206a)-(2206d), respectively. In this example, the path of the radiation along directions (2206a)-(2206d) includes a segment through the sensor from (2205) to (2208a)-(2208d), respectively. This path may not have been captured by the pre-calculated attenuation coefficients at the plane of reference (2204). In some implementations, these paths can be added into the pdf calculation to scale the intensity of the back-projection along each of those directions (2206a)-(2206d). This process to calculate the backprojection operator is particularly useful when a list-mode image reconstruction algorithm is employed in the reconstruction of the radioactive source distribution.

Figure 23:
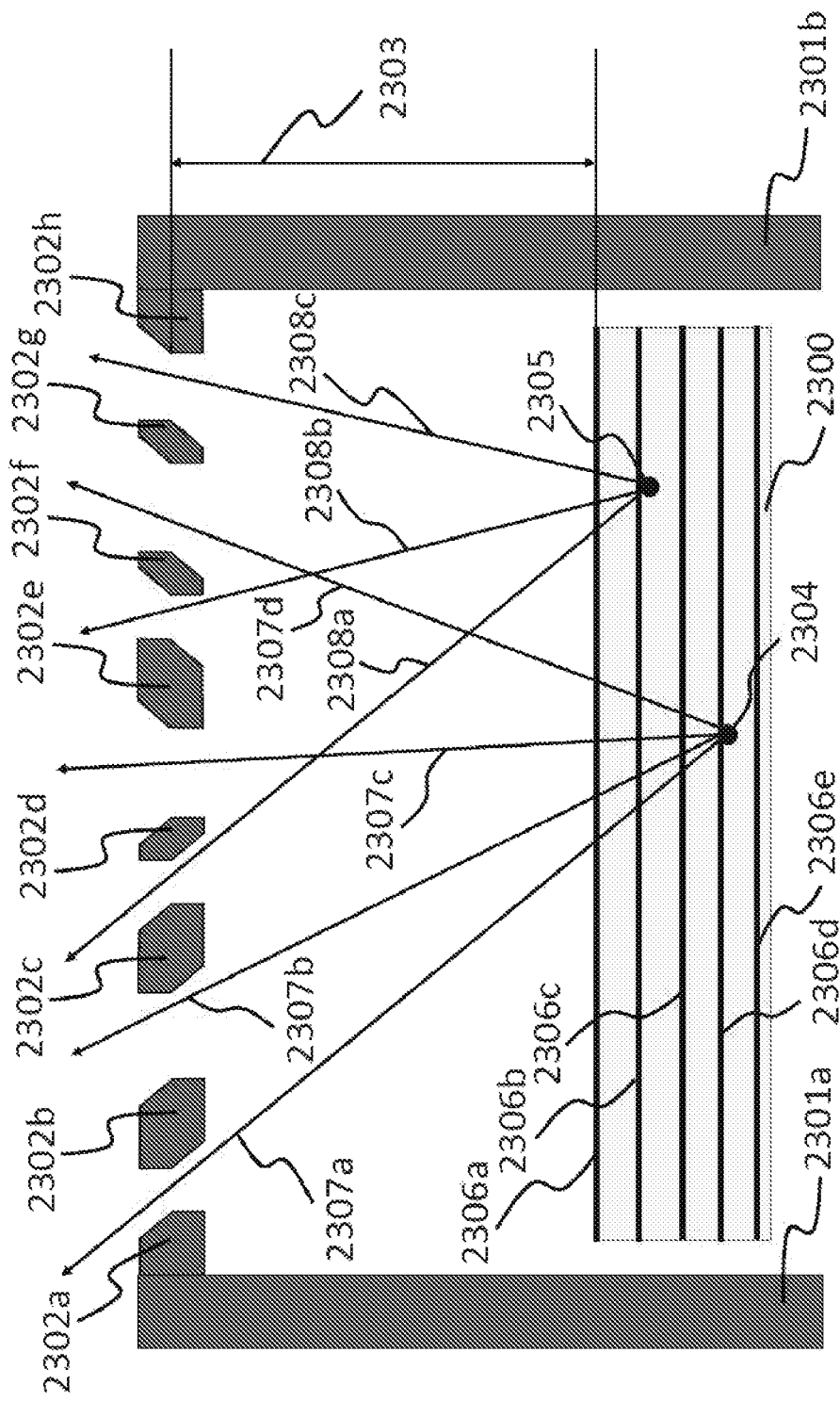
FIG. 23 shows a sectional side view of the large field of view coded aperture imaging system showing how detected events get back-projected into the image space for image reconstruction using multiple reference planes.

When a binned image reconstruction of the radioactive source distribution is desired, some embodiments may involve the use of multiple instrument response planes of reference. FIG. 23 shows an example when multiple planes of reference are used. The position sensitive sensor (2300) is shielded on some sides not covered by the coded aperture by shields (2301a) and (2301b). The coded aperture mask within a first plane comprises elements (2302a)-(2302h). The first plane of the mask is placed at a (2303) distance away from the face of the position sensitive sensor (2300). A first radiation interaction (2304) and a second radiation interaction (2305) are detected with position resolution in all three dimensions by the sensor (2300). In this embodiment, five instrument response planes of reference (2306a)-(2306e) may be employed in the analysis. In this embodiment, the planes of reference sample the sensitive volume of the sensor. Backprojection directions towards the coded mask field of view are represented by (2307a)-(2307d) for interaction (2304) and directions (2308a)-(2308c) for interaction (2305). In this case, the attenuation coefficients along directions (2307a)-(2307d) and (2308a)-(2308c) are extracted from attenuation data calculated at the reference planes and locations closest to the interaction points. As such, attenuation coefficients from the interaction (2304) along directions (2307a)-(2307d) can be extracted from attenuation data calculated in reference plane (2306d) at the location or bin closest to location (2304), and attenuation coefficients from the interaction (2305) along directions (2308a)-(2308c) can be extracted from attenuation data calculated in reference plane (2306b) at the location or bin closest to location (2305). These extracted attenuation coefficients can then be used to build the pdf for the incremented bins. This sampling and pdf calculation scheme can also be used for list-mode imaging.

When a binned image reconstruction is implemented, the binned total count at the bin in plane (2304d) closest to (2304) can be incremented as a result of an interaction detected at (2304), and the binned total count at the bin in plane (2304b) closest to (2305) can be incremented as a result of an interaction detected at (2305). The pdf can then be calculated along directions (2307a)-(2307d) and (2308a)-(2308c), respectively, for the resulting binned intensities.

Whether in list mode or binned mode, the resulting pdf can be used in any suitable iterative or analytic image reconstruction algorithm known in the field. As such the calculated pdf for counts at bins in reference planes closest to interaction locations (2304) and (2305) can be employed in the reconstruction of the gamma-ray source image by employing methods commonly used for image reconstruction, such as statistical iterative methods, algebraic iterative methods, analytical methods or compressive sensing methods.

Figure 24:
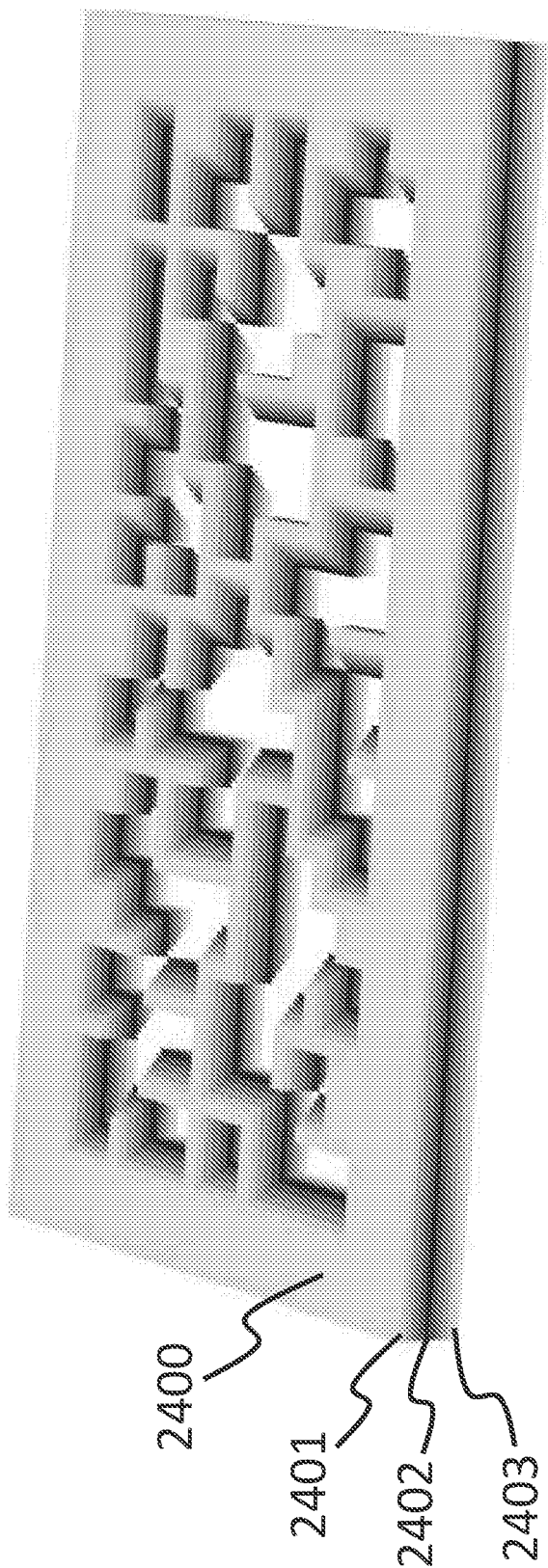
FIG. 24 shows a perspective view of the large field of view coded aperture mask showing one of its compositions, in this case being made of multiple layers stacked together.

FIG. 24 shows a perspective view of a large field of view coded aperture mask (2400) manufactured out of multiple thin mask layers stacked and fixed together. Light gray layers (2401) represent the top layers, darker gray layers (2402) represent the middle layers, and light gray layers (2403) represent the bottom layers. In this embodiment, the mask pixel elements are self-supporting. In embodiments in which mask elements are not self-supporting, frames of low radiation attenuation characteristics can be used to keep the mask elements in the desired location. This manufacturing modality can create mask elements with side faces that have a stair-like appearance, but may substantially follow the bifrustum shaping of the mask elements, as described above.

In some embodiments the individual layers in the coded aperture mask are not fixed to each other, and may be moved by actuators laterally with respect to each other to create various imaging field of views and coding profiles. The actuators may be controlled by a computer. Actuators may also move the individual layers away from each other to increase the collimation effect. Likewise, in some embodiments, each layer may be formed by multiple plates with patterned holes that may move with respect to each other.

Figure 25:
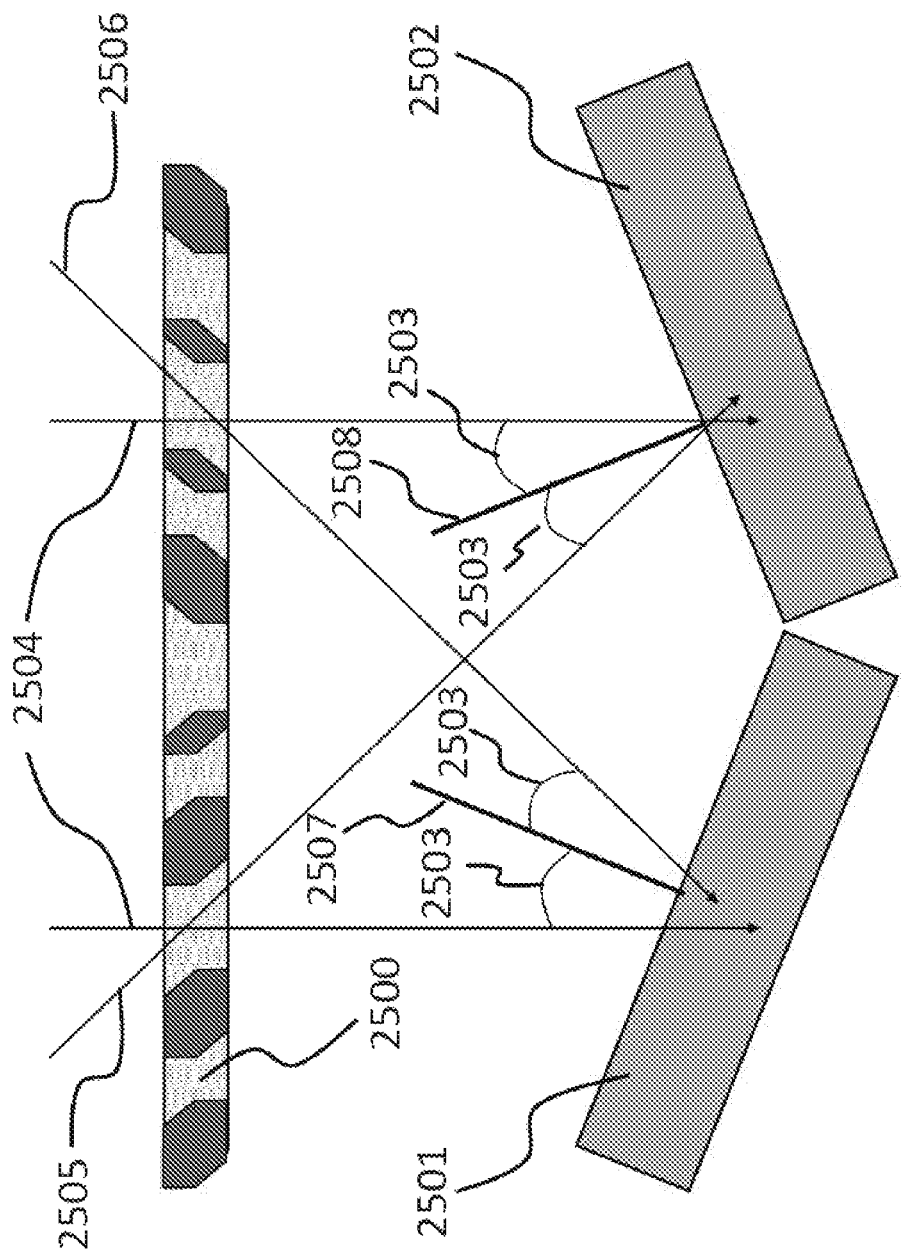
FIG. 25 shows a sectional side view of the large field of view coded aperture imaging system that employs sensors arranged in different planes in order to minimize the range of gamma-ray photon incident angles falling onto the sensors.

In some embodiments in which the gamma sensors may not be equipped to deliver the position of the gamma-ray interactions with resolution in depth, the sensors may be positioned at different angles with respect to each other and with respect to a large field of view mask in order to minimize the range of off-normal angles of the detected photon incident directions. This minimization will reduce the imaging errors associated with unknown depth interactions. FIG. 25 shows a sectional side view of a large field of view coded aperture mask (2500) placed in front of two sensors (2501) and (2502). These sensors are arranged in different planes with respect to each other and with respect to the mask (2500), in order to minimize the range of angles (2503) made by the incident gamma-ray photon directions (2504), (2505), (2506) with respect to the normal of the sensors (2507) and (2508). In this implementation, the sensors have their normal directions (2507) and (2508) converge towards a space essentially adjacent to the middle of the mask (2500). Other embodiments can be envisioned of sensors oriented in different planes with respect to each other and with respect to a mask to minimize the range of angles made by the incident gamma-ray photon directions with respect to the normal of the sensors for most sensors across a sensor group. The mask can be a large field of view mask, as described above, or an adjustable field of view mask, as described below, a focalized, collimated mask, or a combination thereof. The angles made by the normal of the sensors may range from 0° to 90°. In some configurations, the angle between 2 sensor normal directions is between 30° to 60°. In some configurations, the angle between 2 sensor normal directions is between 40° to 50°.

In some embodiments, the mask itself can be made of mask segments that are situated in multiple planes that are essentially non-coplanar.

Figure 26:
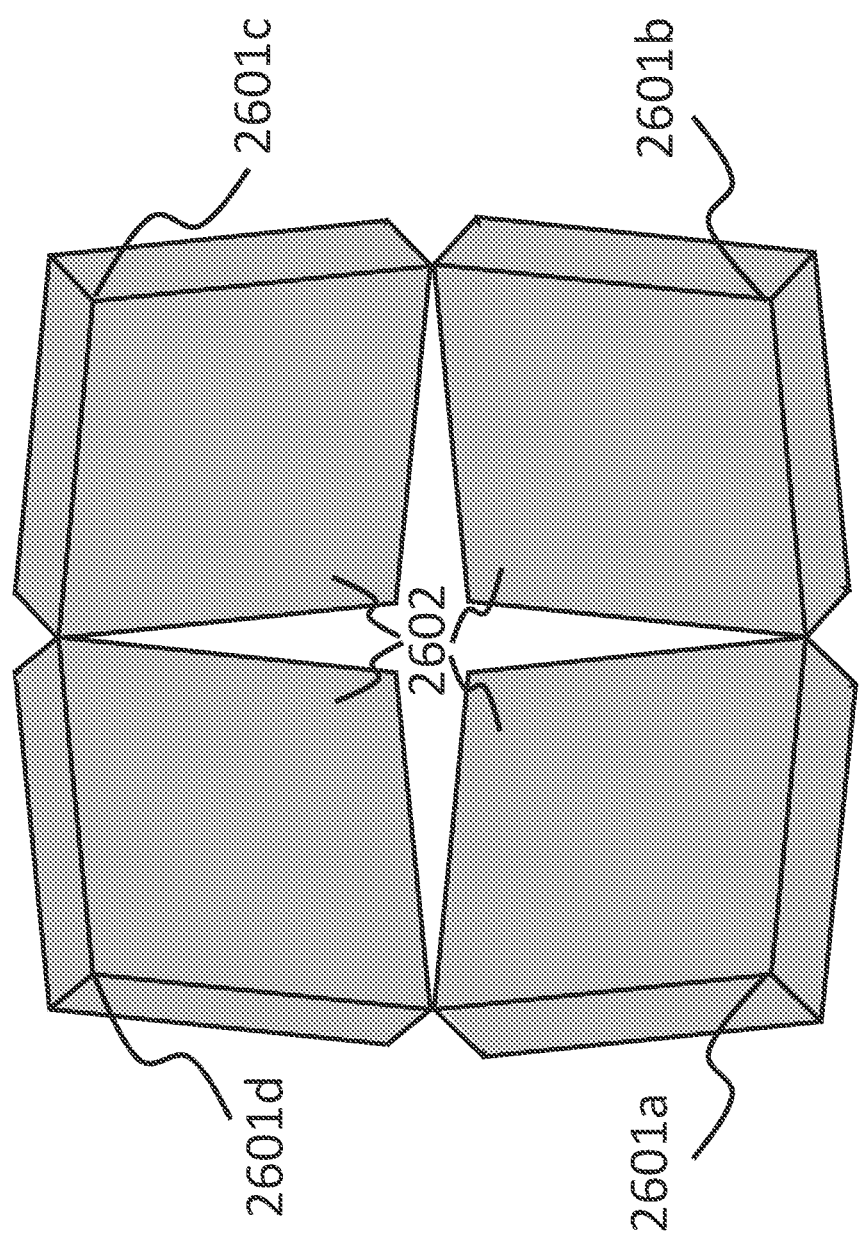
FIG. 26 shows a top view of an arrangement of 4 sensor panels positioned in different planes in order to minimize the range of gamma-ray photon incident angles falling onto the sensors.

FIG. 26 shows a top view, from the mask (not shown), of an arrangement of 4 sensors or sensor panels positioned in different planes, with their normal directions essentially converging towards a volumetric area adjacent to the mask. This arrangement minimizes the range of angles made by the incident gamma-ray photon directions with respect to the normal of the sensors. In this depiction, the sensor corners (2601a-d) are closer to the mask, the sensor corners (2602) are further away from the mask.

In some applications, the gamma ray sensor panels described above may need to both scan the patient to create a 3D molecular image map, and to provide real-time images of reduced volumes inside a patient. These two imaging modes may require a gamma-ray imaging architecture that deliver a wide field of view in scanning mode, and a collimated, narrow focus field of view in a real-time imaging mode. Likewise, there may be advantages to being able to scan a part of a patient with both a wide field of view and a narrower field of view to create a more accurate 3D map. A coded aperture mask with an adjustable field of view can accommodate these requirements.

Figure 27:
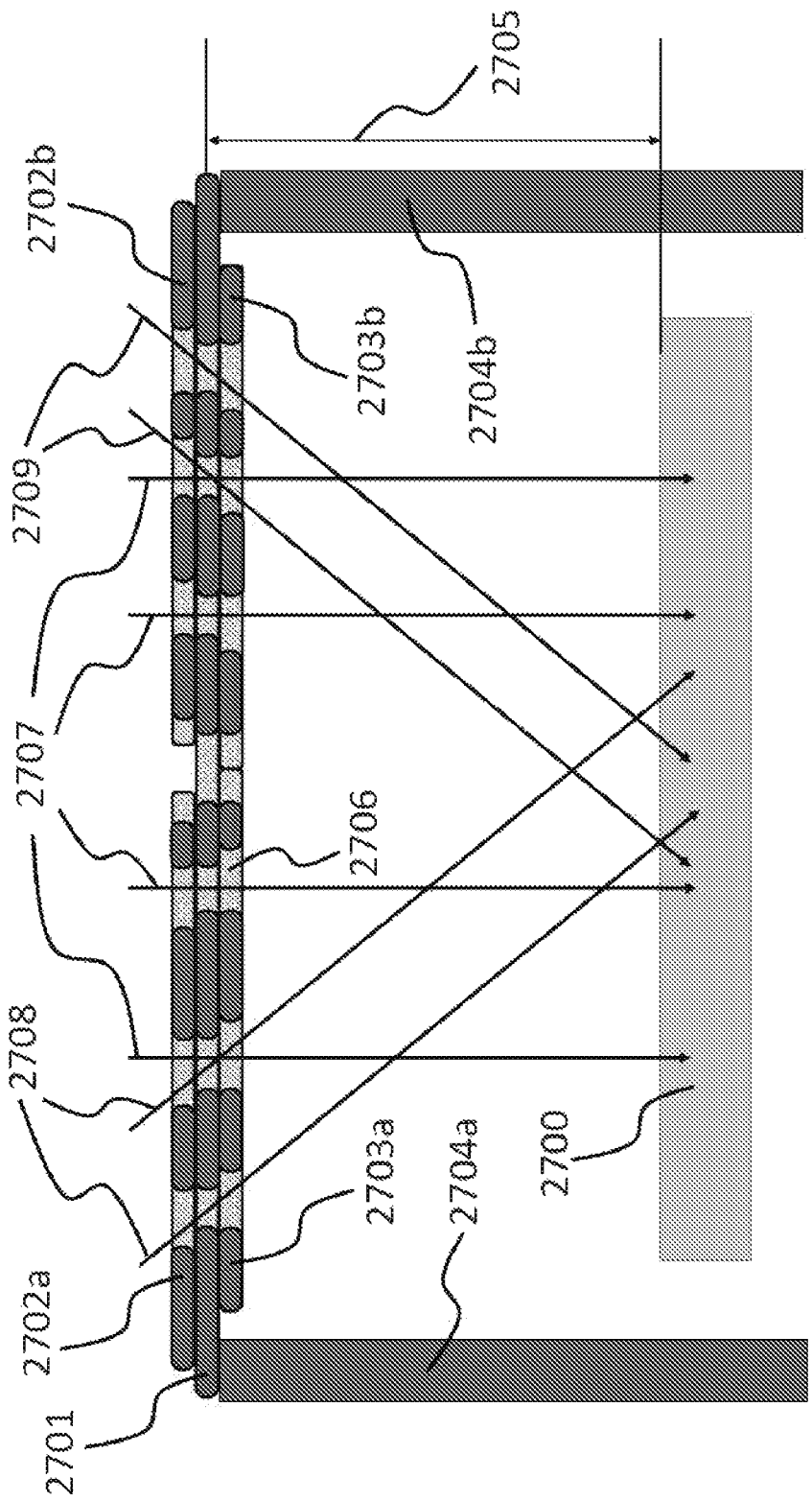
FIG. 27 shows a sectional side view of a coded aperture imaging system with an adjustable 3 layer mask, here in a wide field of view configuration.
Figure 31:
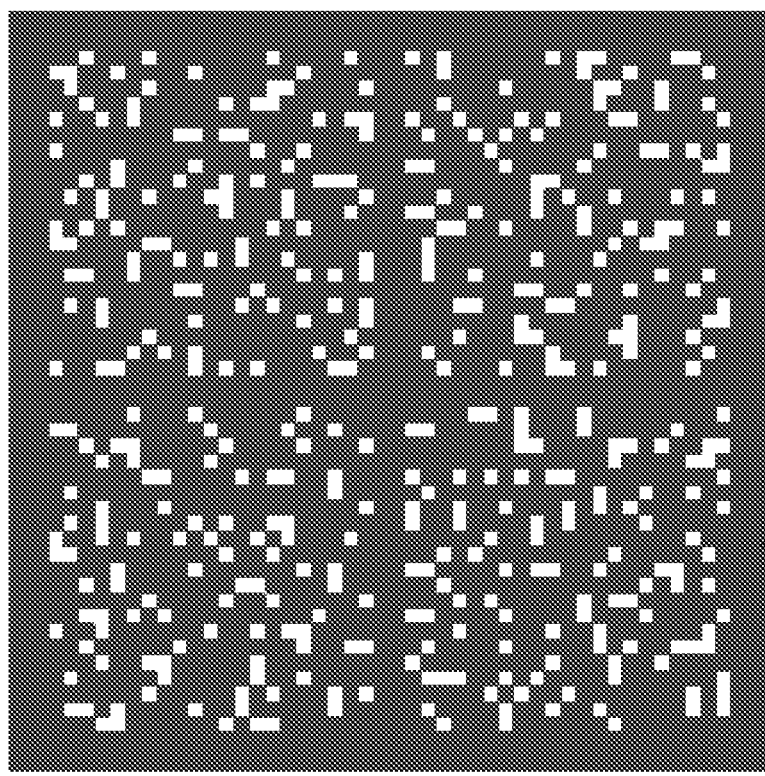
FIG. 31 shows a top view depiction of the middle layer in an adjustable mask having a 22% open fraction pseudorandom pattern.
Figure 32:
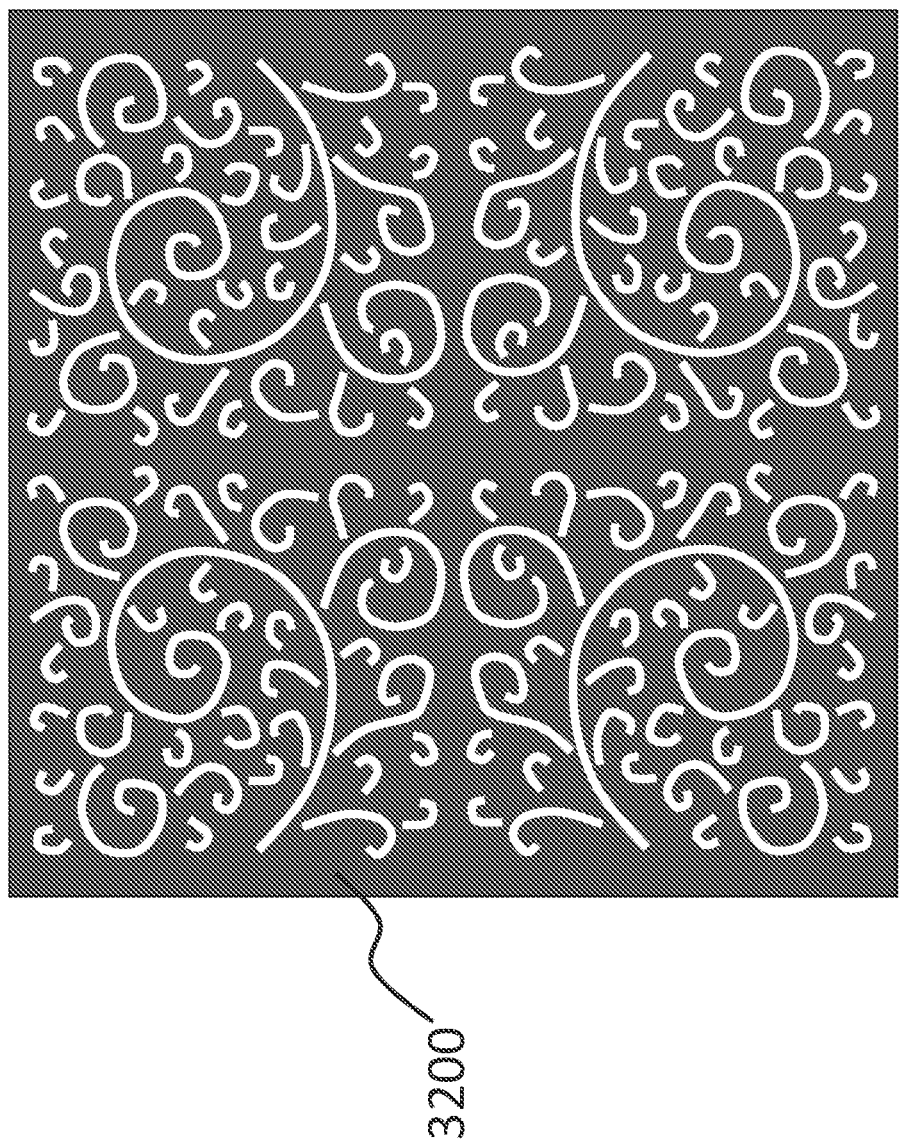
FIG. 32 shows a top view depiction of a coded aperture mask comprising curved slits of various curvatures.

FIG. 27 shows a sectional side view of a coded aperture imaging system comprising a gamma-ray mask with an adjustable field of view. An imaging gamma-ray sensor array (2700) is placed behind a mask assembly that comprises multiple overlapping layers made out of a high density, high atomic number material, such as a tungsten alloy. In this example, the mask comprises 3 layers. The middle layer of the mask (2701) is made of a plate with holes, or openings, penetrating from one side of the plate to the other to create a patterned plate. Example of patterns made by the openings are shown in FIGS. 31 and 32. The pattern can be a pseudorandom array, as shown in FIG. 31, an index class aperture array, an assembly comprising curved slits of various curvatures, as shown in FIG. 32, or another pattern with essentially flat side lobes in the autocorrelation function across multiple magnifications. It is important to maintain essentially flat side lobes across multiple magnifications because the imager will be exposed to sources from very near field distances to intermediate distances, creating projections through the mask of multiple magnifications onto the detector array. In this illustration, the top layer is made of two patterned plates (2702a) and (2702b). The pattern on patterned plates (2702a) and (2702b) may essentially spatially match the pattern of the middle layer (2701), although in some implementations there may be differences between the patterns being overlapped. In this illustration, the bottom layer is made of two patterned plates (2703a) and (2703b). The pattern on patterned plates (2703a) and (2703b) may essentially spatially match the pattern of the middle layer (2701), although in some implementations there may be differences between the patterns being overlapped. The set of overlapping mask layers may be mounted onto side collimators (2704a) and (2704b). These side collimators may also be made of gamma-ray attenuating materials, such as tungsten alloys. The mask may be placed at a focal distance (2705) that may be changeable by an actuator controlled by an operationally coupled computer. The openings in the mask layers in the sectional plane are represented by grey areas (2706). The mask layers can be made of bifrustum elements, as described above. Also as described above, these bifrustum elements can have straight edges or round edges, and their particular shapes can be different from one layer to another layer and from one part of a layer to another part of the same layer, or from one element to another. In some implementations, the pattern can be as described in FIG. 32. This arrangement of layers close to each other allows for far field of view imaging that permits projections normal on the mask (2707), as well as projections at close to +45° (2708), and projections at −45° (2709).

Figure 28:
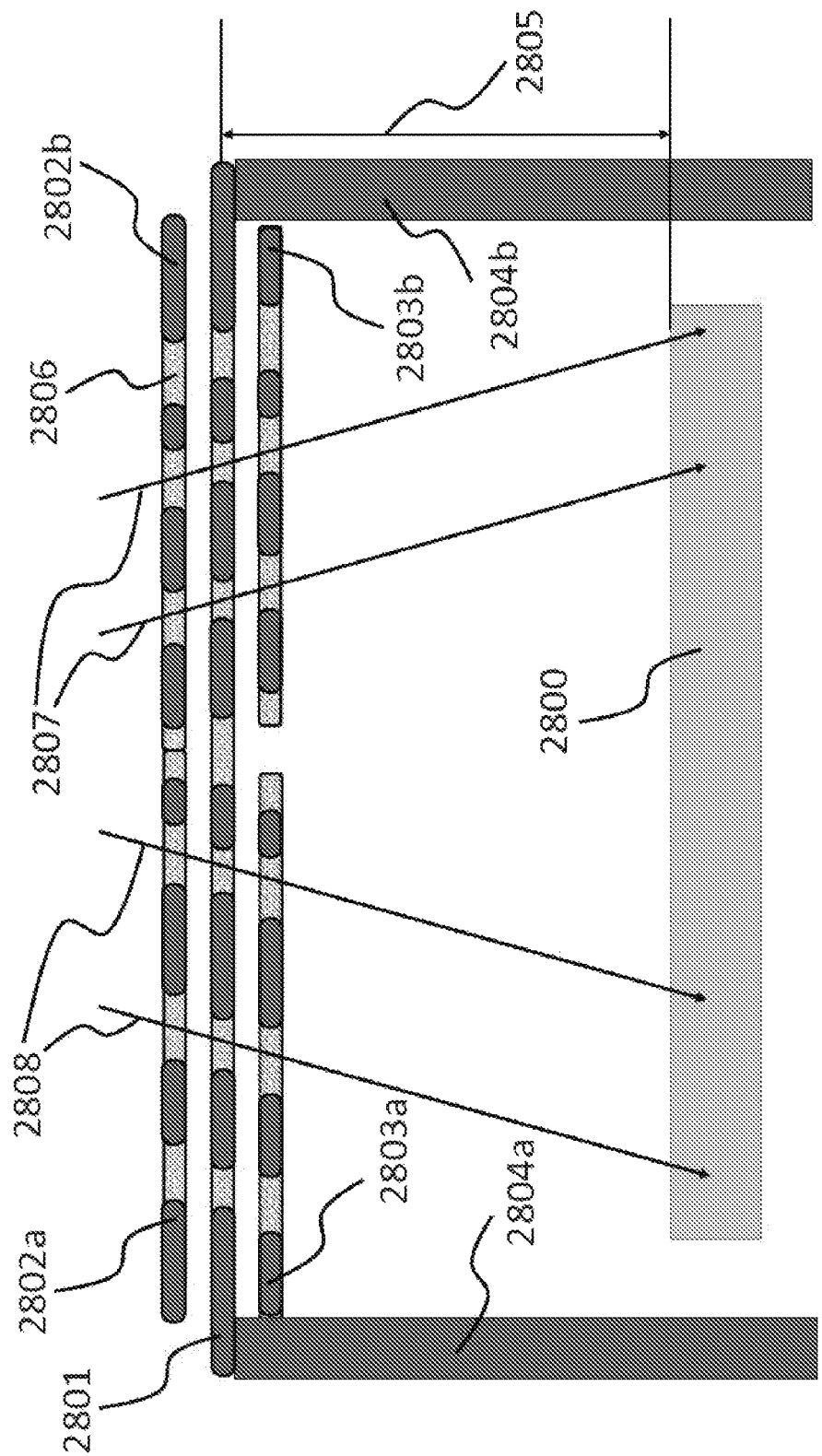
FIG. 28 shows a sectional side view of a coded aperture imaging system with an adjustable 3 layer mask, here in a collimated (foveal) field of view configuration.

FIG. 28 shows a sectional side view of a coded aperture imaging system with an adjustable 3 layer mask, here in a collimated (foveal) field of view configuration. An imaging gamma-ray sensor array (2800) is placed behind a mask assembly described in FIG. 27. In this implementation, the middle layer of the mask (2801), or (2701) in FIG. 7 is at the same relative location with respect to the sensor as in FIG. 7. However, the top layer made out of patterned plates (2802a) and (2802b) have been moved away from the middle layer by an actuator coupled operationally to a computer. In some implementations, the plates (2802a) and (2802b) may also be shifted laterally with respect to the middle layer by actuators coupled operationally to a controlling computer. In this case, the two plates are laterally moved towards the center of the mask. The bottom layer made out of patterned plates (2803a) and (2803b) have also been moved away from the middle layer by an actuator coupled operationally to a computer. In some implementations, the plates (2803a) and (2803b) may also be shifted laterally with respect to the middle layer by actuators coupled operationally to a controlling computer. In this case, the two plates are laterally moved towards the edge of the mask. The mask's focal distance is represented by (2805). The net effect of these translations is a reduction of the field of view towards the median of the mask, as the separation of the layers create a collimating effect. The primary projection directions remaining through the openings represented by grey areas (2806) are represented by directions (2807) and (2808).

Figure 29:
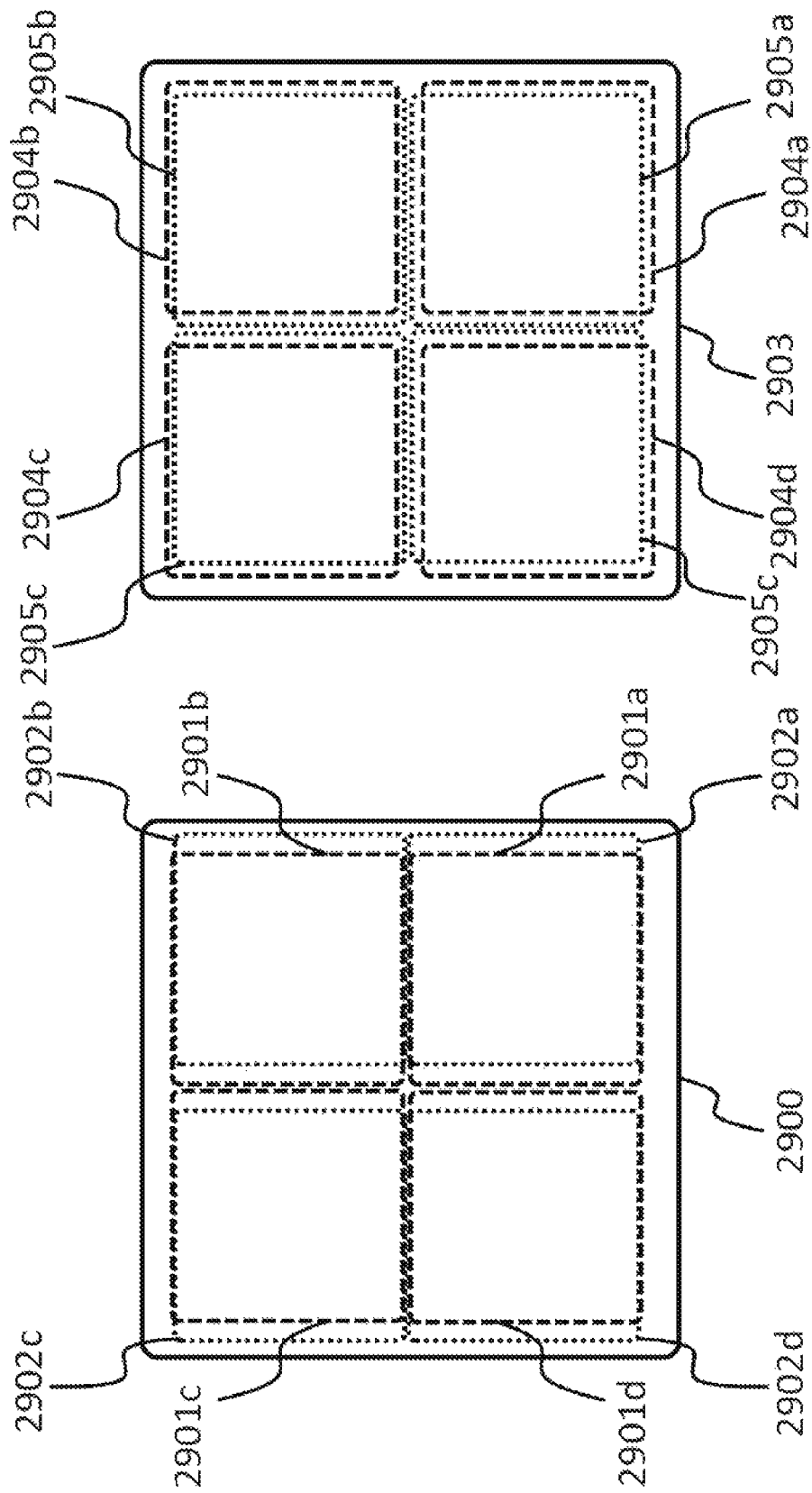
FIGS. 29A and 29B show schematic top views of coded aperture masks made of 9 panels arranged in 3 layers in two configurations: a wide and a collimated field of view.

FIGS. 29A and 29B show schematic top views of an adjustable coded aperture mask made of 9 panels arranged in 3 layers—4 on top, 1 in the middle, and 4 on the bottom, in two configurations. The mask of FIG. 29A is configured in a wide field of view and the mask of FIG. 2B is configured in a narrow, collimated field of view. For clarity, the elements and movements are not depicted to scale. The purpose of this figure is to represent an example of a lateral movement of the plates as they transition from wide field of view to narrow field of view. The contour of the middle layer is represented by the continuous line (2900) in the wide field of view configuration. The contour of the four plates forming the bottom layers (towards the detector) are represented by dashed line squares (2901a-d). The contour of the four plates forming the top layers (away from the detector) are represented by dotted line squares (2902a-d). This configuration has the layers close to each other, and may create a large field of view opening, particularly in left-right direction.

The contour of the middle layer in the narrow field of view configuration is represented by the continuous line (2903). The contour of the four plates forming the bottom layers (towards the detector) are represented by dashed line squares (2904a-d). The contour of the four plates forming the top layers (away from the detector) are represented by dotted line squares (2905a-d). This configuration has the layers away from each other, and may create a narrow, collimated field of view opening towards the median of the mask. Other lateral movements can take place. For example, to create a collimation away from the mask median in any direction of interest, the plates within the same layers could move laterally jointly in the same direction. For example, to shift the collimation of the mask towards the right of the figure, the top plates (2905a-d) would move right from the configuration of FIG. 29B, and bottom plates (2904a-d) would move left from the configuration of FIG. 29B. Depending on the exact alignment of the patterns between layers, other plate movements may achieve similar effects. Likewise, depending on the exact alignment of the patterns between layers, the same plate movements may achieve very different collimation and field of view changes. For example, in some implementations, when the patterns across layers have certain alignments, a lateral movement of the plates across different layers may reduce or increase the effective opening fraction of the mask.

Figure 30:
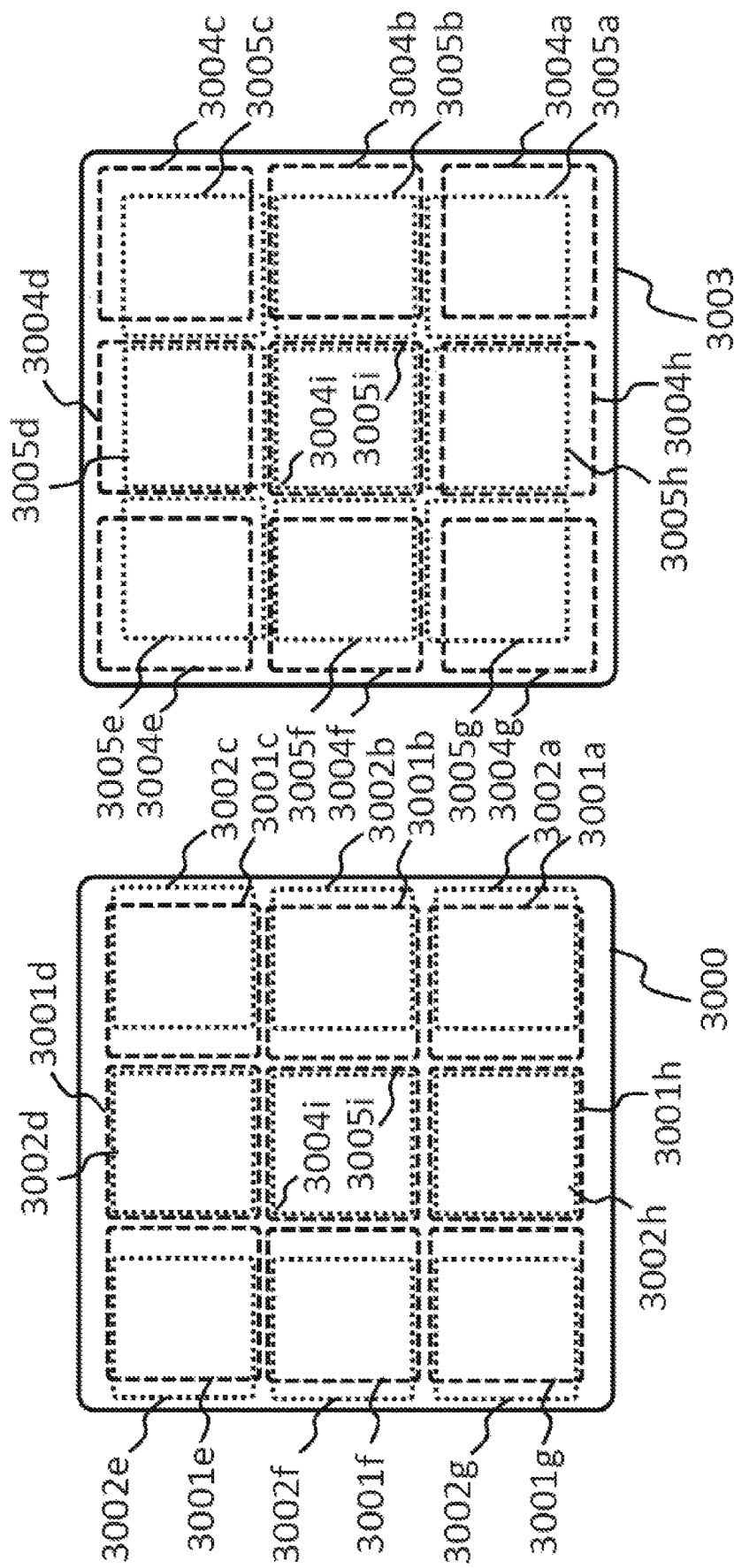
FIGS. 30A and 30B show schematic top views of coded aperture masks made of 19 panels arranged in 3 layers in two configurations: a wide and a collimated field of view.

FIGS. 30A and 30B show schematic top views of an adjustable coded aperture mask made of 19 panels arranged in 3 layers, 9 on top, 1 in the middle, 9 on the bottom, in two configurations: 30A, in a wide field of view and 30B in a narrow, collimated field of view. For clarity, the elements and movements are not depicted to scale. The purpose of this figure is to represent an example of a lateral movement of an array of 3×3 plates as they transition from wide field of view to narrow field of view. The contour of the middle layer is represented by the continuous line (3000) in the wide field of view configuration. The contour of the 9 plates forming the bottom layers (towards the detector) are represented by dashed line squares (3001a-i). The contour of the 9 plates forming the top layers (away from the detector) are represented by dotted line squares (3002a-i). This configuration has the layers close to each other, and may create a large field of view opening, particularly in left-right direction. The contour of the middle layer in the narrow field of view configuration is represented by the continuous line (3003). The contour of the 9 plates forming the bottom layers (towards the detector) are represented by dashed line squares (3004a-i). The contour of the 9 plates forming the top layers (away from the detector) are represented by dotted line squares (3005a-i). This configuration has the layers away from each other, and may create a narrow, collimated field of view opening towards the median of the mask. As described in FIGS. 29A-B, other lateral movements and effects can take place.

FIG. 31 shows a top view depiction of a layer in an adjustable multilayer mask having a 22% open fraction pseudorandom pattern. The pixel elements can be bifrustums, as described above, with straight or rounded edges. The pattern may be optimized to provide essentially flat side lobes in the autocorrelation function across multiple magnifications, such as for any combination of magnifications from 1× to 6×. The opening fraction for this mask may be from 0.1% to 70%. In a preferred embodiment, the opening fraction is from 5% to 30%.

FIG. 32 shows a top view depiction of a coded aperture mask comprising curved slits of various curvatures. The combination and arrangements of slits can be optimized to provide essentially flat side lobes in the autocorrelation function across multiple magnifications, such as for any combination of magnifications from 1× to 6×. The opening fraction for this mask may be from 0.1% to 70%. In a preferred embodiment, the opening fraction is from 5% to 30%. The slits may have straight edges, rounded edges, similar to rounded bifrustums described above, or edges of various other profiles, such as v-shaped profiles. The shape of the edges may change from one slit to another or within the same slit. The rounded slits may or may not intersect. The curvature of the slit may change within the same slit and across slits. Such slit geometries of varying curvatures may help achieving flat side lobes in the autocorrelation functions across multiple magnifications.

Figure 33:
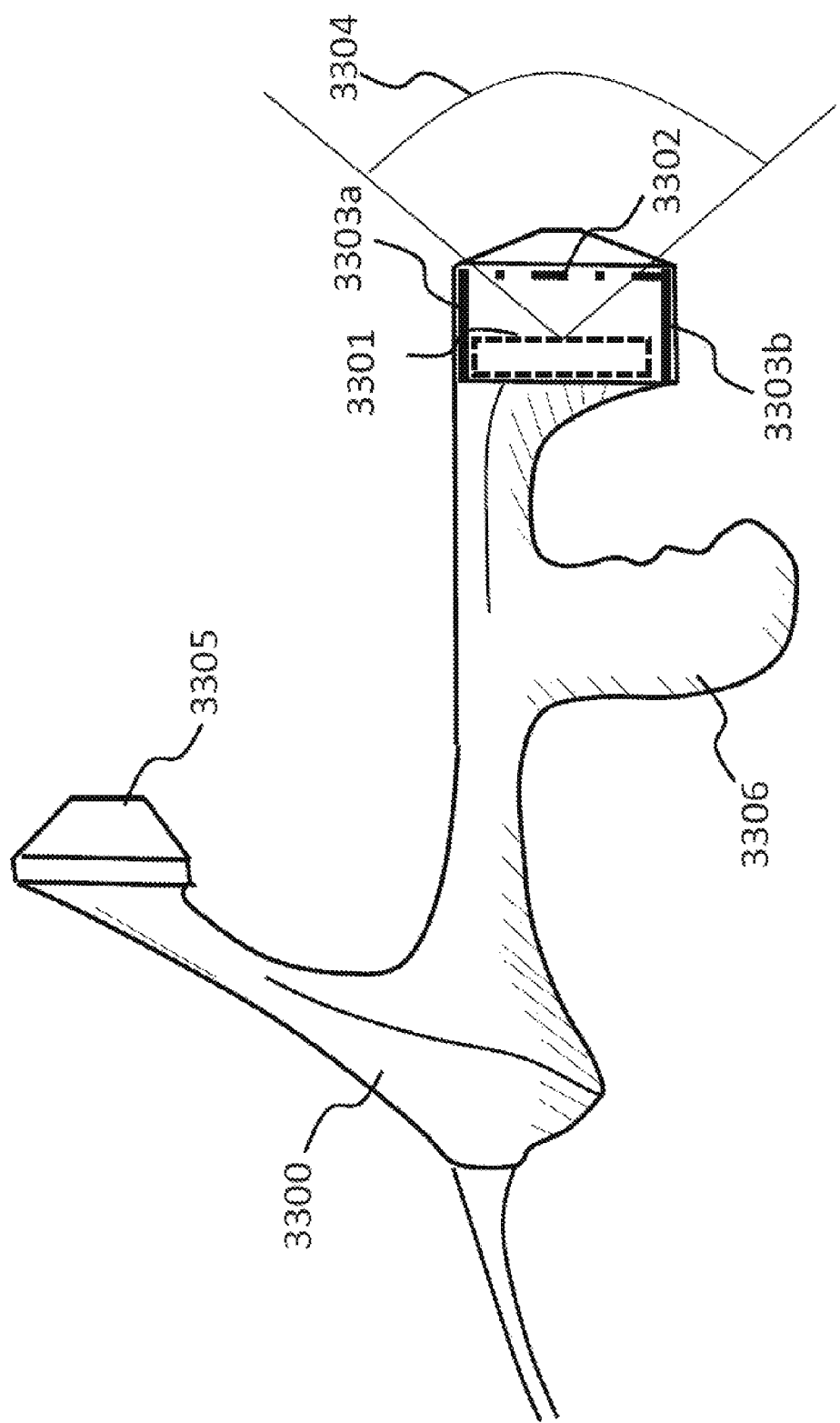
FIG. 33 shows an embodiment of a handheld SPECT camera showing the location of the large field of view coded aperture mask and sensor.

FIG. 33 shows a drawing of a handheld SPECT camera device (3300). The handheld instrument (3300) contains a position sensitive sensor (3301) placed behind a large field of view coded aperture mask (3302), and between shields (3303a) and (3303b) placed at locations not covered by the mask (3302). This imaging system is characterized by a large imaging field of view (3304). This particular instrument also comprises a video camera or scanner (3305) that is oriented to collect contextual information that can be used to create a 3D model of the patient and to locate the handheld camera system with respect to the patient. A handle (3306) can be used to easily move the device.

Figure 34:
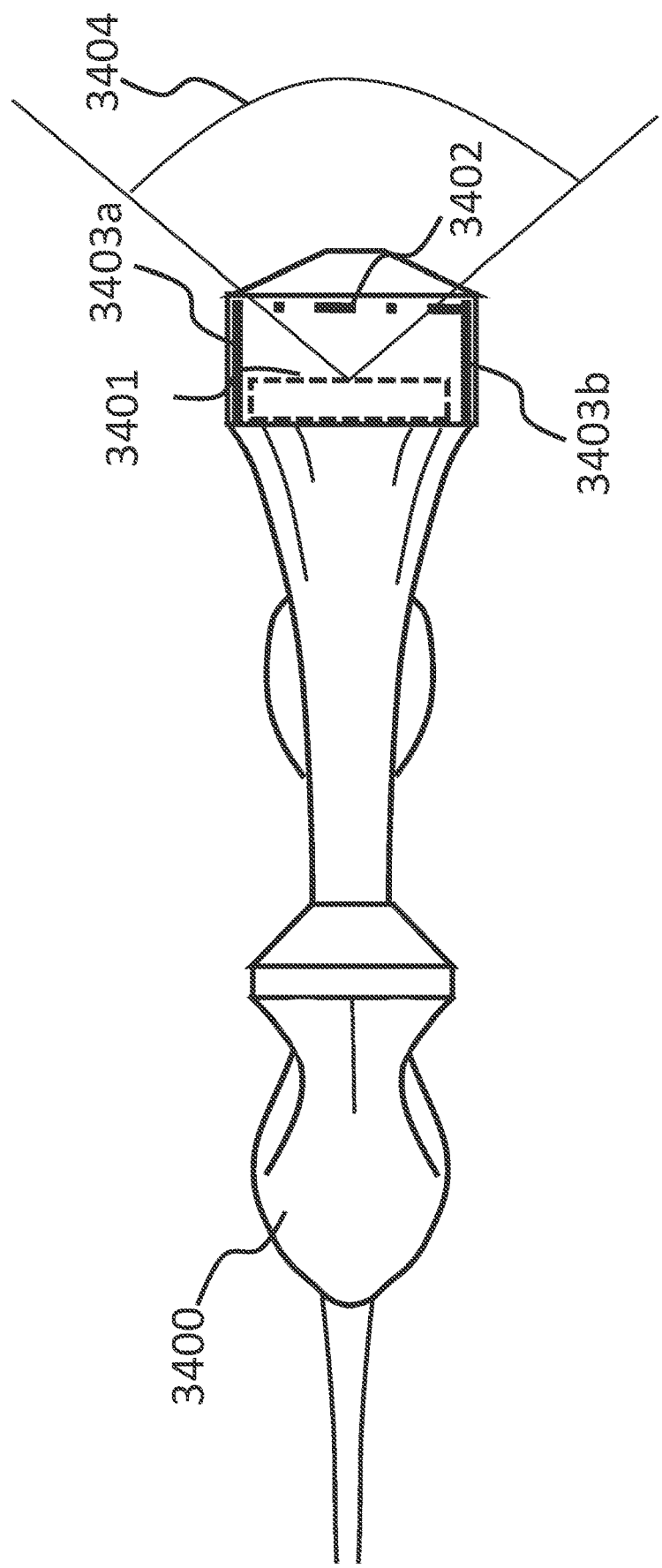
FIG. 34 shows a top view of an embodiment of a handheld SPECT camera showing the location of the large field of view coded aperture mask and sensor.

FIG. 34 shows a top view drawing of the handheld instrument (3400) presented in FIG. 33. The handheld instrument (3400) is shown containing a position sensitive sensor (3401) placed behind a large field of view coded aperture mask (3402), and between shields (3403a) and (3403b) placed at locations not covered by the mask (3402). This imaging system is characterized by a large imaging field of view (3404).

Figure 35:
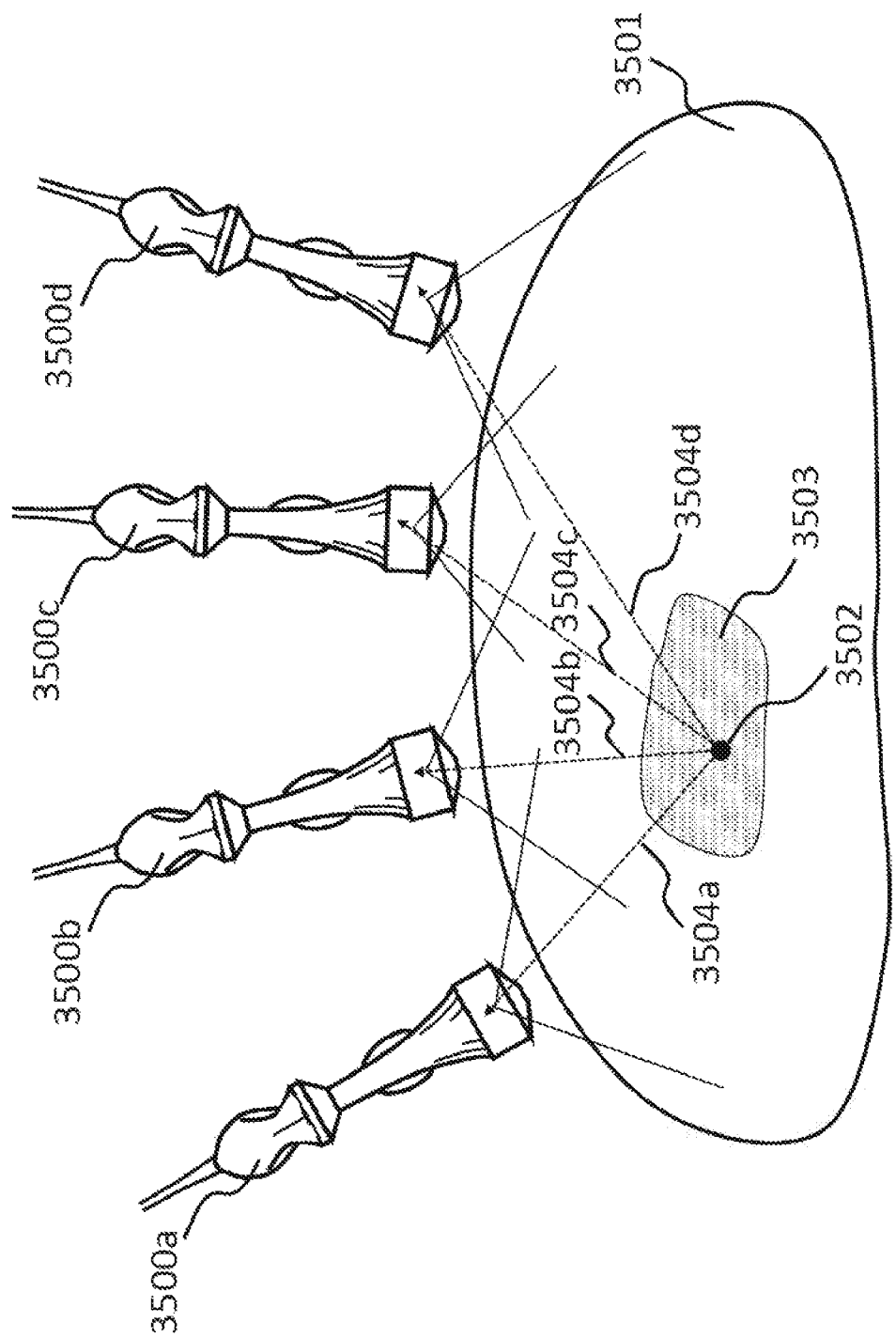
FIG. 35 shows a drawing of an embodiment of a handheld SPECT camera with a large field of view coded aperture scanning the body of a patient from a reduced range of angles around the patient, providing at the same time sufficient angular sampling of the image space.

Using the handheld SPECT camera device described in FIG. 33 and FIG. 34, a high resolution SPECT image can be reconstructed by taking advantage of the high resolution, high field of view and high sensitivity characteristics to the various imaging embodiments presented here. FIG. 35 shows a depiction of the modality by which such an instrument can perform SPECT imaging from a limited number of directions around the patient, but still preserving a significant range of projections for each voxel in the field of view. The handheld imaging device is moved at different locations (3500a)-(3500d) on one side of the patient (3501). The figure shows how a voxel (3502) inside molecularly tagged organ (3503) inside the body can be imaged by the device at all locations (3500a)-(3500d) thanks to the imaging system's large field of view. Examples of projection lines (3504a)-(3504d) towards the SPECT camera at locations (3500a)-(3500d) show a range of angles (such as between directions (3504a) and (3504d)) that can be even larger than 90 degrees, which is sufficient parallax to reconstruct the image with high resolution in all 3 coordinates.

In some embodiments, the SPECT camera may be moved around and along the patient by a robotic arm or by other mechanical system.

Thus, the embodiments of the imaging modality described here allow for a simpler, lightweight, and economical SPECT imaging device with improved imaging performance.

Figure 36:
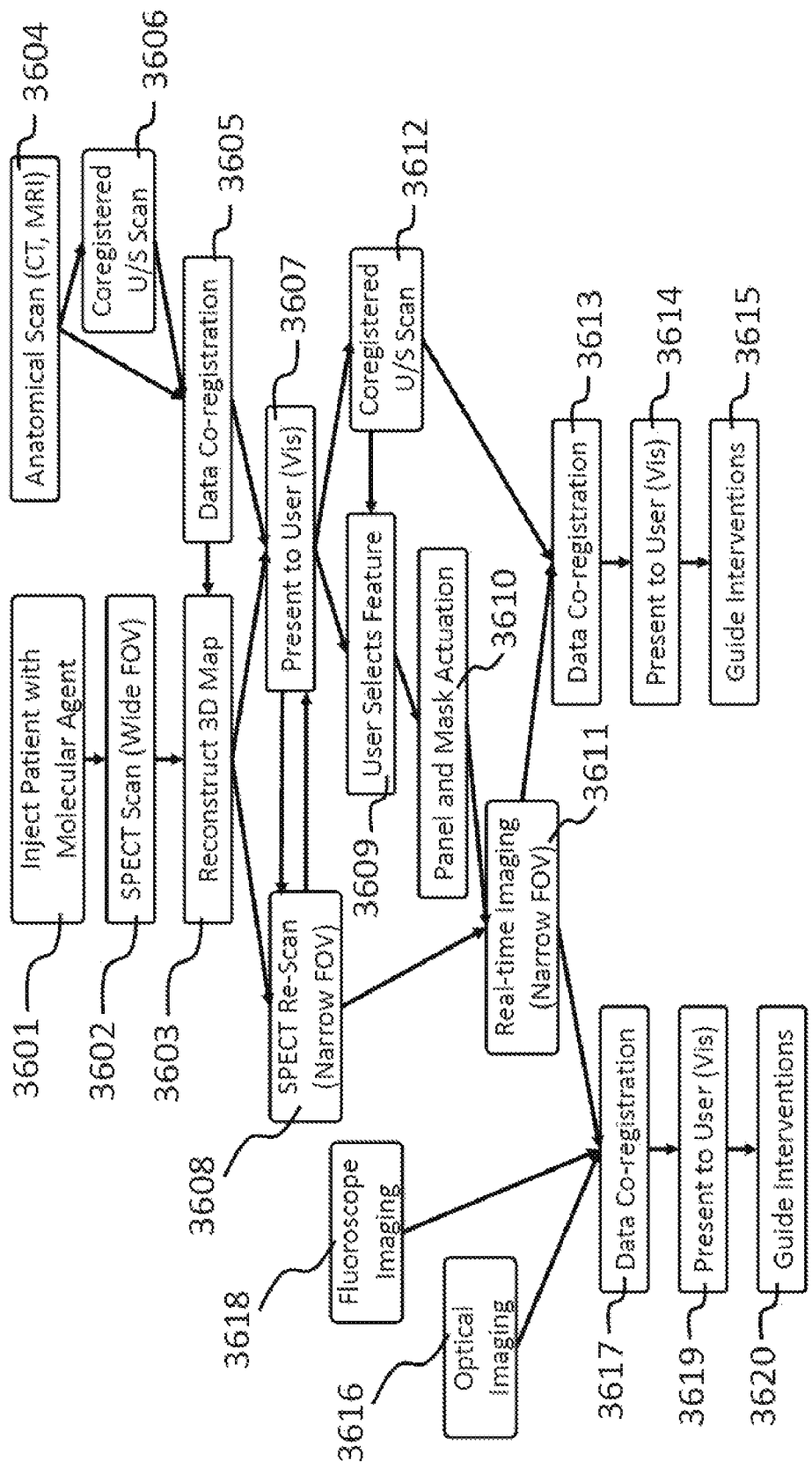
FIG. 36 shows a flow chart that summarizes some systems and methods enabled by a portable molecular imaging system.

FIG. 36 shows a flow chart that summarizes some systems and methods enabled by a portable molecular imaging system. In this case we exemplify the processes assuming a portable SPECT imaging system. The first step in the process (3601) is to inject a patient with molecular agent, in this example, a SPECT molecular agent. In a second step (3602), the SPECT system described herein is used to scan a part of the patient to provide the data used by an operationally couple computer to build a 3D map of the molecular agent in step (3603). The scanning objective will be selected by a user from a group of scanning objectives stored in the memory of the computer. The computer vision system described in FIG. 1 and FIG. 13 among others may deliver data to the computer to create a 3D model of the patient's body, as described above. The computer may use the 3D model of the patient to create a scanning protocol given the scanning objective. The scanning protocol will comprise a set of actuations the robotic arm and the sensor panels will take to scan the patient. The set of actuations may also comprise instructions to the actuators moving the gamma-ray mask elements and the focal distance of the mask. The set of actuations may also comprise instructions to the actuators moving the portable cart shown in FIGS. 1 and 13.

The SPECT system may use the adjustable mask in the wide field of view configuration (see FIG. 27). However, for some applications, the mask-detector assembly may be in other, narrower field of view configurations, or it may change at different points during the scan. The computer or a user may control those changes during the scan. Likewise, for some applications, during the scan (3602), the focal distance between the mask and the detector may change at various point during the scan. The computer or a user may control those changes during the scan.

To support the image reconstruction process, imaging scans can be performed with other instruments (3604) to create imaging datasets, such as anatomical imaging datasets, that can be used by a computer operationally coupled to the SPECT scanner. For example, a CT dataset can be used to provide an attenuation map to be used by the computer to create more accurate reconstructions of the molecular image.

A co-registration system (3605) and method, as the one described in FIG. 13, can be used to merge the SPECT data with the other imaging data. For improved co-registration, especially when the 3D models of the body of the patient and the 3D model extracted from the external image dataset deviates significantly, a co-registered ultrasound scan can be performed (3606) to allow the computer to pin specific structures in the other imaging modality to specific locations, as described in FIG. 13. That other imaging dataset can be rendered and sent to a display for examination by a user (3607). Likewise, the computer can send a rendering of the reconstructed 3D molecular map to the visualization device for inspection by a user. The visualization device can be a screen, a head mounted display, a augmented reality device, or another visualization system. The computer may send to the visualization device a combination of the other anatomical image and the molecular image. The computer may also save to the memory the molecular image dataset, the ultrasound image dataset used to aid co-registration and the other anatomical image dataset.

Following the 3D image reconstruction (3603), using the reconstructed data, the computer may use instructions stored in the memory to control the molecular imaging system to perform a follow up scan (3608) to improve the quality of the reconstructed 3D map. For a repeat scan, the computer may create another scan protocol comprising a new actuation dataset. For example, the computer may send instructions to the robotic arm and panels to scan the patient, or may send instructions to the mask actuators to change the field of view or to change the focal distance for the follow-up scan. For example, it may be beneficial to re-scan a specific part of the body in the foveal, narrow field of view mode to get better molecular image contrast in specific areas of the body, where features of interest may be present. The scanning protocol may be send to a user for approval. Moreover, the user may initiate a repeat scan given the data presented to the user after the first scan. In some implementations, the user may be remote. The computer may use the data from the molecular imaging scan and/or from the other co-registered anatomical imaging scans, and/or from the co-registered ultrasound scans to perform a neural network, or deep learning, analysis of the data to determine utility for a follow up scan, and to perform a classification of imaging features. The results of the analysis can be presented to the user. Among other things, the results can comprise renderings of the co-registered image datasets, and renderings of processed fused images that may contain classification values. Statistical, deep learning, and sensor fusion algorithms can be used by the computer for this purpose.

Following the visualization step (3607), the user may want to get a real-time image of certain molecular structures. Using a user interface, in step (3609), the user may select such structure of interest identified in a rendering of the co-registered datasets. The selected feature will be characterized by a 3D coordinate.

In step (3610), using instructions stored in a memory, the computer will actuate any of: the robotic arm, the sensor panels, and the mask actuators to orient the sensors towards the selected feature. For example, the mask may be actuated to create a narrow field of view collimated towards the feature of interest to maximize imaging sensitivity and signal to noise in the area where the feature of interest is. In calculating the movement of the panel towards the location from which it can take data from the region of interest, the computer will take into account the 3D model of the patient's body so that no component of the scanner, including the panels, will collide with the patient.

At this point, in step (3611), the data collected from the molecular imaging sensors may be analyzed by the computer to create images in close to real time. As described above, the computer may use previously scanned molecular 3D datasets, such as the datasets resulting from steps (3603) or (3608) in conjunction with the real time molecular data delivered by the molecular sensors under the step (3611) to improve the quality of the real-time molecular image renderings. Likewise, as described above, a co-registered ultrasound scan can be performed under step (3612) to provide anatomical context to the molecular images. The molecular images to be augmented onto an ultrasound image can be delivered by steps (3603) or (3608), or can be real-time images resulting from step (3611).

Moreover, the user may use the visualized ultrasound scan in a user interface to select 3D co-registered features of interest under step (3609). The user may select such structure of interest identified in any rendering of the co-registered imaging datasets. In step (3613) the computer co-registers the ultrasound dataset with the live molecular image using tracking data, such as provided by the computer vision system, as described in FIG. 1 or 13.

In some implementations, the computer may use the real-time ultrasound scans delivered under the step (3612) to create a tissue deformation model used in the construction and rendering of either the stored 3D molecular image dataset (from step (3603) or (3608)), or of the real time molecular image (from step (3611)). Details of the deformation modeling process are presented above.

In step (3614) the computer sends renderings of the ultrasound scan and of the co-registered molecular image scan to the visualization device for user inspection. In some implementations, in step (3615), interventions guided by the molecular imaging system can be performed. For example, interventions can use a rendering of the molecular image to highlight targets of interest. In another example, interventions can use a rendering of the molecular image augmented onto live ultrasound or other real time imaging modality to highlight targets of interest. Such interventions can comprise, biopsies, ablations, excisions, radiation treatments, or other medical procedures. The interventions can be selected from a group containing: interventions done manually by a user using needles, ablation systems, surgical devices or other medical instruments, interventions done by a co-registered high intensity focused ultrasound system to treat an area, interventions done through a co-registered stereotactic system to guide biopsies and surgeries, interventions performed by a robotic medical system to guide excisions and surgeries, interventions performed by a laparoscopic system to guide excisions and surgeries, interventions performed by a co-registered radiation treatment device to treat tumors. For example, the molecular image augmented onto the ultrasound image can guide a user to drive a needle, an ablation system, or another medical device towards a feature of interest. The coregistration with other imaging systems and treatment systems can be done using the on-board computer vision camera, another coregistration and tracking devices. In some implementations in which the user performing an intervention (3615) is robotic or automated, step (3614) may be skipped.

The molecular imaging system can be used in conjunction with imaging modalities other than ultrasound for diagnostic and for intervention guidance. For example, co-registered optical medical systems can be used, such as endoscopes, bronchoscopes, laparoscopes, colonoscopes, microscopes, robotic endoscopes, and robotic laparoscopes. In step (3616), such an optical imaging system is used to image a patient.

In step (3617) the computer co-registers the optical instrument with the molecular imaging system. If the optical medical imaging device is rigid, the onboard computer vision system described in FIGS. 1 and 13 can be used to locate the medical imaging device with respect to the computer vision system, and with the molecular imaging system. Tags and labels can be affixed to those devices to aid location and tracking of the optical medical device.

If the optical system is flexible, or it is not readily in the field of view of the computer vision system, other modalities can be used to create co-registration. For example, if the optical medical device is an endoscopic camera or a flexible laparoscopic camera, in step (3618) a fluoroscope may be used to determine the position and orientation of the endoscope with respect to the fluoroscope reference system by having the computer load the fluoroscope images and analyzing features associated with the endoscope's structures to infer the location of the fluoroscope camera with respect to the fluoroscope's x-ray source and sensors. In some implementations, the optical medical device may already be co-registered with x-ray systems, such as fluoroscopic system. In this case, it's not necessary for the computer to analyze the fluoroscopic image to infer the position of the optical medical device.

A fiducial tag comprising features identifiable in the fluoroscope image can be positioned in the fluoroscope's field of view, such as on the patient, or close the patient. The fiducial tag may also comprise features identifiable by the onboard computer vision system. A computer operationally connected to the computer vision system may use the computer vision data to determine the location of the computer vision camera with respect to the fiducial tag. The computer may read and analyze the fluoroscope images to extract the position of the fiducial tag with respect to the fluoroscope. The computer may then use the co-registration between the optical imaging camera to the fluoroscope, the position of the fluoroscope with respect to the tag, the position of the tag with respect to the computer vision system to determine the position of the laparoscopic or endoscopic medical optical camera with respect to the computer vision camera. This allows the co-registration between the images taken by the optical medical camera and the molecular images. In step (3619) the computer can send renderings of co-registered images taken by the optical medical device and the molecular imaging device to a visualization device. In some implementations, the molecular image will be rendered by the computer in a perspective projection rendering to match the position, orientation and focal length of the medical optical camera at all times. This will create rendering molecular imaging data suitable to augment onto the live image taken by the optical medical device. A rendering such as maximum intensity projection can be used to render the molecular image. Other tracking system could be used to co-register the x-ray system with the molecular imaging system. In step (3620), guided by live optical images delivered by the optical medical device and an augmentation of the molecular image rendering, interventions can take place, such as biopsies, ablation, excisions, surgeries, etc. Step (3619) can be skipped if the medical intervention (3620) is automated or robotic.

While the above description contains many specificities, these should not be construed as limitations on the scope, but rather as an exemplification of one or several embodiments thereof. Many other variations are possible.

In some embodiments, a computer system may be used to implement any of the entities or components described above. The computer system includes a central processor to communicate with each subsystem and to control the execution of instructions from a system memory or a fixed disk, as well as the exchange of information between other subsystems of the computer system. As used herein, a processor includes a single-core processor, multi-core processor on a same integrated chip, or multiple processing units on a single circuit board or networked. The system memory and/or the fixed disk may embody a computer-readable medium. The computer system can also include input/output (I/O) devices. The computer system can include a network interface, which can be used to connect the computer system to a wide area network such as the Internet.

Storage media and computer-readable media for containing code, or portions of code, can include any appropriate media known or used in the art, including storage media and communication media, such as but not limited to volatile and non-volatile, removable and non-removable media implemented in any method or technology for storage and/or transmission of information such as computer-readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, data signals, data transmissions, or any other medium which can be used to store or transmit the desired information and which can be accessed by the computer.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

A recitation of "a," "an" or "the" is intended to mean "one or more" unless specifically indicated to the contrary. The use of "or" is intended to mean an "inclusive or," and not an "exclusive or" unless specifically indicated to the contrary.

Use of terms such as "first," "second," "third," "fourth," etc. may be used to differentiate other one element from another element and do not necessarily imply an ordering or hierarchy among such elements unless otherwise indicated.

What is claimed is:

1. A portable Single Photon Emission Computer Tomography (SPECT) imaging system to scan a patient, the system comprising:
    a Single Photon Emission Computer Tomography controller unit, the controller unit comprising a computer;
    a mechanical jointed arm connected to the controller unit, wherein the jointed arm can be positioned to a desired location by a user through applying direct force;
    at least one gamma camera panel connected to the jointed arm, wherein the gamma camera panel comprises gamma camera sensors with position and energy sensing resolution, wherein the gamma camera panel provides an imaging field of view that is larger than 15 degrees;
    a camera mounted in such a way as to observe an overall area of a patient; and
    at least one processor and a memory operatively coupled with the at least one processor, the camera, and the gamma camera sensors, the memory having instructions for execution by the at least one processor that cause the at least one processor to:
    read a first gamma-ray photon sensing event received from the gamma camera sensors;
    provide a first position and orientation of the gamma camera panel with respect to a body of the patient;
    co-register the first gamma-ray photon sensing event to the body of the patient using the first position and orientation;
    read a second gamma-ray photon sensing event received from the gamma sensors;
    provide a second position and orientation of the gamma camera panel with respect to the body of the patient,
    co-register the second gamma-ray photon sensing event to the body of the patient using the second position and orientation; and
    reconstruct a 3D distribution of gamma-ray emitting radioisotopes inside the patient by using first and second co-registered sensing events.

2. The system of claim 1, wherein the jointed arm is a computer controllable 6-axis robotic arm.

3. The system of claim 1, wherein the memory further has instructions that cause the at least one processor to actuate the mechanical arm to perform a SPECT scan.

4. The system of claim 3, further comprising wheels actuated by a motor coupled to the at least one processor and the memory, wherein the wheels are actuated to move the SPECT system during a scan of the patient.

5. The system of claim 3, further comprising a proximity sensor mounted on the panel, wherein the proximity sensor is operationally coupled to the at least one processor and the memory, wherein movement of the panels with respect to the patient is modified depending on proximity sensor data obtained by the proximity sensor.

6. The system of claim 1, wherein the memory further has instructions that cause the at least one processor to:
    create, using computer vision, 3D models of the body of the patient at regular intervals; and
    detect body changes and deformations taking place from one 3D model of the body to another.

7. The system of claim 6, wherein the memory further has instructions that cause the at least one processor to inform the user of a significant body change that may require a reset of the SPECT scan.

8. The system of claim 6, wherein the memory further has instructions that cause the at least one processor to:
    determine and assign a first 3D patient body model to a first sensor detection event,
    determine and assign a second 3D patient body model to a second sensor detection event,
    create a tissue deformation model from first to second 3D patient body models, and
    reconstruct a 3D distribution of gamma-ray emitting radioisotopes inside the patient by using first and second sensing events and the tissue deformation model.

9. The system of claim 1, wherein the memory further has instructions that cause the at least one processor to stop movement of the jointed arm and gamma camera panels to avoid collisions between components of the SPECT imaging system with the body of the patient.

10. The system of claim 9, wherein the memory further has instructions that cause the at least one processor to:
    monitor space in a projected path of the gamma camera panels for other objects or people, and
    stop the movement of the jointed arm and gamma camera panels to avoid collisions between any components of the SPECT imaging system with the other objects or people.

11. The system of claim 1, further comprising:
    an ultrasound probe;
    a tracking system, wherein the tracking system is used to determine the position and orientation of the ultrasound probe with respect to a body of the patient;
    a visualization device;
    at least one processor and a memory operatively coupled with the ultrasound probe, tracking system, a memory storing a 3D distribution of gamma-ray emitting radioisotopes co-registered to the patient or to a point of reference, and the visualization device, the memory having instructions for execution by the at least one processor that cause the at least one processor to:
    track the ultrasound probe with respect to the patient or with respect to a point of reference;
    determine a co-registration between the 3D distribution of gamma-ray emitting radioisotopes and an ultrasound scan using ultrasound probe tracking data obtained by the ultrasound probe; and
    deliver to the visualization device an image that comprises an augmentation of features of the 3D distribution of gamma-ray emitting radioisotopes onto the ultrasound scan.

12. The system of claim 11, wherein the tracking system is selected from a group containing an optical tracking system, an electro-mechanical tracking system, an electro-magnetic tracking system, an ultrasound tracking system, a depth imaging tracking system, a combination thereof.

13. The system of claim 11, wherein the memory further has instructions that cause the at least one processor to:
    read a SPECT image dataset from a memory,
    create a model of movements of features in the image from a first ultrasound frame to a second ultrasound frame,
    create a changed SPECT image based on the model of movements of features in the image, and
    augment the changed SPECT image onto the second ultrasound frame.

14. A real-time multi-modality portable Single Photon Emission Computer Tomography (SPECT) imaging system to scan a patient, the system comprising:
    a SPECT controller unit, unit comprising at least a computer;

a mechanical jointed arm connected to the controller unit, wherein the jointed arm can be positioned to a desired location by a user through applying direct force;

at least one gamma camera panel connected to the jointed arm, wherein the gamma camera panel comprises gamma camera sensors with position and energy sensing resolution;

an ultrasound transducer positionable in such a way as to have a field of view that at least partially overlaps with a gamma camera field of view;

a tracking system able to provide tracking information about a relative position of the ultrasound transducer with respect to the gamma camera;

a visualization device; and at least one processor and a memory operatively coupled with the gamma camera sensors, ultrasound transducer, tracking system and visualization device, the memory having instructions for execution by the at least one processor that cause the at least one processor to:

read a first gamma-ray photon sensing event received from the gamma sensors;

read a second gamma-ray photon sensing event received from the gamma sensors;

reconstruct a 3D distribution of gamma-ray emitting radioisotopes inside the patient by using first and second sensing events;

determine a co-registration between the ultrasound transducer and the gamma sensors using the tracking information;

determine a co-registration between the 3D distribution of gamma-ray emitting radioisotopes and an ultrasound scan using the co-registration between the ultrasound transducer and the gamma sensors; and deliver to the visualization device an image that comprises an augmentation of the 3D distribution of gamma-ray emitting radioisotopes onto the ultrasound scan by using the co-registration between the 3D distribution of gamma-ray emitting radioisotopes and an ultrasound scan.

15. The system of claim 14, wherein the gamma camera panel provides an imaging field of view that is larger than 15 degrees, the imaging field of view being defined as a range of angles, with respect to a direction at which the gamma camera has maximum imaging sensitivity, from which gamma photons can be detected and imaged by gamma sensors comprised by the gamma camera panel with a sensitivity larger than a hundredth the maximum imaging sensitivity.

16. The system of claim 14, wherein the reconstructed 3D distribution of gamma-ray emitting radioisotopes is characterized by a finite depth imaging resolution of less than 20 millimeters (mm) from an essentially static position of the gamma camera panel with respect to the patient along the direction at which the gamma camera is most sensitive for a range of distances that cover at least 50 mm.

17. The system of claim 14, wherein the ultrasound transducer is affixed to a body of the patient without a user holding the transducer.

18. The system of claim 14, wherein at least one processor and a memory operatively coupled with the gamma camera sensors, ultrasound transducer, tracking system, the memory having instructions for execution by the at least one processor that cause the at least one processor to:

read a gamma-ray photon sensing event received from the gamma sensors, thereby detecting a gamma-ray photon;

associate a ultrasound image map with the gamma-ray photon sensing event;

provide a tissue model from the ultrasound image map;

create a gamma photon attenuation model from the tissue model; and use the gamma photon attenuation model to determine attenuation probabilities inside the patient for the detected gamma-ray photon.

19. The system of claim 14, comprising first and second gamma camera panels mounted at a distal end of the jointed arm, wherein the panels can be actuated so that a distance between the panels can be modified, wherein the panels can be actuated so that the relative angle between the panels can be modified, and wherein the panels can be separated to allow another medical instrument to be positioned between the panels.

20. The system of claim 19, wherein the medical instrument is an ultrasound probe.

21. The system of claim 19, wherein the medical instrument is a biopsy needle.

22. The system of claim 19, wherein the medical instrument is an ablation treatment device.

23. A portable Single Photon Emission Computer Tomography (SPECT) imaging system to scan a body part of a patient, the system comprising:

a SPECT controller unit, the controller unit comprising at least a computer;

a mechanical jointed arm connected to the controller unit;

a gamma camera panel connected to the jointed arm, wherein the gamma camera panel comprises gamma camera sensors with position and energy sensing resolution, wherein the gamma camera panel provides an imaging field of view that is larger than 15 degrees, the imaging field of view being defined as a range of angles, with respect to a direction at which the gamma camera has maximum imaging sensitivity, from which gamma photons can be detected and imaged by gamma sensors comprised by the gamma camera panel with a sensitivity larger than a hundredth the maximum imaging sensitivity; and a tactile pressure sensor mounted on the panel, wherein the tactile pressure sensor is operationally coupled to at least one processor and memory, wherein movement of the panels with respect to the patient is modified depending on tactile pressure sensor data obtained by the tactile pressure sensor.

24. The system of claim 23, further comprising a second gamma camera panel mounted at a distal end of the jointed arm, wherein the panels can be actuated so that a distance between the panels can be modified, wherein the panels can be actuated so that a relative angle between the panels can be modified, and wherein the panels can be positioned essentially face to face and to allow a body part of the patient to be positioned between the panel faces.

* * * * *